United States Patent
Henry

(10) Patent No.: US 11,279,684 B2
(45) Date of Patent: Mar. 22, 2022

(54) SUBSTITUTED IMIDAZOQUINOLINES AS AGONISTS OF TLR7

(71) Applicant: BIONTECH SE, Mainz (DE)

(72) Inventor: Christophe Henry, Munich (DE)

(73) Assignee: Bointech SE

( * ) Notice: Subject to any disclaimer, the term of this patent is extended or adjusted under 35 U.S.C. 154(b) by 0 days.

(21) Appl. No.: 16/644,079

(22) PCT Filed: Aug. 31, 2018

(86) PCT No.: PCT/EP2018/073485
§ 371 (c)(1),
(2) Date: Mar. 3, 2020

(87) PCT Pub. No.: WO2019/048353
PCT Pub. Date: Mar. 14, 2019

(65) Prior Publication Data
US 2021/0002249 A1    Jan. 7, 2021

(30) Foreign Application Priority Data
Sep. 6, 2017 (WO) .................. PCT/EP2017/072353

(51) Int. Cl.
A61P 35/00    (2006.01)
C07D 471/04    (2006.01)
C07D 401/04    (2006.01)

(52) U.S. Cl.
CPC ............ *C07D 401/04* (2013.01); *A61P 35/00* (2018.01); *C07D 471/04* (2013.01)

(58) Field of Classification Search
CPC .............................. C07D 471/04; A61P 35/00
See application file for complete search history.

(56) References Cited

U.S. PATENT DOCUMENTS 6,573,273 B1    6/2003 Crooks et al.

FOREIGN PATENT DOCUMENTS

| EA | 023556 | 6/2016 |
| RU | 2 374 246 | 6/2004 |
| WO | 2005/051324 | 6/2005 |
| WO | WO 2005051324 | 6/2005 |
| WO | 2009/118296 | 10/2009 |
| WO | WO 2017/040233 | 3/2017 |

OTHER PUBLICATIONS

The International Search Report (ISR) with Written Opinion for PCT/EP2018/073485 dated Oct. 16, 2018, pp. 1-9.
Belikov et al, "Pharmaceutical Chemistry Manual", 4th edition, 2007, 6 pages.
Kummerer et al, "Pharmaceuticals in the Environment", Annual Review Environmental Resources, 2010, 35:57-75.
Durnov et al, "Pediatric Oncology", Second edition, 2002, 2 pages.
Small Medical Encyclopedia, Academician of the Russian Academy of Medical Sciences, vol. 5, 1996.
Office Action for Application No. RU2020112231 dated Nov. 3, 2021, 10 pages.
Search Report for PCTEP2017072353 dated Sep. 28, 2021.

*Primary Examiner* — Alicia L Otton
(74) *Attorney, Agent, or Firm* — McDonnell Boehnen Hulbert & Berghoff LLP

(57) ABSTRACT

The invention relates to imidazoquinoline derivatives and to pharmaceutical compositions containing the imidazoquinoline derivatives. The imidazoquinoline derivatives of the invention are useful as toll-like receptor agonists, in particular agonists of TLR7, and promote induction of certain cytokines.

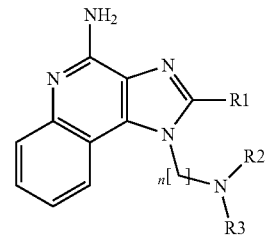

15 Claims, No Drawings

SUBSTITUTED IMIDAZOQUINOLINES AS AGONISTS OF TLR7

CROSS-REFERENCE TO RELATED APPLICATIONS

This application is a U.S. national phase of International Application No. PCT/EP2018/073485, filed Aug. 31, 2018, which claims priority from PCT/EP2017/072353, filed Sep. 6, 2017, the disclosure of each of which is hereby incorporated by reference in its entirety.

FIELD OF THE INVENTION

The invention relates to imidazoquinoline derivatives and to pharmaceutical compositions containing the imidazoquinoline derivatives. The imidazoquinoline derivatives are useful as toll-like receptor agonists, in particular agonists of TLR7, and promote induction of certain cytokines.

BACKGROUND OF THE INVENTION

Toll-like receptors (TLR) currently comprising a gene family of 13 receptors with different specificities, 11 of them found in humans, are part of the cellular pathogen pattern recognition system, which has evolved for defense against a variety of infections (bacteria, virus, fungi). Activation of TLRs leads to cytokine responses, e.g. with release of interferons and activation of specified immune cells. The functional expression of selected TLRs in tissues is highly different. Part of the receptors are located at the cell surface such as TLR4 (stimulated by *E. coli* lipopolysaccharide LPS), e.g. on epithelial cells, or TLR3, 7, 8 and 9 located at endosomal membranes in specified immune cells. The latter are all activated by nucleic acids, but recognize various types of them. For instance, TLR9 is activated by single-stranded DNA containing CpG subsequences, TLR7 and 8 are activated by single-stranded RNA, and TLR3 is activated by double-stranded RNA.

Some small-molecule (SMOL) TLR7 or TLR8 agonists have been identified. Those agonists can be grouped into purine-like molecules, such as 7-thia-8-oxoguanosine (TOG, isatoribine) or the imidazoquinoline-based compounds like imiquimod. Imiquimod is so far the only approved definitive TLR7 agonist, marketed as 5% cream (by Aldara). It generates approx. 80% 5-year clearance of superficial basal cell carcinomas, which is the most frequent cancer worldwide. Imiquimod activates TLR7. The functional expression of TLR7 appears to be restricted to specific immune cells, i.e. in humans plasmacytoid dendritic cells, B-cells and probably eosinophils are known to be activated by TLR7 agonists.

Since several years, strong efforts are ongoing worldwide trying to exploit the strong immune activation induced by TLR7, 8 or 9 agonists for the treatment of cancer. Cancer immunotherapy, however, experienced a long history of failures. In recent years, though, the knowledge on cancer immune surveillance and the function of subsets of immune cells thereby was improved drastically. TLR7, TLR8 or TLR9 agonists are in clinical development for cancer mono- or combination therapies, or as vaccine adjuvant.

The TLR agonist approach for cancer immunotherapy is different from earlier efforts using, e.g. cytokines, interferons or monovalent vaccinations. TLR agonist mediated immune activation is pleiotropic via specified immune cells (primarily dendritic cells and B-cells, subsequently other cells), which generates an innate and adaptive immune response. Moreover, not only one interferon is induced, but rather the many different isoforms altogether, and not only type I (alpha, beta), but also (indirectly) type II (gamma, NK cells). At least for local application, Aldara has delivered a remarkable proof-of-concept. This demonstrates that antigens are released by tumors, and that immune therapy can work for cancer indications in principle, and even in monotherapy. For a systemic administration route, though, the clinical POC is pending for TLR7 agonists. For advanced cancers and systemic application (particularly s.c. or i.v. administration route) it appears to be clear that such TLR agonists might provide stronger, i.e. synergistic, efficacy in combination with other therapeutic interventions.

In case of earlier stages of cancer, the situation might be different. Tumor metastasis is a severe aspect of tumor development in patients, largely because tumors are detected too late when metastasis already has occurred. Established tumor therapies mostly include cytotoxic drugs with rather narrow therapeutic windows. Hence, for the treatment in earlier tumor stages, when the suppression of metastasis spread might still be possible, the need is high for new therapies with good tolerability and safety.

The activation of the immune system, and in particular, the activation of toll-like receptor (TLR) signaling offers new promising approaches. TLR9 agonistic CpG-ODN like H2006 or H1826, and TLR7 agonists like the guanosine derivative isatoribine or an Imiquimod derivative were tested in a murine Renca lung metastasis model. All tested molecules virtually completely suppressed the emergence of lung metastases with good tolerability. This provides a convincing rational for clinical development of such molecules for suppression of cancer metastasis and points to the possibility of systemic application of such drugs. However, the SMOL type TLR7 agonists have the advantage of established and cost effective synthesis if compared to the nucleic acid type TLR9 agonists, and are well suited for topical application.

U.S. Pat. No. 6,573,273 describes imidazoquinoline and tetrahydroimidazoquinoline compounds that contain urea, thiourea, acylurea, sulfonylurea or carbamate functionality. The compounds are said to be useful as immunomodulators.

U.S. Pat. No. 6,677,349 describes imidazoquinoline and tetrahydroimidazoquinoline compounds that contain sulfonamide functionality at the 1-position. The compounds are said to be useful as immunomodulators.

US-A-2003/0144283 and WO-A-00/76505 describe imidazoquinoline and tetrahydroimidazoquinoline compounds that contain amide functionality at the 1-position. The compounds are said to be useful as immunomodulators.

WO-A-2005/051324 describes imidazoquinoline, pyridine and naphthyridine rind systems substituted in 1-position with oxime or a special N-oxide functionality. The compounds are said to be useful as immunomodulators.

WO-A-2009/118296 describes imidazoquinoline compounds. The compounds are described as toll-like receptor agonist/TLR7 activators.

SUMMARY OF THE INVENTION

The present invention provides imidazoquinoline-4-amine compounds with certain specific substituents, physiologically functional derivatives, solvates and salts thereof, as further described in the following. Said compounds are agonists or activators for TLR7 and may serve as cytokine inducing compounds. Said compounds have the general Formula (I):

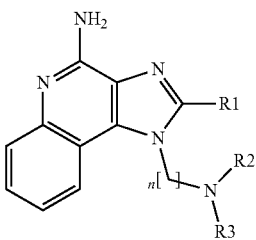

wherein: R1, R2, R3 and n are as defined below.

In another aspect, the present invention provides methods for the preparation of certain compounds of Formula (I), physiologically functional derivatives, solvates or salts thereof, as detailed further herein below.

In another aspect, the present invention provides methods for the treatment or prevention of certain medical conditions, the method comprising the administration of compounds of Formula (I), physiologically functional derivatives, solvates or salts thereof, to a subject in need thereof, as detailed further herein below.

In another aspect, the present invention provides the use of compounds of Formula (I), physiologically functional derivatives, solvates or salts thereof, in the manufacture of a medicament for the treatment or prevention of certain medical conditions, as detailed further herein below.

In another aspect, the present invention provides compounds of Formula (I), physiologically functional derivatives, solvates or salts thereof, for use as medicament, in particular for use in the treatment or prevention of certain medical conditions, as detailed further herein below.

In another aspect, the present invention provides pharmaceutical compositions comprising compounds of Formula (I), physiologically functional derivatives, solvates or salts thereof and one or more pharmaceutically acceptable excipients.

The compounds of Formula (I) are for instance useful as TLR7 activators.

DETAILED DESCRIPTION OF INVENTION

It has been found that the imidazoquinoline derivatives of Formula (I), physiologically functional derivatives, solvates or salts thereof, which are described in greater detail below, are particularly effective TLR7 agonists and have surprising and particularly advantageous properties.

The present invention provides compounds of Formula (I):

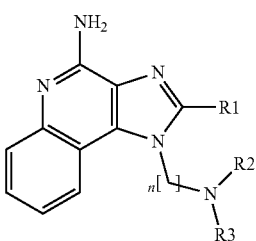

wherein
R1 is selected from the group consisting of —H, $C_{1-6}$-alkyl, $C_{1-6}$-alkoxy, $C_{1-3}$-alkoxy-$C_{1-3}$-alkyl, $C_{1-6}$-alkylthio, $C_{1-3}$-alkylthio-$C_{1-3}$-alkyl, $C_{1-3}$-alkylamino-$C_{1-3}$-alkyl, 4- to 10-membered heterocycloalkyl, $C_{3-10}$-cycloalkyl, $C_{6-40}$-aryl, $C_{6-10}$-aryl-$C_{1-2}$-alkyl and 5- to 10-membered heteroaryl,
wherein said $C_{1-6}$-alkyl, $C_{1-6}$-alkoxy, $C_{1-3}$-alkoxy-$C_{1-3}$-alkyl, $C_{1-6}$-alkylthio, $C_{1-3}$-alkylthio-$C_{1-3}$-alkyl, $C_{1-3}$-alkylamino-$C_{1-3}$-alkyl, $C_{6-10}$-aryl, 4- to 10-membered heterocycloalkyl, $C_{3-10}$-cycloalkyl, $C_{6-10}$-aryl-$C_{1-2}$-alkyl and 5- to 10-membered heteroaryl is optionally substituted by one or more groups independently selected from the group consisting of $C_{1-4}$-alkyl, —OH, halogen, —CO—N(R4)$_2$, —N(R4)$_2$, —CO—R4, —COO—R4, —N$_3$, —NO$_2$, and —CN;
R2 is selected from the group consisting of —CO—R5, —CONH—R5, and —COO—R5;
R3 is 1,1-dioxothietan-3-yl, which is optionally substituted by one or more groups independently selected from the group consisting of $C_{1-4}$-alkyl, —OH, and halogen;
R4 is each independently selected from the group consisting of H and $C_{1-4}$-alkyl;
n is an integer from 3 to 6; and
R5 is selected from the group consisting of —H, $C_{1-6}$-alkyl, $C_{1-6}$-alkoxy, $C_{1-3}$-alkoxy-$C_{1-3}$-alkyl, $C_{1-6}$-alkylthio, $C_{1-3}$-alkylthio-$C_{1-3}$-alkyl, $C_{1-3}$-alkylamino-$C_{1-3}$-alkyl, $C_{6-10}$-aryl, 4- to 10-membered heterocycloalkyl, $C_{3-10}$-cycloalkyl and 5- to 10-membered heteroaryl,
wherein said $C_{1-6}$-alkyl, $C_{1-6}$-alkoxy, $C_{1-3}$-alkoxy-$C_{1-3}$-alkyl, $C_{1-6}$-alkylthio, $C_{1-3}$-alkylthio-$C_{1-3}$-alkyl, $C_{1-3}$-alkylamino-$C_{1-3}$-alkyl, $C_{6-10}$-aryl, 4- to 10-membered heterocycloalkyl, $C_{3-10}$-cycloalkyl and 5- to 10-membered heteroaryl, is optionally substituted by one or more groups independently selected from the group consisting of $C_{1-4}$-alkyl, —OH, halogen, —CO—N(R4)$_2$, —N(R4)$_2$, —CO—R4, —COO—R4, —N$_3$, —NO$_2$, and —CN;
or a physiologically functional derivative, solvate or salt thereof.

In particular embodiments of the present invention, R1 is selected from the group consisting of $C_{1-6}$-alkyl, $C_{1-3}$-alkoxy-$C_{1-3}$-alkyl, $C_{1-3}$-alkylthio-$C_{1-3}$-alkyl, and $C_{1-3}$-alkylamino-$C_{1-3}$-alkyl, more particularly $C_{1-6}$-alkyl, $C_{1-3}$-alkoxy-$C_{1-3}$-alkyl, and $C_{1-3}$-alkylamino-$C_{1-3}$-alkyl, wherein said $C_{1-6}$-alkyl, $C_{1-3}$-alkoxy-$C_{1-3}$-alkyl, $C_{1-3}$-alkylthio-$C_{1-3}$-alkyl, or $C_{1-3}$-alkylamino-$C_{1-3}$-alkyl is optionally substituted by one or more groups independently selected from the group consisting of —OH and halogen.

Even more particularly, R1 is selected from the group consisting of ethyl, methyl, propyl, butyl, methoxyethyl, and ethylaminomethyl, each of which is optionally substituted by one or more groups independently selected from the group consisting of —OH and halogen, yet even more particularly each of which is unsubstituted.

Yet even more particularly, R1 is selected from the group consisting of ethyl, propyl, butyl, methoxyethyl, and ethylaminomethyl, each of which is optionally substituted by one or more groups independently selected from the group consisting of —OH and halogen, yet even more particularly each of which is unsubstituted.

Yet even more particularly, R1 is selected from the group consisting of ethyl, methoxyethyl, and ethylaminomethyl, each of which is optionally substituted by one or more groups independently selected from the group consisting of —OH and halogen, yet even more particularly each of which is unsubstituted.

Yet even more particularly, R1 is unsubstituted methoxyethyl.

Also yet even more particularly, R1 is unsubstituted ethylaminomethyl.

In particular embodiments of the present invention, R2 is —CO—R5.

In other particular embodiments of the present invention, R2 is selected from the group consisting of —COO—R5 and —CONH—R5, more particularly —CONH—R5.

In particular embodiments of the present invention, R3 is unsubstituted 1,1-dioxothietan-3-yl.

In particular embodiments of the present invention, R4 is each independently selected from the group consisting of H and methyl, more particularly H.

In particular embodiments of the present invention, n is 4.

In particular embodiments of the present invention, R5 is selected from the group consisting of H, $C_{1-4}$-alkyl, $C_{1-3}$-alkoxy-$C_{1-3}$-alkyl, $C_{1-3}$-alkylamino-$C_{1-3}$-alkyl, phenyl, 5- to 6-membered heterocycloalkyl, $C_{5-6}$-cycloalkyl and 5- to 6-membered heteroaryl, more particularly H, $C_{1-4}$-alkyl, $C_{1-3}$-alkoxy-$C_{1-3}$-alkyl, phenyl, and $C_{5-6}$-cycloalkyl, even more particularly H, $C_{1-4}$-alkyl, wherein said $C_{1-4}$-alkyl, $C_{1-3}$-alkoxy-$C_{1-3}$-alkyl, $C_{1-3}$-alkylamino-$C_{1-3}$-alkyl, phenyl, 5- to 6-membered heterocycloalkyl, $C_{5-6}$-cycloalkyl and 5- to 6-membered heteroaryl is optionally substituted by one or more groups independently selected from the group consisting of $C_{1-2}$-alkyl, —OH, halogen, —CO—N(R4)$_2$, —N(R4)$_2$, —CO—R4, —COO—R4, —N$_3$, —NO$_2$, and —CN, more particularly $C_{1-2}$-alkyl, —OH, halogen, NH$_2$, —COMe, —COOH, —COOMe, and —CN, even more particularly methyl, —OH and halogen.

More particularly, R5 is selected from the group consisting of H, methyl, ethyl, propyl and butyl, even more particularly H, methyl or ethyl, yet even more particularly H or methyl.

In particular embodiments of the present invention, R2 is —CO—R5, wherein R5 is selected from the group consisting of $C_{1-4}$-alkyl, $C_{1-3}$-alkoxy-$C_{1-3}$-alkyl, and $C_{1-3}$-alkylamino-$C_{1-3}$-alkyl, more particularly $C_{1-4}$-alkyl and $C_{1-3}$-alkoxy-$C_{1-3}$-alkyl, more particularly R5 is $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is optionally substituted by one or more groups independently selected from the group consisting of $C_{1-2}$-alkyl, —OH, halogen, —CO—N(R4)$_2$, —N(R4)$_2$, —CO—R4, —COO—R4, —N$_3$, —NO$_2$, and —CN, more particularly $C_{1-2}$-alkyl, —OH, halogen, NH$_2$, —COMe, —COOH, —COOMe, and —CN, even more particularly methyl, —OH and halogen. In one embodiment, R2 is CO—R5, wherein R5 is selected from the group consisting of $C_{1-4}$-alkyl, $C_{1-3}$-alkoxy-$C_{1-3}$-alkyl, and $C_{1-3}$-alkylamino-$C_{1-3}$-alkyl, more particularly $C_{1-4}$-alkyl and $C_{1-3}$-alkoxy-$C_{1-3}$-alkyl, more particularly R5 is $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is unsubstituted.

In particular embodiments of the present invention, R2 is —CONH—R5, wherein R5 is selected from the group consisting of H, $C_{1-4}$-alkyl, $C_{1-3}$-alkoxy-$C_{1-3}$-alkyl, and $C_{1-3}$-alkylamino-$C_{1-3}$-alkyl, more particularly H and $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is optionally substituted by one or more groups independently selected from the group consisting of $C_{1-2}$-alkyl, —OH, halogen, —CO—N(R4)$_2$, —N(R4)$_2$, —CO—R4, —COO—R4, —N$_3$, —NO$_2$, and —CN, more particularly $C_{1-2}$-alkyl, —OH, halogen, NH$_2$, —COMe, —COOH, —COOMe, and —CN, even more particularly methyl, —OH and halogen. In one embodiment, R2 is —CONH—R5, wherein R5 is selected from the group consisting of H, $C_{1-4}$-alkyl, $C_{1-3}$-alkoxy-$C_{1-3}$-alkyl, and $C_{1-3}$-alkylamino-$C_{1-3}$-alkyl, more particularly H and $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is unsubstituted.

In particular embodiments of the present invention, R2 is —COO—R5, wherein R5 is selected from the group consisting of H, $C_{1-4}$-alkyl, $C_{1-3}$-alkoxy-$C_{1-3}$-alkyl, and $C_{1-3}$-alkylamino-$C_{1-3}$-alkyl, more particularly $C_{1-4}$-alkyl or $C_{1-3}$-alkoxy-$C_{1-3}$-alkyl, more particularly R5 is $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is optionally substituted by one or more groups independently selected from the group consisting of $C_{1-2}$-alkyl, —OH, halogen, —CO—N(R4)$_2$, —N(R4)$_2$, —CO—R4, —COO—R4, —N$_3$, —NO$_2$, and —CN, more particularly $C_{1-2}$-alkyl, —OH, halogen, NH$_2$, —COMe, —COOH, —COOMe, and —CN, even more particularly methyl, —OH and halogen. In one embodiment, R2 is —COO—R5, wherein R5 is selected from the group consisting of H, $C_{1-4}$-alkyl, $C_{1-3}$-alkoxy-$C_{1-3}$-alkyl, and $C_{1-3}$-alkylamino-$C_{1-3}$-alkyl, more particularly $C_{1-4}$-alkyl or $C_{1-3}$-alkoxy-$C_{1-3}$-alkyl, more particularly R5 is $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is unsubstituted.

In one embodiment, R2 is —CONH$_2$, —CO-Me, —COOMe, or —COOH, particularly —CONH$_2$, —CO-Me, or —COOMe, more particularly —CONH$_2$ or —CO-Me.

In particular embodiments of the present invention, R1 is selected from the group consisting of $C_{1-6}$-alkyl, $C_{1-3}$-alkoxy-$C_{1-3}$-alkyl, $C_{1-3}$-alkylthio-$C_{1-3}$-alkyl, and $C_{1-3}$-alkylamino-$C_{1-3}$-alkyl, more particularly $C_{1-6}$-alkyl, $C_{1-3}$-alkoxy-$C_{1-3}$-alkyl, and $C_{1-3}$-alkylamino-$C_{1-3}$-alkyl, wherein said $C_{1-6}$-alkyl, $C_{1-3}$-alkoxy-$C_{1-3}$-alkyl, $C_{1-3}$-alkylthio-$C_{1-3}$-alkyl, or $C_{1-3}$-alkylamino-$C_{1-3}$-alkyl is optionally substituted by one or more groups independently selected from the group consisting of —OH and halogen; and R2 is —CO—R5, wherein R5 is selected from the group consisting of $C_{1-4}$-alkyl, $C_{1-3}$-alkoxy-$C_{1-3}$-alkyl, and $C_{1-3}$-alkylamino-$C_{1-3}$-alkyl, more particularly $C_{1-4}$-alkyl and $C_{1-3}$-alkoxy-$C_{1-3}$-alkyl, more particularly R5 is $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is optionally substituted by one or more groups independently selected from the group consisting of $C_{1-2}$-alkyl, —OH, halogen, —CO—N(R4)$_2$, —N(R4)$_2$, —CO—R4, —COO—R4, —N$_3$, —NO$_2$, and —CN, more particularly $C_{1-2}$-alkyl, —OH, halogen, NH$_2$, —COMe, —COOH, —COOMe, and —CN, even more particularly methyl, —OH and halogen. In one embodiment, R2 is CO—R5, wherein R5 is selected from the group consisting of $C_{1-4}$-alkyl, $C_{1-3}$-alkoxy-$C_{1-3}$-alkyl, and $C_{1-3}$-alkylamino-$C_{1-3}$-alkyl, more particularly $C_{1-4}$-alkyl and $C_{1-3}$-alkoxy-$C_{1-3}$-alkyl, more particularly R5 is $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is unsubstituted. In these embodiments, it is preferred that R3 is unsubstituted 1,1-dioxothietan-3-yl and/or n is 4.

In particular embodiments of the present invention, R1 is selected from the group consisting of $C_{1-6}$-alkyl, $C_{1-3}$-alkoxy-$C_{1-3}$-alkyl, $C_{1-3}$-alkylthio-$C_{1-3}$-alkyl, and $C_{1-3}$-alkylamino-$C_{1-3}$-alkyl, more particularly $C_{1-6}$-alkyl, $C_{1-3}$-alkoxy-$C_{1-3}$-alkyl, and $C_{1-3}$-alkylamino-$C_{1-3}$-alkyl, wherein said $C_{1-6}$-alkyl, $C_{1-3}$-alkoxy-$C_{1-3}$-alkyl, $C_{1-3}$-alkylthio-$C_{1-3}$-alkyl, or $C_{1-3}$-alkylamino-$C_{1-3}$-alkyl is optionally substituted by one or more groups independently selected from the group consisting of —OH and halogen; and R2 is —CONH—R5, wherein R5 is selected from the group consisting of H, $C_{1-4}$-alkyl, $C_{1-3}$-alkoxy-$C_{1-3}$-alkyl, and $C_{1-3}$-alkylamino-$C_{1-3}$-alkyl, more particularly H and $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is optionally substituted by one or more groups independently selected from the group consisting of $C_{1-2}$-alkyl, —OH, halogen, —CO—N(R4)$_2$, —N(R4)$_2$, —CO—R4, —COO—R4, —N$_3$, —NO$_2$, and —CN, more particularly $C_{1-2}$-alkyl, —OH, halogen, NH$_2$, —COMe, —COOH, —COOMe, and —CN, even more particularly methyl, —OH and halogen. In one embodiment, R2 is —CONH—R5, wherein R5 is selected from the group consisting of H, $C_{1-4}$-alkyl, $C_{1-3}$-alkoxy-$C_{1-3}$-alkyl, and $C_{1-3}$-alkylamino-$C_{1-3}$-alkyl, more particularly H and $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is unsubstituted. In these embodiments, it is preferred that R3 is unsubstituted 1,1-dioxothietan-3-yl and/or n is 4.

In particular embodiments of the present invention, R1 is selected from the group consisting of $C_{1-6}$-alkyl, $C_{1-3}$-alkoxy-$C_{1-3}$-alkyl, $C_{1-3}$-alkylthio-$C_{1-3}$-alkyl, and $C_{1-3}$-alkylamino-$C_{1-3}$-alkyl, more particularly $C_{1-6}$-alkyl, $C_{1-3}$-alkoxy-$C_{1-3}$-alkyl, and $C_{1-3}$-alkylamino-$C_{1-3}$-alkyl, wherein said $C_{1-6}$-alkyl, $C_{1-3}$-alkoxy-$C_{1-3}$-alkyl, $C_{1-3}$-alkylthio-$C_{1-3}$-alkyl, or $C_{1-3}$-alkylamino-$C_{1-3}$-alkyl is optionally substituted by one or more groups independently selected from the group consisting of —OH and halogen; and R2 is —COO—R5, wherein R5 is selected from the group consisting of H, $C_{1-4}$-alkyl, $C_{1-3}$-alkoxy-$C_{1-3}$-alkyl, and $C_{1-3}$-alkylamino-$C_{1-3}$-alkyl, more particularly $C_{1-4}$-alkyl or $C_{1-3}$-alkoxy-$C_{1-3}$-alkyl, more particularly R5 is $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is optionally substituted by one or more groups independently selected from the group consisting of $C_{1-2}$-alkyl, —OH, halogen, —CO—N(R4)$_2$, —N(R4)$_2$, —CO—R4, —COO—R4, —N$_3$, —NO$_2$, and —CN, more particularly $C_{1-2}$-alkyl, —OH, halogen, NH$_2$, —COMe, —COOH, —COOMe, and —CN, even more particularly methyl, —OH and halogen. In one embodiment, R2 is —COO—R5, wherein R5 is selected from the group consisting of H, $C_{1-4}$-alkyl, $C_{1-3}$-alkoxy-$C_{1-3}$-alkyl, and $C_{1-3}$-alkylamino-$C_{1-3}$-alkyl, more particularly $C_{1-4}$-alkyl or $C_{1-3}$-alkoxy-$C_{1-3}$-alkyl, more particularly R5 is $C_{1-4}$-alkyl, wherein said $C_{1-4}$-alkyl, $C_{1-3}$-alkoxy-$C_{1-3}$-alkyl, and $C_{1-3}$-alkylamino-$C_{1-3}$-alkyl is unsubstituted.

The following definitions are meant to further define certain terms used in the context of the present invention. If a particular term used herein is not specifically defined, the term should not be considered to be indefinite. Rather, such terms are to be construed in accordance with their meaning as regularly understood by the skilled artisan in the field of art to which the invention is directed, particularly in the field of organic chemistry, pharmaceutical sciences and medicine.

The term "1,1-dioxothietan-3-yl" refers to a group of the below formula, wherein the interrupted bond specifies the point of attachment to the central moiety.

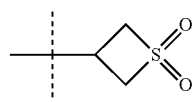

As used herein, the terms "alkyl" and the prefix "alk" are inclusive of both straight chain and branched chain groups and include the respective alkane, alkene and alkyne groups. It is apparent, that alkene and alkyne groups cannot consist only of a single carbon unit and such nonexistent groups are not comprised by the present invention; accordingly, and logically, terms such as $C_{1-x}$-alkyl (wherein x is an integer as specified in the respective context) include the respective $C_{1-x}$-alkanyl, $C_{2-x}$-alkenyl and $C_{2-x}$-alkynyl. Particular alkyl groups have a total of up to 5, particularly up to 4, more particularly up to 3 carbon atoms. In particular embodiments the alkyl group is selected from the group consisting of —CH$_3$, —C$_2$H$_5$, —CH=CH$_2$, —C≡CH, —C$_3$H$_7$, —CH(CH$_3$)$_2$, —CH$_2$—CH=CH$_2$, —C(CH$_3$)=CH$_2$, —CH=CH—CH$_3$, —C≡C—CH$_3$, —CH$_2$—C≡CH, —C$_4$H$_9$, —CH$_2$—CH(CH$_3$)$_2$, —CH(CH$_3$)—C$_2$H$_5$, —C(CH$_3$)$_3$, —C$_5$H$_{11}$, —C$_6$H$_{13}$, —C$_2$H$_4$—CH=CH$_2$, —CH=CH—C$_2$H$_5$, —CH=C(CH$_3$)$_2$, —CH$_2$—CH=CH—CH$_3$, —CH=CH—CH=CH$_2$, —C$_2$H$_4$—C≡CH, —C≡C—C$_2$H$_5$, —CH$_2$—C≡C—CH$_3$, —C≡C—CH=CH$_2$, —CH=CH—C≡CH, —C≡C—C≡CH, —C$_2$H$_4$—CH(CH$_3$)$_2$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —C$_3$H$_6$—CH=CH$_2$, —CH=CH—C$_3$H$_7$, —C$_2$H$_4$—CH=CH—CH$_3$, —CH$_2$—CH=CH—C$_2$H$_5$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —CH$_2$—CH=C(CH$_3$)$_2$, C(CH$_3$)=C(CH$_3$)$_2$, —C$_3$H$_6$—C≡CH, —C≡C—C$_3$H$_7$, —C$_2$H$_4$—C≡C—CH$_3$, —CH$_2$—C≡C—C$_2$H$_5$, —CH$_2$—C≡C—CH=CH$_2$, —CH$_2$—CH=CH—C≡CH, —CH$_2$—C≡C—C≡CH, —C≡C—CH=CH—CH$_3$, —CH=CH—C≡C—CH$_3$, —C≡C—C≡C—CH$_3$, —C≡C—CH$_2$—CH=CH$_2$, —CH=CH—CH$_2$—C≡CH, —C≡C—CH$_2$—C≡CH, —C(CH$_3$)=CH—CH=CH$_2$, —CH=C(CH$_3$)—CH=CH$_2$, —CH=CH—C(CH$_3$)=CH$_2$, —C(CH$_3$)=CH—C≡CH, —CH=C(CH$_3$)—C≡CH, —C≡C—C(CH$_3$)=CH$_2$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —C$_4$H$_8$—CH=CH$_2$, —CH=CH—C$_4$H$_9$, —C$_3$H$_6$—CH=CH—CH$_3$, —CH$_2$—CH=CH—C$_3$H$_7$, —C$_2$H$_4$—CH=CH—C$_2$H$_5$, —CH$_2$—C(CH$_3$)=C(CH$_3$)$_2$, —C$_2$H$_4$—CH=C(CH$_3$)$_2$, —C$_4$H$_8$—C≡CH, —C≡C—C$_4$H$_9$, —C$_3$H$_6$—C≡C—CH$_3$, —CH$_2$—C≡C—C$_3$H$_7$, and —C$_2$H$_4$—C≡C—C$_2$H$_5$, even more particularly methyl, ethyl, n-propyl, isopropyl, n-butyl, isobutyl, sec-butyl and tert-butyl, yet even more particularly methyl, ethyl, n-propyl and isopropyl, yet even more particularly methyl and ethyl. In one embodiment, the term "alkyl" only refers to alkanyl groups (i.e., excluding alkenyl and alkynyl groups), in particular those alkanyl groups shown above (i.e., —CH$_3$, —C$_2$H$_5$, —C$_3$H$_7$, etc.). All of the aforementioned alkyl groups, unless specified otherwise, are optionally substituted as detailed in the embodiments of the present invention, i.e. one or more hydrogen atoms are optionally replaced by a substituent as specified in said respective embodiment. Especially particularly, said alkyl groups are unsubstituted unless specified otherwise.

A particular form of an alkyl group is a haloalkyl group, which is an alkyl group as defined above, wherein one or more, particularly at least half, more particularly all of the hydrogen atoms on the hydrocarbon chain are replaced by halogen atoms. The haloalkyl group is particularly selected from the group consisting of —C(R7)$_3$, —CH$_2$—C(R7)$_3$, —C(R7)$_2$-CH$_3$, —C(R7)$_2$-C(R7)$_3$, —C(R7)$_2$-CH(R7)$_2$, —CH$_2$—CH(R7)$_2$, —CH(R7)-C(R7)$_3$, —CH(R7)-CH$_3$, and —C$_2$H$_4$—C(R7)$_3$, more particularly —C(R7)$_3$, wherein R7 represents halogen, particularly F. More particularly, haloalkyl is selected from the group consisting of —CF$_3$, —CHF$_2$, —CH$_2$CF$_3$, and —CF$_2$Cl, even more particularly haloalkyl is —CF$_3$.

Further, the term "alkynyl" particularly refers to an alkyl group having at least two carbon atoms and including a carbon-carbon triple bond. Substituted alkynyl is as defined above. The term, "alkenyl" particularly refers to an alkyl group having at least two carbon atoms and including a carbon-carbon double bond.

As used herein, a heteroaryl group particularly denotes an aromatic mono- or bicyclic hydrocarbon ring system wherein one or more carbon atoms are replaced by heteroatoms independently selected from the group consisting of O, N and S, wherein in the case of a monocyclic heteroaryl, said monocyclic heteroaryl may optionally be fused to a cycloalkyl or heterocycloalkyl ring, and wherein the total number of ring atoms in the heteroaryl group is five to ten, more particularly five or six. The point of attachment of said heteroaryl group to the central moiety may be located on the mono- or bicyclic hydrocarbon ring system or on the optionally fused cycloalkyl or heterocycloalkyl ring. Examples of the heteroaryl group are thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-oxadiazol-3-yl, 1,2,4-oxadiazol-5-yl, 1,2,5-oxadiazol-3-yl, benzoxazol-2-yl, benzoxazol-4-yl, benzoxazol-5-yl, benzisoxazol-3-yl, benzisoxazol-4-yl, benzisoxazol-5-yl, 1,2,5-oxadiazol-4-yl, 1,3,4-oxadiazol-2-yl, 1,2,4-thiadiazol-3-yl, 1,2,4-thiadiazol-5-yl, 1,3,4-thiadiazol-2-yl, isothiazol-3-yl, isothiazol-4-yl, isothiazol-5-yl, benzisothiazol-3-yl, benzisothiazol-4-yl, benzisothiazol-5-yl, 1,2,5-thiadiazol-3-yl, 1-imidazolyl, 2-imidazolyl, 1,2,5-thiadiazol-4-yl, 4-imidazolyl, benzimidazol-4-yl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, tetrahydroisoquinolinyl, purine, phthalazine, pteridine, thiatetraazaindene, thiatriazaindene, isothiazolopyrazine, 6-pyrimidinyl, 2,4-dimethoxy-6-pyrimidinyl, benzimidazol-2-yl, 1H-benzimidazolyl, benzimidazol-4-yl, benzimidazol-5-yl, benzimidazol-6-yl, benzimidazol-7-yl, tetrazole, tetrahydro-thieno[3,4-d]imidazol-2-one, pyrazolo[5,1-c][1,2,4]triazine, isothiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, or triazolopyridazine. All of the aforementioned heteroaryl groups, unless specified otherwise, are optionally substituted as detailed in the embodiments of the present invention, i.e. one or more hydrogen atoms are optionally replaced by a substituent as specified in said respective embodiment. Especially particularly, said heteroaryl groups are unsubstituted unless specified otherwise.

As used herein, a cycloalkyl group particularly denotes a non-aromatic, mono- or bicyclic completely saturated or partially unsaturated hydrocarbon ring system, including bicyclic ring systems wherein one of the rings is a phenyl ring, such as 1,2,3,4-tetrahydronaphthalene. Said cycloalkyl is particularly monocyclic. Said cycloalkyl is particularly completely saturated. Said cycloalkyl comprises 3 to 10 carbon atoms, more particularly 5 to 7 carbon atoms. Even more particularly, said cycloalkyl is selected from the group consisting of cyclopropyl, cyclobutyl, cyclopentyl, cyclohexyl, cycloheptyl, 1-norbornyl, 2-norbornyl, 7-norbornyl, 1-adamantyl, 2-adamantyl, 1,2-dihydronaphthyl, 1,2,3,4-tetrahydronaphthyl, 2,3-dihydroindenyl, 1,6-dihydropentalenyl, 1,6a-dihydropentalenyl, yet even more particularly said cycloalkyl is selected from the group consisting of cyclopropyl, cyclopentyl, cyclohexyl and adamantyl. All of the aforementioned cycloalkyl groups, unless specified otherwise, are optionally substituted as detailed in the embodiments of the present invention, i.e. one or more hydrogen atoms are optionally replaced by a substituent as specified in said respective embodiment. Especially particularly, said cycloalkyl groups are unsubstituted unless specified otherwise.

As used herein, a heterocycloalkyl group particularly denotes a non-aromatic mono- or bicyclic completely saturated or partially unsaturated hydrocarbon ring system, wherein one or more of the carbon atoms are replaced by a heteroatom independently selected from the group consisting of N, O, and S. Said heterocycloalkyl does particularly not comprise any aromatic rings. Said heterocycloalkyl is particularly monocyclic. Said heterocycloalkyl is particularly completely saturated. Said heterocycloalkyl particularly comprises a sum of 4 to 10 ring atoms, more particularly a sum of 5 to 10 ring atoms, even more particularly a sum of 5 to 7 ring atoms, yet even more particularly a sum of 5 or 6 ring atoms. Even more particularly said heterocycloalkyl is selected from the group consisting of morpholinyl, piperidinyl, dioxanyl, piperazinyl, thiomorpholinyl, piperidinyl, pyrrolidinyl, tetrahydrofuranyl, isoxazolidinyl, thiomorpholinyl, tetrahydrothiofuranyl and tetrahydropyranyl, more particularly selected from the group consisting of morpholinyl, piperidinyl, dioxanyl, piperazinyl, thiomorpholinyl, piperidinyl, and pyrrolidinyl. All of the aforementioned heterocycloalkyl groups, unless specified otherwise, are optionally substituted as detailed in the embodiments of the present invention, i.e. one or more hydrogen atoms are optionally replaced by a substituent as specified in said respective embodiment. Especially particularly, said heterocycloalkyl groups are unsubstituted unless specified otherwise.

As used herein, a halo or halogen group particularly denotes fluorine, chlorine, bromine or iodine, particularly chlorine or fluorine.

As used herein, an alkoxy group denotes an O-alkyl group, wherein the alkyl group is as defined above. The alkoxy group is particularly selected from the group consisting of methoxy, ethoxy and propoxy, more particularly methoxy. Said aforementioned alkoxy groups are optionally substituted with one or more halogen atoms, particularly with one or more fluorine atoms.

As used herein, an alkylthio group denotes an —S-alkyl group, wherein the alkyl group is as defined above, particularly methylthio. Said aforementioned alkylthio groups are optionally substituted with one or more halogen atoms, particularly with one or more fluorine atoms.

As used herein, an alkoxyalkyl group denotes an alkyl group substituted with an O-alkyl group, wherein the alkyl groups are as defined above, particularly selected from the group consisting of methoxyethyl, ethoxymethyl, methoxymethyl, propoxymethyl and methoxypropyl, more particularly methoxyethyl. Said aforementioned alkoxyalkyl groups are optionally substituted with one or more halogen atoms, particularly with one or more fluorine atoms.

As used herein, an alkylthioalkyl group denotes an alkyl group substituted with an S-alkyl group, wherein the alkyl groups are as defined above, particularly selected from the group consisting of methylthioethyl, ethylthiomethyl, methylthiomethyl, propylthiomethyl and methylthiopropyl, more particularly methylthioethyl. Said aforementioned alkylthioalkyl groups are optionally substituted with one or more halogen atoms, particularly with one or more fluorine atoms.

As used herein, an alkylaminoalkyl group denotes an alkyl group linked to an NH-alkyl group or N-dialkyl group, wherein the alkyl groups are as defined above, particularly selected from the group consisting of methylaminoethyl, ethylaminomethyl, methylaminomethyl, propylaminomethyl and methylaminopropyl, more particularly ethylaminomethyl. Said aforementioned alkylaminoalkyl groups are optionally substituted with one or more halogen atoms, particularly with one or more fluorine atoms.

As used herein, an aryl group particularly denotes an aromatic mono- or bicyclic hydrocarbon ring system, wherein the total number of ring atoms in the aryl group is six to ten, particularly six. Examples of the aryl group are phenyl and naphthyl, more particularly phenyl. All of the aforementioned aryl groups, unless specified otherwise, are optionally substituted as detailed in the embodiments of the present invention, i.e. one or more hydrogen atoms are optionally replaced by a substituent as specified in said respective embodiment. Especially particularly, said aryl groups are unsubstituted unless specified otherwise.

An arylalkyl group, also commonly known as aralkyl group particularly denotes a linear or branched alkyl as defined herein substituted with an aryl group as defined herein. Exemplary arylalkyl groups include styryl, benzyl, phenylethyl, 1-(naphthalen-2-yl)ethyl, particularly the arylalkyl group is styryl or benzyl, more particularly benzyl. Said aforementioned arylalkyl group is optionally substituted, particularly at its aryl part, as defined above for the aryl group.

It is to be understood that the definitions for "alkyl", "aryl", "arylalkyl", "heterocycloalkyl", "cycloalkyl", "heteroaryl", "alkoxy", "alkylthio", "alkoxyalkyl", "alkylthioalkyl", "alkylaminoalkyl", and the like, also refer, insofar as this is applicable, to specific members of said groups as specified in the embodiments of the present invention. For example, the definition for "alkyl" also refers, insofar as this is applicable, to members of said group, such as "$C_{1-6}$-alkyl", "$C_{1-4}$-alkyl", "$C_{1-2}$-alkyl", methyl, ethyl, and the like. This means, for example that the definition that "alkyl" encompasses "alkanyl", "alkenyl" and "alkynyl" applies, mutatis mutandis, to "$C_{1-2}$-alkyl", which consequently encompasses methyl, ethyl, ethenyl and ethynyl.

A nitrogen heteroatom (N) as defined herein, e.g. in the context of "heteroaryl", "heterocycloalkyl" and "heterocycle", may include the N-oxide, in particular where chemically feasible from the viewpoint of stability and/or chemical valence rules.

A sulfur heteroatom (S) as defined herein, e.g. in the context of "heteroaryl", "heterocycloalkyl" and "heterocycle", may include the sulfur oxide and/or the sulfur dioxide, in particular where chemically feasible from the viewpoint of stability and/or chemical valence rules.

As used herein the term "substituted with" or "substituted by" means that one or more hydrogen atoms connected to a carbon atom or heteroatom of a chemical group or entity are exchanged with a substituent group, respectively; e.g. substituted aryl comprises 4-hydroxyphenyl, wherein the H-atom in the 4-position of the phenyl group is exchanged with a hydroxyl group. Said hydrogen atom(s) to be replaced may be attached to a carbon atom or heteroatom, and may be expressly shown in a specific formula, such as for example in an —NH— group, or may not expressly be shown but intrinsically be present, such as for example in the typical "chain" notation which is commonly used to symbolize e.g. hydrocarbons. The skilled person will readily understand that particularly such substituents or substituent patterns are excluded, which lead to compounds which are not stable and/or not accessible via the synthesis methods known in the art. Particular substituent groups may be selected from the group consisting of $C_{1-4}$-alkyl, —OH, halogen, —CO—N(Ri)$_2$, —N(Ri)$_2$, —CO-Ri, —COO-Ri, —N$_3$, —NO$_2$, and —CN, wherein Ri is each independently selected from the group consisting of H and $C_{1-4}$-alkyl.

Unless specified otherwise, references to the compounds according to the present invention include the physiologically functional derivatives, solvates or salts thereof as described herein, as well as to salts of said physiologically functional derivatives, solvates of salts and physiologically functional derivatives, and optionally solvates of salts of physiologically functional derivatives.

As used herein, the term "physiologically functional derivative" of a compound according to the present invention is for instance a prodrug of said compound, wherein at least one of the following groups are derivatized as specified in the following: A carboxylic acid (—COOH) group is derivatized into an ester (having e.g., the formula —COOR8, wherein R8 is selected from the group consisting of —H, alkyl (such as $C_{1-6}$-alkyl), alkoxy (such as $C_{1-6}$-alkoxy), alkoxyalkyl (such as $C_{1-3}$-alkoxy-$C_{1-3}$-alkyl), alkylthio (such as $C_{1-6}$-alkylthio), alklylthioalkyl (such as $C_{1-3}$-alkylthio-$C_{1-3}$-alkyl), alkylaminoalkyl (such as $C_{1-3}$-alkylamino-$C_{1-3}$-alkyl), aryl (such as $C_{6-10}$-aryl), heterocycloalkyl (such as 4- to 10-membered heterocycloalkyl), cycloalkyl (such as $C_{3-10}$-cycloalkyl) and heteroaryl (such as 5- to 10-membered heteroaryl), wherein said alkyl, alkoxy, alkoxyalkyl, alkylthio, alkylthioalkyl, alkylaminoalkyl, aryl, heterocycloalkyl, cycloalkyl and heteroaryl groups are optionally substituted by one or more groups independently selected from the group consisting of $C_{1-4}$-alkyl, —OH, halogen, —CO—N(R9)$_2$, —N(R9)$_2$, —CO—R9, —COO—R9, —N$_3$, —NO$_2$, and —CN, wherein R9 is each independently selected from the group consisting of H and $C_{1-4}$-alkyl); a hydroxyl (—OH) group is derivatized into an ester (having e.g., the formula —COOR8 as defined above); a carboxylic acid is derivatized into an amide (having e.g., the formula —CONH—R8, wherein R8 is as defined above); an amine (—NH$_2$) is derivatized into an amide (having e.g., the formula —CONH—R8, wherein R8 is as defined above); and a hydroxyl group is derivatized into a phosphate ester (having e.g., the formula —OP(O)(OR10)$_2$, wherein R10 is each independently selected from the group consisting of H and $C_{1-4}$-alkyl).

The compounds according to the present invention are to be understood to comprise all tautomeric forms thereof, even if not expressly shown in the formulae described herein, including Formula (I).

The compounds of Formula (I) as defined herein are to be understood to encompass, where applicable, all stereoisomers of said compounds, unless specified otherwise. The term "stereoisomer" as used herein refers to a compound with at least one stereogenic centre, which may be R- or S-configured, as defined by the according IUPAC rules, and encompasses enantiomers and diastereomers as commonly understood by the skilled person. It has to be understood, that in compounds with more than one stereogenic centre, each of the individual stereogenic centres may independently from each other be R- or S-configured. The term "stereoisomer" as used herein also refers to salts of the compounds herein described with optically active acids or bases. The invention further includes all mixtures of the stereoisomers mentioned above independent of the ratio, including the racemates.

In the present invention, the salts of the compounds according to the present invention are particularly pharmaceutically acceptable salts of the compounds according to the present invention. Pharmaceutically acceptable salts are such salts which are usually considered by the skilled person to be suitable for medical applications, e.g. because they are not harmful to subjects which may be treated with said salts, or which give rise to side effects which are tolerable within the respective treatment. Usually, said pharmaceutically acceptable salts are such salts which are considered as acceptable by the regulatory authorities, such as the US Food and Drug Administration (FDA), the European Medicines Agency (EMA), or the Japanese Ministry of Health, Labor and Welfare Pharmaceuticals and Medical Devices Agency (PMDA). However, the present invention in principle also encompasses salts of the compounds according to the present invention which are as such not pharmaceutically acceptable, e.g. as intermediates in the production of the compounds according to the present invention or physiologically functional derivatives thereof, or as intermediates in the production pharmaceutically acceptable salts of the compounds according to the present invention or physiologically functional derivatives thereof. Said salts include water-insoluble and, particularly, water-soluble salts.

In each case, the skilled person can readily determine whether a certain compound according to the present invention or physiologically functional derivative thereof can form a salt, i.e. whether said compound according to the present invention or physiologically functional derivative thereof has a group which may carry a charge, such as e.g. an amino group, a carboxylic acid group, etc.

Exemplary salts of the compounds of the present invention are acid addition salts or salts with bases, particularly pharmaceutically acceptable inorganic and organic acids and bases customarily used in pharmacy, which are either water insoluble or, particularly, water-soluble acid addition salts. Salts with bases may—depending on the substituents of the compounds of the present invention—also be suitable. Acid addition salts may, for example, be formed by mixing a solution of a compound of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Likewise, pharmaceutically acceptable base addition salts may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, arginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, digluconate, dihydrochloride, dodecylsulfate, edetate, edisylate, ethanesulfonate, formate, fumarate, galactate, galacturonate, gluconate, glutamate, glycerophosphate, hemisulfate, heptanoate, hexanoate, hexylresorcinate, hydrobromide, hydrochloride, hydroiodide, 2-hydroxy-ethanesulfonate, hydroxynaphthoate, iodide, isobutyrate, isothionate, lactate, laurate, lauryl sulfate, malate, maleate, malonate, mandelate, methanesulfonate (mesylate), methylsulfate, 2-naphthalenesulfonate, nicotinate, nitrate, oleate, oxalate, palmitate, pantothenate, pectinate, persulfate, 3-phenylpropionate, phosphate/diphosphate, phthalate, picrate, pivalate, polygalacturonate, propionate, salicylate, stearate, sulfate, suberate, succinate, tannate, tartrate, tosylate, undecanoate, valerate, and the like (see, for example, S. M. Berge et al., "Pharmaceutical Salts", J. Pharm. Sci., 66, pp. 1-19 (1977)).

Salts, which are not pharmaceutically acceptable and which can be obtained, for example, as process products during the preparation of the compounds according to the invention on an industrial scale, are also encompassed by the present invention and, if desired, may be converted into pharmaceutically acceptable salts by processes known to the person skilled in the art.

According to expert's knowledge the compounds of the invention as well as their salts may contain, e.g. when isolated in crystalline form, varying amounts of solvents. Included within the scope of the invention are therefore solvates and in particular hydrates of the compounds of the present invention as well as solvates and in particular hydrates of the salts and/or physiologically functional derivatives of the compounds of the present invention. More particularly the invention encompasses hydrates of the compounds, salts and/or physiologically functional derivatives according to the present invention, comprising one, two or one half water molecule, with respect to their stoichiometry.

As used herein, the term "room temperature", "rt" or "r.t." relates to a temperature of from 20 to 25° C., particularly about 22° C., unless specified otherwise.

As used herein, the term "stable" specifies a compound in which the chemical structure is not altered when the compound is stored at a temperature from about −80° C. to about +40° C., particularly from about −80° C. to +25° C. in the absence of light, moisture or other chemically reactive conditions for at least one week, particularly at least one month, more particularly at least six months, even more particularly, at least one year, and/or a compound which under IUPAC standard conditions and in the absence of light, moisture or other chemically reactive conditions maintains its structural integrity long enough to be useful for therapeutic or prophylactic administration to a patient, i.e. at least one week. Compounds which are not stable as described above are particularly not encompassed by the present invention. In particular, such compounds which at IUPAC standard conditions spontaneously decompose within a period of less than one day are regarded as not being stable compounds. The skilled person will readily recognize, based on his general knowledge in his field of expertise, which compounds and which substitution patterns result in stable compounds.

A compound, in particular a compound of Formula (I), is selective for a predetermined target (in particular TLR7) if it is capable of binding to and exerting activity (in particular agonist activity) towards said predetermined target while it is not capable of binding to and exerting agonist activity (in particular agonist and antagonist activity) towards other targets, i.e. exerts no significant agonist activity for other targets in standard assays. According to the invention, a compound of Formula (I) is selective for TLR7 if it is capable of exerting agonist activity towards TLR7 but is not (substantially) capable of exerting agonist activity towards other targets, in particular TLR8. Preferably, a compound, in particular a compound of Formula (I), is selective for TLR7 if the agonist activity for such other targets (in particular TLR8) does not significantly exceed the agonist activity for TLR-unrelated proteins such as LDL receptor, insulin receptor or transferrin receptor or any other specified polypeptide. Preferably, a compound, in particular a compound of Formula (I), is selective for a predetermined target (in particular TLR7) if its agonist activity ($EC_{50}$) for said target is at least 2-fold, 3-fold, 4-fold, 5-fold, 10-fold, 15-fold, 20-fold, 25-fold, 30-fold, 35-fold, 40-fold, 45-fold, 50-fold, 60-fold, 70-fold, 80-fold, 90-fold, 100-fold or $10^3$-fold lower than the its agonist activity for a target for which it is not selective (in particular TLR8). For example, if the $EC_{50}$ of a compound, in particular the $EC_{50}$ of a compound of Formula (I), for the target for which the compound is selective is 1 µM, the $EC_{50}$ for a target for which the compound it is not selective would be at least 2 µM, 3 µM, 4 µM, 5 µM, 10 µM, 15 µM, 20 µM, 25 µM, 30 µM, 35 µM, 40 µM, 45 µM, 50 µM, 60 µM, 70 µM, 80 µM, 90 µM, 100 µM or 1 mM.

It is to be understood that the invention covers all combinations of substituent groups referred to hereinabove. In particular, the invention covers all combinations of particular groups described hereinabove.

Compounds of the invention and salts thereof containing a double bond may exist as E isomers and Z isomers. Both said isomers are included in the invention. The Z isomer is the geometric isomer in which the carbon atoms connected by the double bond each have the two highest ranking groups on the same side of the double bond. The E isomer is the geometric isomer in which the carbon atoms connected by the double bond each have the two highest ranking groups on opposite sides of the double bond.

Some of the compounds and salts according to the invention may exist in different crystalline forms (polymorphs), all of which are within the scope of the invention.

In the following, the term "compound", unless explicitly stated otherwise, is to be understood to encompass physiologically functional derivatives, solvates and salts thereof as defined herein.

As used herein, the term "treatment" includes complete or partial healing of a disease, prevention of a disease, alleviation of a disease or stop of progression of a given disease.

The terms "medical condition", "disease", and "disorder" are used herein interchangeably and refer to any pathological state, including proliferative diseases such as cancer, in particular those pathological states (including cancer forms) described herein. Preferably, a disease is characterized that it can be treated by agonizing TLR7.

As used herein, a "proliferative disease" includes a disease characterized by aberrantly regulated cellular growth, proliferation, differentiation, adhesion, and/or migration. A particular example of proliferative diseases is cancer. By "cancer cell" is meant an abnormal cell that grows by a rapid, uncontrolled cellular proliferation and continues to grow after the stimuli that initiated the new growth cease.

As used herein, the term "medicament" includes the compounds of Formula (I) as described herein, pharmaceutically acceptable salts or physiologically functional derivatives thereof, which are to be administered to a subject in pure form, as well as compositions comprising at least one compound according to the present invention, a pharmaceutically acceptable salt or physiologically functional derivative thereof, which is suitable for administration to a subject.

The compounds according to the present invention and their pharmaceutically acceptable salts and physiologically functional derivatives can be administered to animals, particularly to mammals, and in particular to humans as therapeutics per se, as mixtures with one another or particularly in the form of pharmaceutical preparations or compositions which allow enteral (e.g. oral) or parenteral administration and which comprise as active constituent a therapeutically effective amount of at least one compound according to the present invention, or a salt or physiologically functional derivative thereof, in addition to e.g. one or more components selected from the group consisting of customary adjuvants, pharmaceutically acceptable excipients, carriers, buffers, diluents, solvents, dispersants, emulsifiers, solubilizers, gel formers, ointment bases, antioxidants, preservatives, stabilizers, fillers, binders, thickeners, complexing agents, disintegrating agents, permeation promoters, polymers, lubricants, coating agents, propellants, tonicity adjusting agents, surfactants, colorants, flavorings, sweeteners, dyes and/or other customary pharmaceutical auxiliaries.

The pharmaceutical compositions, medical uses and methods of treatment according to the present invention may comprise more than one compound according to the present invention.

Pharmaceutical compositions comprising a compound according to the present invention, or a pharmaceutically acceptable salt or physiologically functional derivative may optionally comprise one or more further therapeutically active substances which are not compounds of Formula (I) according to the present invention. As used herein, the term "therapeutically active substance" specifies a substance which upon administration can induce a medical effect in a subject. Said medical effect may include the medical effect described herein for the compounds of Formula (I) of the present invention, but may also, in the case of therapeutically active substances which are to be co-administered with the compounds according to the present invention, include other medical substances, such as for example but not exclusively irinotecan, oxaliplatin, gemcitabine, capecitabine, 5-fluorouracil, cetuximab (Erbitux), panitumumab (Vectibix), bevacizumab (Avastin), vincristine, vinblastine, vinorelbine, vindesine, taxol, amsacrine, etoposide, etoposide phosphate, teniposide, actinomycin, anthracyclines, doxorubicin, valrubicin, idarubicin, epirubicin, bleomycin, plicamycin, mitomycin, mechlorethamine, cyclophosphamide, chlorambucil, ifosfamide, bortezomib, imatinib, afatinib, axitinib, bosutinib, cobimetinib, dasatinib, erlotinib, lapatinib, lenvatinib, pazopanib, sorfenib, sunitinib, vemurafenib, and other kinase inhibitors, vorinostat, panobinostat, belinostat, and other histone deacetylase inhibitors.

The term "pharmaceutically acceptable" is well known to the skilled person and particularly means that the respective entity is not harmful to the subject to which the entity or the composition comprising the entity is administered, that said entity is stable and that said entity is chemically compatible (i.e. non-reactive) with other ingredients of the respective pharmaceutical composition.

Medicaments and pharmaceutical compositions according to the present invention, comprising at least one compound according to the present invention or a pharmaceutically acceptable salt or a physiologically functional derivative thereof include those suitable for oral, rectal, bronchial, nasal, topical, buccal, sub-lingual, vaginal or parenteral (including transdermal, intracutaneous, subcutaneous, intramuscular, intrapulmonary, intravascular, intracranial, intraperitoneal, intravenous, intraarterial, intracerebral, intraocular, intrasternal, intracoronary, transurethral, injection or infusion) administration, or those in a form suitable for administration by inhalation or insufflation, including powders and liquid aerosol administration, or by controlled release (e.g. sustained release, pH-controlled release, delayed release, repeat action release, prolonged release, extended release) systems. Suitable examples of controlled release systems include semipermeable matrices of solid hydrophobic polymers containing the compound of the invention, which matrices may be in form of shaped articles, e.g. films or microcapsules or colloidal drug carriers e.g. polymeric nanoparticles, or controlled release solid dosage forms, e.g. core tablets or multi-layer tablets. A particular route of administration in the present invention is intravenous administration.

The compounds according to the present invention may particularly be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents. Alternatively, the active ingredient may be in powder form, obtained by aseptic isolation of sterile solid or by lyophilization from solution, for re-constitution with a suitable vehicle, e.g. sterile, pyrogen-free water, before use.

Any of the other conventional dosage forms may also be used, such as tablets, lozenges, parenteral formulations, syrups, creams, ointments, aerosol formulations, transdermal patches, transmucosal patches and the like. The pharmaceutical compositions according to the present invention can be formulated, for example, into tablets, coated tablets (dragées), pills, cachets, capsules (caplets), granules, powders, suppositories, solutions (e.g. sterile solutions), emulsions, suspensions, ointments, creams, lotions, pastes, oils, gels, sprays and patches (e.g. transdermal therapeutic systems). Additionally, the pharmaceutical compositions can be prepared as, e.g. liposome delivery systems, systems in which the active compound is coupled to monoclonal antibodies and systems in which the active compound is coupled to polymers (e.g. soluble or biodegradable polymers).

Tablets, coated tablets (dragees), pills, cachets, capsules (caplets), granules, solutions, emulsions and suspensions are, e.g. suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g. pH conditions) or by coupling the active compound to a biodegradable polymer.

Administration by inhalation is particularly made by using an aerosol. The aerosol is a liquid-gaseous dispersion, a solid-gaseous dispersion or a mixed liquid/solid-gaseous dispersion.

The particle size of the aerosol particles (solid, liquid or solid/liquid particles) is particularly less than 100 µm, more particularly it is in the range of from 0.5 to 10 µm, even more in particular in the range of from 2 to 6 µm (ID50 value, measured by laser diffraction).

The aerosol may be generated by means of aerosol-producing devices such as dry powder inhalers (DPIs), pressurized metered dose inhalers (PMDIs) and nebulizers. Depending on the kind of the active compound to be administered, the aerosol-producing device can contain the active compound in form of a powder, a solution or a dispersion. The powder may contain, for example, one or more of the following auxiliaries: carriers, stabilizers and fillers. The solution may contain in addition to the solvent, for example, one or more of the following auxiliaries: propellants, solubilizers (co-solvents), surfactants, stabilizers, buffers, tonicity adjusting agents, preservatives and flavorings. The dispersion may contain in addition to the dispersant, for example, one or more of the following auxiliaries: propellants, surfactants, stabilizers, buffers, preservatives and flavorings. Examples of carriers include, but are not limited to, saccharides, e.g. lactose and glucose. Examples of propellants include, but are not limited to, fluorohydrocarbons, e.g. 1,1,1,2-tetrafluoroethane and 1,1,1,2,3,3,3-heptafluoropropane.

Specific aerosol-producing devices which may be used for inhaled administration include, but are not limited to, Cyclohaler®, Diskhaler®, Rotadisk®, Turbohaler®, Autohaler®, Turbohaler®, Novolizer®, Easyhaler®, Aerolizer®, Jethaler®, Diskus®, Ultrahaler® and Mystic® inhalers. The aerosol-producing devices may be combined with spacers or expanders, e.g. Aerochamber®, Nebulator®, Volumatic® and Rondo®, for improving inhalation efficiency.

The production of medicaments or pharmaceutical compositions comprising the compounds according to the present invention and their application can be performed according to methods which are well-known to the medical practitioner.

Pharmaceutically acceptable carriers used in the preparation of a pharmaceutical composition or medicament comprising a compound according to the present invention, a pharmaceutically acceptable salt or physiologically functional derivative thereof, can be either solid or liquid. Solid form pharmaceutical compositions comprising a compound according to the present invention, a pharmaceutically acceptable salt or physiologically functional derivative thereof, include powders, tablets, pills, capsules, sachets, suppositories, and dispersible granules. A solid carrier may comprise one or more components, which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired. The tableting mixture can be granulated, sieved and compressed or direct compressed. Suitable carriers are magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, sachets and lozenges are included. Tablets, powders, capsules, pills, sachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into conveniently sized moulds, allowed to cool, and thereby to solidify. Compositions suitable for vaginal administration may be presented as peccaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

Aqueous solutions suitable for oral administration can be prepared by dissolving the active component in water and adding for example suitable colorants, flavours, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations, which are intended to be converted, shortly before administration, to liquid form preparations for oral administration. Such liquid forms include solutions, suspensions, and emulsions. These preparations may contain, in addition to the active component, for example colorants, flavours, stabilizers, buffers, artificial and natural sweeteners, dispersants, thickeners, solubilizing agents, and the like.

In an embodiment of the present invention the medicament is applied topically, e.g. in the form of transdermal therapeutic systems (e.g. patches) or topical formulations (e.g. liposomes, crèmes, ointment, lotion, gels, dispersion, suspension, spray, solution, foam, powder). This may be suitable to reduce possible side effects and, where appropriate, limit the necessary treatment to those areas affected.

Particularly the medicament may comprise carrier materials or excipients, including but not limited to a lipophilic phase (as for example Vaseline, paraffines, triglycerides, waxes, polyalkylsiloxanes), oils (olive oil, peanut oil, castor oil, triglyceride oil), emulsifier (as for example lecithin, phosphatidylglyceroles, alkyl alcohols, sodium lauryl sulfate, polysorbats, Cholesterol, sorbitan fatty acid ester, polyoxyethylene fatty acid glycerol and -ester, poloxamers), preservatives (for instance benzalkonium chloride, chlorobutanol, parabene or thiomersal), flavouring agents, buffer substances (for example salts of acetic acid, citric acid, boric acid, phosphoric acid, tartaric acid, trometamole or trolamine), solvents (for instance polyethylenglycols, glycerol, ethanol, isopropanol or propyleneglycol) or solubilizers, agents for achieving a depot effect, salts for modifying the osmotic pressure, carrier materials for patches (for instance polypropylene, ethylene-vinylacetat-copolymer, polyacrylates, silicon) or antioxidants (for example ascorbate, tocopherol, butylhydroxyanisole, gallic acid esters or butylhydroxytoluol).

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatine and glycerine or sucrose and acacia; and mouthwashes comprising the active ingredient in a suitable liquid carrier.

Solutions or suspensions may be applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant such as a chlorofluorocarbon (CFC), for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively, the medicament may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form, for example in capsules or cartridges of, e.g., gelatine, or blister packs from which the powder may be administered by means of an inhaler.

In compositions for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are particularly in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, sachet, or lozenge itself, or it can be the appropriate number of any of these in packaged form. Tablets or capsules for oral administration and liquids for intravenous administration and continuous infusion are particular compositions.

Further details on techniques for formulation and administration may be found in $21^{st}$ edition of Remington's Pharmaceutical Sciences (Maack Publishing Co. Easton, Pa.).

The compounds of the present invention may be used in combination with radiation therapy, or in combination with radiation therapy and other active compounds, already known for the treatment of the medical conditions disclosed herein, whereby a favourable additive or amplifying effect is noticed.

To prepare the pharmaceutical preparations, pharmaceutically inert inorganic or organic excipients can be used. To prepare pills, tablets, coated tablets and hard gelatine capsules, for example, lactose, cornstarch or derivatives thereof, talc, stearic acid or its salts, etc. can be used. Excipients for soft gelatine capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The term "therapeutically effective amount" means an amount of the compound sufficient to induce a therapeutic effect, such as activation of TLR7. This may cause cytokine induction, antitumor activity and/or antiviral activity. Although the exact amount of active compound used in a pharmaceutical composition of the invention will vary according to factors known to those skilled in the art, such as the physical and chemical nature of the compound as well as the nature of the carrier and the intended dosing regimen, it is anticipated that the compositions of the invention will contain sufficient active ingredient to provide a suitable dose to a subject. Said dose can vary within wide limits and is to be suited to the individual conditions in each individual case. For the medical applications of the present invention, the appropriate dosage will vary depending on the mode of administration, the particular condition to be treated and the effect desired. In general, however, satisfactory results are achieved at dosage rates of the compound of the present invention of about 1 ng/kg to 100 mg/kg subject body weight, particularly 100 ng/kg to 10 mg/kg, more particularly 1 µg/kg to 1 mg/kg. Doses may be conveniently administered once in two weeks, once or several times per week or up to 2 to 4 times a day in divided doses or in sustained release form.

Surprisingly, the compounds of the present application are selective agonists for TLR7 (especially over TLR8). In particular, the inventors of the present application have found that the double substitution of the amino group NR2R3 of Formula (I) is associated with the TLR7 selectivity, whereas a mono-substitution of the amino group NR2R3 of Formula (I) (i.e., where R2 is H) leads to compounds which are selective for TLR8. Thus, in one embodiment, the compounds of the present application are suitable for the treatment of a medical condition, disease or disorder which can be treated by agonizing TLR7.

The compounds of the present invention are preferably suitable for the treatment of viral disorders and proliferative diseases, in particular hyperproliferative diseases, such as benign and malignant forms of neoplasia, including cancer.

Exemplary types of cancer in the context of the present invention are hepatocarcinoma, adrenocortical carcinoma, AIDS-related cancers including AIDS-related lymphoma, anal cancer, basal cell carcinoma, bile duct cancer, bone cancer, brain tumors including brain stem glioma, cerebellar astrocytoma, cerebral astrocytoma, malignant glioma, ependymoma, medulloblastoma, supratentorial primitive neuroectodermal tumors, visual pathway and hypothalamic glioma, breast cancer, bronchial adenomas/carcinoids, Burkitt's lymphoma, gastrointestinal carcinoma, carcinoma of unknown primary site, central nervous system lymphoma, cervical cancer, chronic myeloproliferative disorders, colon cancer, colorectal cancer, stomach cancer, cutaneous T-cell lymphoma, endometrial cancer, ependymoma, esophageal cancer, extracranial germ cell tumor, extragonadal germ cell tumor, ovarian germ cell tumor, eye cancer including intraocular melanoma and retinoblastoma, gallbladder cancer, gastrointestinal carcinoid tumor, gestational trophoblastic tumor, glioma, childhood brain stem glioma, head and neck cancer, hematologic cancer, adult and childhood (primary) hepatocellular cancer, hypopharyngeal cancer, islet cell or pancreatic cancer, renal cancer, laryngeal cancer, acute lymphoblastic leukemia, adult and childhood acute myeloid leukemia, chronic lymphocytic leukemia, chronic myelogenous leukemia, hairy cell leukemia, lip and oral cavity cancer, liver cancer, lung cancer, including non-small cell lung cancer and small cell lung cancer, Hodgkin's lymphoma, non-Hodgkin's lymphoma, primary central nervous system lymphoma, Waldenstrom's macroglobulinemia, merkel cell carcinoma, mesothelioma, metastatic squamous neck cancer with occult primary site, multiple endocrine neoplasia syndrome, multiple myeloma/plasma cell neoplasm, mycosis fungoides, myelodysplastic syndromes, myelodysplastic myeloproliferative diseases, multiple myeloma, chronic myeloproliferative disorders, nasal cavity and paranasal sinus cancer, nasopharyngeal cancer, neuroblastoma, oral cancer, oropharyngeal cancer, osteosarcoma/malignant fibrous histiocytoma of bone, ovarian cancer, ovarian epithelial cancer, ovarian low malignant potential tumor, pancreatic cancer, parathyroid cancer, penile cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter cancer, transitional cell cancer, rhabdomyosarcoma, salivary gland cancer, Ewing's sarcoma, Kaposi's sarcoma, soft tissue sarcoma, uterine sarcoma, sezary syndrome, skin cancer, including melanoma and non-melanoma skin cancer, small intestine cancer, squamous cell carcinoma, gastric cancer, supratentorial primitive neuroectodermal tumors, testicular cancer, thymoma, thymoma and thymic carcinoma, thyroid cancer, trophoblastic tumor, gestational, endometrial uterine cancer, uterine sarcoma, vaginal cancer, vulvar cancer, and Wilms' tumor.

In a more particular embodiment of the present invention, the compounds of the present invention may be used in the treatment of the following cancer types: Prostate, bladder, kidney (i.e. renal), muscle, ovary, skin, stomach, pancreas, breast, cervix, colon, liver, connective tissue, placenta, bone, brain, uterus, salivary gland, or testes.

Illustrative cancers include, but are not limited to cancer of the breast, bladder, bone, brain, central and peripheral nervous system, colon, endocrine glands, esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva; inherited cancers, retinomblastoma and Wilms' tumor; leukemia, lymphoma, non-Hodgkin's disease, chronic and acute myeloid leukaemia, acute lymphoblastic leukemia, Hodgkin's disease, multiple myeloma and T-cell lymphoma; myelodysplastic syndrome, plasma cell neoplasia, paraneoplastic syndromes, cancers of unknown primary site and AIDS-related malignancies.

Particularly, TLR7 agonists would be used to treat cancers of the skin, breast, colon, stomach, pancreas or kidney. Sensitivity of a given cancer to activation of TLR7 can be assessed by, but not limited to measurement of a decrease in primary or metastatic tumor load (minor, partial or complete regression), alterations in the hemogram, altered hormone or cytokine concentrations in the blood, inhibition of further increase of tumor load, stabilization of the disease in the patient, assessment of biomarkers or surrogate markers relevant for the disease, prolonged overall survival of a patient, prolonged time to disease progression of a patient, prolonged progression-free survival of a patient, prolonged disease-free survival of a patient, improved quality of life of a patient, or modulation of the co-morbidity of the disease (for example, but not limited to pain, cachexia, mobilization, hospitalization, altered hemogram, weight loss, wound healing, fever).

The compounds of the invention can be administered as single therapeutic agent in a treatment regimen, or may be administered in combination with one another and/or with other active agents, including additional anticancer agents, immune response modifiers, antivirals, antibiotics, antipyretics, and the like.

Pharmaceutical compositions according to the present invention may comprise one or more, particularly one or two, more particularly one of the compounds according to the present invention. Likewise, the medical applications of the present invention may involve one or more, particularly one or two, more particularly one of the compounds according to the present invention The pharmaceutical compositions comprising the active compound and at least one auxiliary can be manufactured in a manner known to a person skilled in the art, e.g. by dissolving, mixing, granulating, dragee-making, levigating, emulsifying, encapsulating, entrapping or lyophilizing processes.

In case of topical administration, suitable pharmaceutical formulations are, for example, ointments, creams, lotions, pastes, gels, powders, solutions, emulsions, suspensions, oils, sprays and patches (e.g. transdermal therapeutic systems).

For parenteral modes of administration such as, for example, intravenous, intraarterial, intramuscular, subcutaneous, intracutaneous, intraperitoneal and intrasternal administration, particularly solutions (e.g. sterile solutions, isotonic solutions) are used. They are particularly administered by injection or infusion techniques.

In case of intranasal administration, for example, sprays and solutions to be applied in drop form are particular formulations.

For intraocular administration, solutions to be applied in drop form, gels and ointments are exemplified formulations.

Generally, the pharmaceutical compositions according to the invention can be administered such that the dose of the active compound is in the range customary for activators of TLR7. In particular, a dose in the range of from 0.001 to 200 mg, particularly 0.01 mg to 20 mg, more particularly 0.1 mg to 4 mg and even more particularly 0.2 mg to 2 mg, of the active compound per week in particular based on an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination.

Cytokines that may be induced by the administration of compounds according to the invention generally include interferon (IFN) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, cytokines inhibit virus production and tumor cell growth, making the compounds useful in the treatment of tumors and viral diseases.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of T- and/or B-lymphocytes.

The immune response modifying effects of the compounds make them useful in the treatment of a wide variety of conditions. Because of their ability to induce the production of cytokines such as IFN-α and/or TNF-α, and IL-12, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Type I and Type II; molluscum contagiosum; HIV; CMV; VZV; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis carni, cryptosporidiosis, histoplasmosis, toxoplasmosis, trypanosome infection, and leishmaniasis; and bacterial infections, e.g., tuberculosis, and *Mycobacterium avium*.

The invention also provides a method of treating a viral infection in an animal comprising administering an effective amount of a compound of Formula (I) to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose as indicated above with respect to the activation of TLR7, or a dose of about 100 ng/kg to about 50 mg/kg, particularly about 10 µg/kg to about 5 mg/kg. An amount effective to treat a neoplastic condition is an amount that will cause a reduction in tumor size or in the number of tumor foci. Again, the precise amount will vary according to factors known in the art but is expected to be a dose as indicated above with respect to the activation of TLR7, or a dose of about 100 mg/kg to about 50 mg/kg, particularly about 10 mg/kg to about 5 mg/kg.

The compounds according to the invention can be prepared, for example, as described as follows and according to the following specified reaction steps, or, particularly, in a manner as described by way of example in the following examples.

The compounds according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts of the compounds of Formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

The compounds of Formula (I) according to the invention can be converted into their N-oxides, for example, with the aid of hydrogen peroxide in methanol or with the aid of m-chloroperoxybenzoic acid in dichloromethane. The person skilled in the art is familiar with the reaction conditions for carrying out the N-oxidation.

Pure diastereomers and pure enantiomers of the compounds and salts according to the invention that are present in the form of such stereoisomers can be obtained, e.g. by asymmetric synthesis, by using chiral starting compounds in synthesis and by splitting up enantiomeric and diastereomeric mixtures obtained in synthesis.

Enantiomeric and diastereomeric mixtures can be split up into the pure enantiomers and pure diastereomers by methods known to a person skilled in the art. Particularly, diastereomeric mixtures are separated by crystallization, in particular fractional crystallization, or chromatography. Enantiomeric mixtures can be separated, e.g. by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds which are mentioned in the examples represent particular embodiments of the invention.

As used herein, the term "including", where appropriate, is meant to be understood as including but not limiting.

EXAMPLES

Preparation of the Compounds of the Invention:
General

Abbreviations: $CH_2Cl_2$ for dichloromethane, DMF for N,N-dimethylformamide, DMA for N,N-dimethylacetamide, DMSO for dimethyl sulfoxide, THF for tetrahydrofuran, $CH_3CN$ for acetonitrile, EtOAc for ethyl acetate, MeOH for methanol, EtOH for ethanol, AcOH for acetic acid, $HCO_2H$ for formic acid, HCl for hydrochloric acid, NaOH for sodium hydroxide, LiOH for lithium hydroxide, $NaHCO_3$ for sodium bicarbonate, DIPEA for N,N-diisopropylethylamine or N-ethyl-N-isopropylpropan-2-amine, RT for room temperature, STAB for sodium triacetoxyborohydride, PPA for propionic acid, TBDMS for tert-butyldimethylsilyl, Boc for tert-butyloxycarbonyl, Cbz for benzyloxycarbonyl, Me for methyl, Et for ethyl, HPLC for high pressure liquid chromatography, MS for mass spectroscopy, TLC for thin layer chromatography.

Microwave chemistry was performed using a Biotage® Initiator Robot Sixty system. Unless specified otherwise, all TLC were performed on $SiO_2$ plates (silica gel coated with fluorescent indicator F254) and all preparative reversed phase HPLC/MS purifications were performed on an XTerra RP18 5 µm 19×150 mm column, using a gradient system 0.1% $HCO_2H/H_2O/15 \rightarrow 95\%$ $CH_3CN$. Samples were loaded on the reverse phase column using $DMSO/AcOH/H_2O$ 1/1/1 or $CH_3CN/MeOH/DMF$ 80/15/5. Unless specified otherwise, all HCl, NaOH, KOH or LiOH solutions are aqueous.

The compounds were either characterized via proton NMR in $d_6$-dimethylsulfoxide or d-chloroform on a 300 MHz or 400 MHz NMR instrument (Bruker) and by mass spectroscopy, generally recorded via HPLC/MS in a fast gradient on C18-material and using ESI (electrospray ionization) or APCI (atmospheric-pressure chemical ionization) mode. Values for $[M+H]^+$ or $[M-H]^-$ are those found within the corresponding HPLC/MS chromatogram for the specific compound upon protonation or deprotonation. These values were all found to be within tolerable margins of +/−0.2 towards calculated exact mass values.

The magnetic nuclear resonance spectral properties (NMR) refer to the chemical shifts (δ) expressed in parts per million (ppm). The relative area of the shifts in the $^1H$ NMR spectrum corresponds to the number of hydrogen atoms for a particular functional type in the molecule. The nature of the shift, as regards multiplicity, is indicated as singlet (s), broad singlet (br s), doublet (d), triplet (t), quartet (q), quintuplet (quint.) and multiplet or massif (m).

Preparation of Intermediates and Building Blocks

Scheme 1 synthesis of preparation A-C

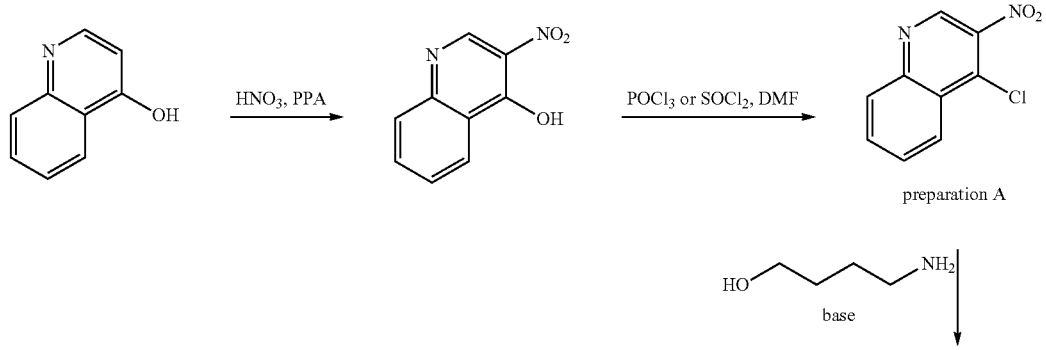

preparation A

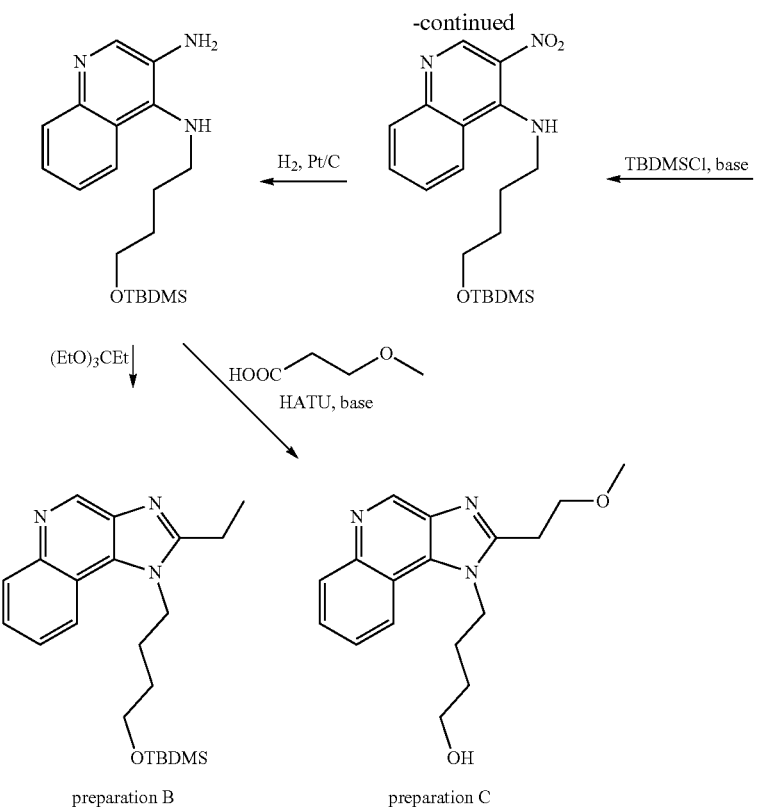

preparation B    preparation C

Preparation A

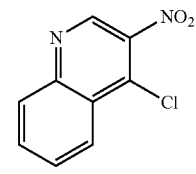

4-Chloro-3-nitroquinoline

Step 1: 4-hydroxyquinoline (250 g, 1.72 mol) was dissolved in propionic acid (200 mL) and the mixture was stirred at 125° C. Nitric acid (158 mL, 3.79 mol, 2.2 eq) was then added dropwise while maintaining the temperature of the reaction at 125° C. After finishing the addition, the reaction mixture was stirred at 125° C. for 60 min and then cooled down to room temperature. The resulting precipitate was filtered off and washed successively with ethanol, water and finally ethanol. The remaining solid was recrystallized from hot ethanol, cooled down, filtered off and dried under reduced pressure to give 252.3 g (77%) of 3-nitroquinolin-4-ol as a beige solid.

$^{1}$H NMR (300 MHz, DMSO-$d_6$) δ 12.96 (br s, 1H), 9.17 (s, 1H), 8.25 (dd, 1H), 7.83-7.68 (m, 2H), 7.51 (m, 1H); MS (ESI+) m/z 191.1 [M+H]$^{+}$

Step 2: POCl$_3$ (661 mL, 7.21 mol, 18.3 eq) was heated at 60° C. and 3-nitroquinolin-4-ol (75 g, 0.39 mol) was added in portions. The resulting suspension was then stirred at 120° C. for 3 h, then cooled down to room temperature and the solvent was removed under reduced pressure. The crude residue was poured on a mixture of ice (1 kg) and CH$_2$Cl$_2$ (500 mL). The aqueous layer was discarded and a solid crystallized from the organic phase during the evaporation. The resulting solid was filtered off and washed with CH$_2$Cl$_2$ to give 40.4 g (50%) of the desired substance as a light beige solid. No further purification.

MS (ESI+) m/z 209.0 211.0 [M+H]$^{+}$

Alternative Conditions for Step 2:

Step 2: A round-bottom flask was charged with a magnetic stir bar, 3-nitroquinolin-4-ol (41.82 g, 219.90 mmol), anhydrous CH$_2$Cl$_2$ (1.05 L) and anhydrous DMF (8.51 mL, 109.95 mmol, 0.5 eq) to get a beige suspension. After addition of thionyl chloride (34.01 g, 285.87 mmol, 1.3 eq) the reaction mixture was refluxed for 5 h. The progress of the reaction was monitored by TLC (petroleum ether/EtOAc 1:1) and by HP LC/MS. The reaction mixture was then cooled down to room temperature and used as such for the next step.

MS (ESI+) m/z 208.9 210.8 [M+H]$^{+}$

Preparation B

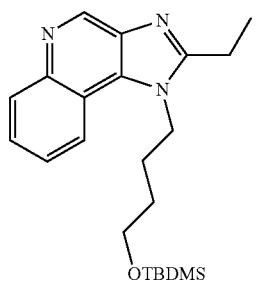 [SMILES: CCc1nc2cnc3ccccc3c2n1CCCCO[Si](C)(C)C(C)(C)C]

1-(4-((tert-Butyldimethylsilyl)oxy)butyl)-2-ethyl-1H-imidazo[4,5-c]quinoline Step 1: 4-Chloro-3-nitroquinoline (preparation A) (15 g, 71.91 mmol) was dissolved in CH$_2$Cl$_2$ (100 mL) and triethylamine (19.99 mL, 143.81 mmol, 2 eq) was added in portions at room temperature. 4-Amino-1-butanol (8.68 mL, 93.48 mmol, 1.3 eq) was added dropwise to the resulting solution (caution! exothermic reaction!) and the reaction mixture was then stirred at reflux for 2 h and subsequently at room temperature overnight. Reaction monitoring by HPLC/MS indicated a complete reaction. The solution was partitioned between CH$_2$Cl$_2$ and saturated aqueous ammonium chloride solution, the layers were separated and the aqueous layer was extracted once with CH$_2$Cl$_2$. The combined organic layers were dried over Na$_2$SO$_4$, filtered and concentrated under reduced pressure to afford 12.8 g (68%) of the desired substance as a dark yellow solid. The material was used without further purification.

$^1$H NMR (300 MHz, DMSO-d$_6$) δ 9.14-9.00 (m, 2H), 8.52 (d, 1H), 7.99-7.74 (m, 2H), 7.58 (m, 1H), 7.28 (br s, 1H), 3.65 (m, 2H), 3.41 (t, 2H), 1.75 (m, 2H), 1.49 (m, 2H); MS (ESI+) m/z 262.1 [M+H]$^+$

Step 2: To a solution of 4-((3-nitroquinolin-4-yl)amino)butan-1-ol (42.8 g, 163.80 mmol) and 4-dimethylaminopyridine (800 mg, 6.54 mmol, 0.04 eq) in chloroform (350 mL) triethylamine (34.2 mL, 245.70 mmol, 1.5 eq) was added dropwise at room temperature followed by addition of tert-butyldimethylsilyl chloride (32.1 g, 212.94 mmol, 1.3 eq) in portions. The resulting mixture was stirred overnight at room temperature. Reaction monitoring by HPLC/MS indicated a complete reaction. The mixture was concentrated under reduced pressure, the residue was suspended in ethyl acetate and then filtered off. The filtrate was partitioned between ethyl acetate and saturated aqueous ammonium chloride solution, the layers were separated and the aqueous layer was extracted once with ethyl acetate. The combined organic layers were dried over Na$_2$SO$_4$, filtered and concentrated under reduced pressure to give 54.7 g (88%) of the title compound as a yellow-green solid. The material was used without further purification.

$^1$H NMR (300 MHz, DMSO-d$_6$) δ 9.14-8.95 (m, 2H), 8.51 (d, 1H), 7.94-7.77 (m, 2H), 7.58 (m, 1H), 3.67 (m, 2H), 3.57 (t, 2H), 1.75 (m, 2H), 1.51 (m, 2H), 0.81 (s, 9H), −0.02 (s, 6H); MS (ESI+) m/z 376.1 [M+H]$^+$

Step 3: A 500 mL PARR vessel (pressure vessel, Parr Instrument GmbH, Germany) was charged with N-(4-((tert-butyldimethylsilyl)oxy)butyl)-3-nitroquinolin-4-amine (35.6 g, 94.79 mmol), 5% platinum on carbon (18.5 g, 4.74 mmol, 0.05 eq) and toluene (150 mL). The vessel was placed on a PARR shaker and pressurized to 50 psi (3.5 kg/cm$^2$) with hydrogen. The reaction was monitored by TLC (CH$_2$Cl$_2$/MeOH 100:5) and was judged to be complete after one hour. The catalyst was removed by filtration through a small pad of CELITE® Hyflo Supercel. The filter cake was washed with toluene (3×100 mL) and the filtrates were combined. The volatiles were removed under reduced pressure to afford 31.65 g (96%) of the desired product as a dark oil.

$^1$H NMR (300 MHz, DMSO-d$_6$) δ 8.36 (s, 1H), 7.99 (m, 1H), 7.72 (m, 1H), 7.33 (m, 2H), 5.31-4.45 (m, 3H), 3.54 (t, 2H), 3.19 (m, 2H), 1.52 (m, 4H), 0.82 (s, 9H), −0.02 (s, 6H); MS (ESI+) m/z 346.1 [M+H]$^+$

Step 4: A round bottom flask was charged with a magnetic stir bar, N$^4$-(4-((tert-butyldimethylsilyl)oxy)butyl)quinoline-3,4-diamine (8.99 g, 26.02 mmol), triethyl orthopropionate (9.17 g, 52.03 mmol, 2 eq) and toluene (76 mL). The reaction was heated at reflux to facilitate removal of the ethanol byproduct until TLC monitoring (benzene/methanol/acetone 1:1:8) and HPLC/MS indicated a complete conversion after 20 h. The reaction was cooled and the volatiles were removed under reduced pressure to afford 9.97 g (quantitative) of 1-(4-((tert-butyldimethylsilyl)oxy)butyl)-2-ethyl-1H-imidazo[4,5-c]quinoline as a thick dark brown oil. The material was used without further purification for the next step.

$^1$H NMR (300 MHz, CDCl$_3$) δ 9.30 (s, 1H), 8.27 (dd, 1H), 8.19 (dd, 1H), 7.64 (m, 2H), 4.57 (t, 2H), 3.71 (t, 2H), 3.01 (q, 2H), 2.06 (m, 2H), 1.73 (m, 2H), 1.55 (t, 3H), 0.87 (s, 9H), 0.04 (s, 6H); MS (ESI+) m/z 384.2 [M+H]$^+$

Preparation C

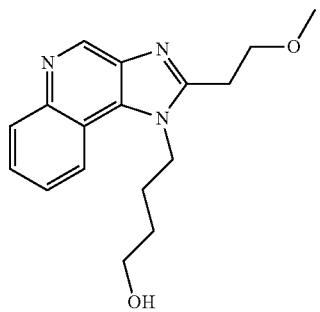 [SMILES: COCCc1nc2cnc3ccccc3c2n1CCCCO]

4-(2-(2-Methoxyethyl)-1H-imidazo[4,5-c]quinolin-1-yl)butan-1-ol

A round-bottom flask was charged with a magnetic stir bar, N$^4$-(4-((tert-butyldimethylsilyl)oxy)butyl)quinoline-3,4-diamine (5.00 g, 14.47 mmol), 3-methoxypropanoic acid (1.81 g, 17.36 mmol, 1.2 eq), 2-(3H-[1,2,3]triazolo[4,5-b]pyridin-3-yl)-1,1,3,3-tetramethylisouronium hexafluorophosphate(V) (HATU, 6.60 g, 17.36 mmol, 1.2 eq), N-ethyl-N-isopropylpropan-2-amine (DIPEA, 2.24 g, 17.36 mmol, 1.2 eq) and anhydrous 1-methyl-2-pyrrolidone (NMP, 60 mL). The resulting solution was stirred at 120° C. until TLC monitoring (benzene/methanol/acetone 1:1:8) indicated complete reaction after 20 h. The mass of the desired product was detected by HPLC/MS. The reaction mixture was then diluted with the tenfold amount of water and extracted with ethyl acetate using a liquid-liquid extractor. The organic layer was concentrated under reduced pressure and the crude substance was purified by flash chromatography on silica (CH$_2$Cl$_2$/MeOH 95:5 to 90:10) to afford 9.48 g (quantitative, still containing impurities) of a reddish-brown oil. The material was used without further purification for the next step.

MS (ESI+) m/z 300.0 [M+H]$^+$

Scheme 2 synthesis of preparation D

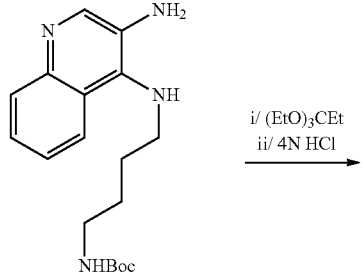

-continued

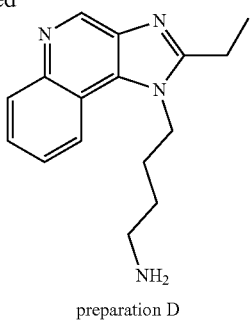

preparation D

Preparation D

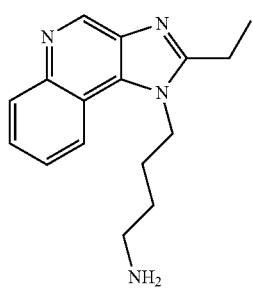 [SMILES: CCc1nc2cnc3ccccc3c2n1CCCCN]

4-(2-Ethyl-1H-imidazo[4,5-c]quinolin-1-yl)butan-1-amine

A round bottom flask was charged with a magnetic stir bar, commercially available tert-butyl (4-((3-aminoquinolin-4-yl)amino)butyl)carbamate (3.00 g, 9.08 mmol), triethyl orthopropionate (3.20 g, 18.16 mmol, 2 eq) and toluene (50 mL). The reaction was heated at reflux to facilitate removal of the ethanol byproduct until TLC monitoring (CHCl$_3$/MeOH/32% ammonia solution 90:9:1) and HPLC/MS indicated a complete conversion after 24 h. The reaction mixture was then allowed to cool down to room temperature and concentrated under reduced pressure. The residue was dissolved in anhydrous 1,4-dioxane (50 mL), 4N HCl/1,4-dioxane (50 mL) was added and the reaction stirred at room temperature overnight. The mixture was then concentrated in vacuo and the residue was dissolved in saturated sodium bicarbonate solution (100 mL), frozen and lyophilized. The lyophilisate was extracted with absolute ethanol (3×100 mL). The combined extracts were filtered and concentrated under reduced pressure to get 2.146 g (88%) of 4-(2-ethyl-1H-imidazo[4,5-c]quinolin-1-yl)butan-1-amine as a reddish-yellow oil.

$^1$H NMR (300 MHz, CDCl$_3$) δ 9.30 (s, 1H), 8.28 (m, 1H), 8.18 (m, 1H), 7.64 (m, 2H), 4.55 (t, 2H), 3.01 (q, 2H), 2.79 (t, 2H), 2.02 (m, 2H), 1.72-1.49 (m, 5H); MS (ESI+) m/z 269.4 [M+H]$^+$

Scheme 3 synthesis of preparation E

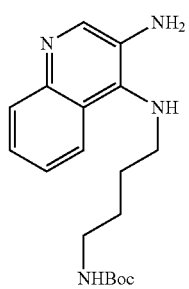

i/ Cbz-N-Et-Gly-OH
HATU, base i/ Boc$_2$O, base
ii/ NH$_2$NH$_2$·H$_2$O
iii/ 4N HCl

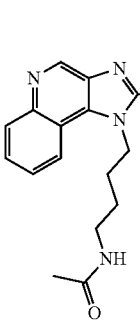

+ preparation E

Preparation E

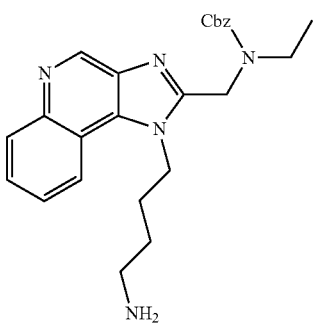 [SMILES: CCN(Cc1nc2cnc3ccccc3c2n1CCCCN)C(=O)OCc1ccccc1]

Benzyl((1-(4-aminobutyl)-1H-imidazo[4,5-c]quinolin-2-yl)methyl)(ethyl)carbamate

Step 1: A round-bottom flask was charged with a magnetic stir bar, commercially available tert-butyl (4-((3-aminoquinolin-4-yl)amino)butyl)carbamate (40.00 g, 121.05 mmol), 2-{[(benzyloxy)carbonyl](ethyl)amino}acetic acid (Cbz-N-Et-Gly-OH, 34.46 g, 145.27 mmol, 1.2 eq), 2-(3H-[1,2,3]triazolo[4,5-b]pyridin-3-yl)-1,1,3,3-tetramethylisouronium hexafluorophosphate(V) (HATU, 55.23 g, 145.27 mmol, 1.2 eq), triethylamine (36.75 g, 363.16 mmol, 3 eq), 4-dimethylaminopyridine (1.48 g, 12.11 mmol, 0.1 eq) and anhydrous DMF (800 mL) to give a reddish-yellow solution. The reaction mixture was stirred at room temperature until TLC monitoring (CHCl$_3$/MeOH/32% ammonia solution 140:9:1) and HPLC/MS indicated an almost complete conversion after about 10-12 hours. The solvent was evaporated under reduced pressure, the residue was then dissolved in ethyl acetate (500 mL) and washed with water (3×300 mL). The organic layer was dried over Na$_2$SO$_4$, filtered and concentrated under reduced pressure. The crude dark-yellow intermediate was dissolved in glacial acetic acid (400 mL) and the mixture was heated at reflux for 36 h and monitored by HPLC/MS. The reaction mixture was then concentrated by distillation of the toluene-acetic acid azeotrope at reduced pressure and the residue was suspended in saturated aqueous NaHCO$_3$ (200 mL) and filtered off. The filtrate was extracted with chloroform (3×200 mL), the aqueous layer was adjusted to pH 10-11 by addition of 3M NaOH and extracted with chloroform (9×100 mL). The filter cake and the aqueous layer were discarded. The collected organic layers were washed successively with brine (400 mL) and dried over Na$_2$SO$_4$, filtered off and concentrated under reduced pressure. The residue was purified by flash chromatography on silica gel (CHCl$_3$/MeOH/32% ammonia solution 290:9:1) to give 13.82 g (24%) of benzyl ((1-(4-acetamidobutyl)-1H-imidazo[4,5-c]quinolin-2-yl)methyl)(ethyl)carbamate as a reddish-yellow oil and 8.75 g (~80% pure, 16%) of benzyl ((1-(4-aminobutyl)-1H-imidazo[4,5-c]quinolin-2-yl)methyl)(ethyl)carbamate as a reddish-yellow oil.

$^1$H NMR (300 MHz, CDCl$_3$) δ 9.28 (s, 1H), 8.28 (dd, 1H), 8.08 (dd, 1H), 7.67 (m, 2H), 7.43-7.28 (m, 5H), 6.00 (br s, 1H), 5.22 (s, 2H), 4.92 (s, 2H), 4.61 (br s, 2H), 3.43 (q, 2H), 3.22 (m, 2H), 1.94 (s, 3H), 1.92-1.59 (m, 4H), 1.10 (t, 3H); MS (ESI+) m/z 474.2 [M+H]$^+$

Step 2: A round-bottom flask was charged with a magnetic stir bar, a reflux condenser, benzyl ((1-(4-acetamidobutyl)-1H-imidazo[4,5-c]quinolin-2-yl)methyl)(ethyl)carbamate (13.20 g, 27.87 mmol), 4-dimethylaminopyridine (0.68 g, 5.57 mmol, 0.2 eq) and tetrahydrofuran (420 mL) to give a yellow solution. Di-tert-butyl dicarbonate (18.25 g, 83.62 mmol, 3 eq) was added and the mixture was heated to reflux for 16 h. TLC monitoring (CHCl$_3$/MeOH/32% ammonia solution 140:9:1) and HPLC/MS indicated an incomplete conversion. Additional di-tert-butyl dicarbonate (6.08 g, 27.87 mmol, 1 eq) and a further refluxing for 2 h were necessary to obtain a complete conversion. Methanol (420 mL) and hydrazine monohydrate (11.16 g, 222.98 mmol, 8 eq) were added and the reaction mixture was stirred at room temperature overnight. Additional hydrazine monohydrate (2.79 g, 55.75 mmol, 2 eq) and a further stirring overnight were necessary to obtain a complete conversion according to TLC (CHCl$_3$/MeOH/32% ammonia solution 140:9:1) and HPLC/MS. The reaction mixture was then poured into dichloromethane (800 mL), washed successively with 1N HCl (250 mL), aqueous 10% copper(II) sulfate solution (250 mL) and saturated aqueous NaHCO$_3$ (250 mL), dried over MgSO$_4$, filtered off and concentrated under reduced pressure. The residue was then dissolved in 1,4-dioxane (400 mL) and treated 4N HCl/1,4-dioxane (200 mL) at room temperature for 60 min until TLC monitoring (CHCl$_3$/MeOH/32% ammonia solution 140:9:1) indicated complete reaction. The reaction mixture was next diluted with water (600 mL), the pH was adjusted to 10-11 by addition of 3M NaOH and the mixture was extracted with CH$_2$Cl$_2$ (3×250 mL). The combined organic layers were concentrated under reduced pressure. The residue was pooled with the aqueous layer and concentrated by distillation of the sec-butanol-water azeotrope at reduced pressure. The crude was extracted with dichloromethane containing 10% absolute ethanol (2×500 mL). The combined organic layers were dried over MgSO$_4$, filtered off and concentrated in vacuo to give 12.80 g (80-90% pure, quantitative) of benzyl ((1-(4-aminobutyl)-1H-imidazo[4,5-c]quinolin-2-yl)methyl)(ethyl)carbamate as a dark yellow oil. The substance was used for the next step without any further purification.

MS (ESI+) m/z 432.2 [M+H]$^+$

Scheme 4 synthesis of Example 1 (for illustrative purposes)

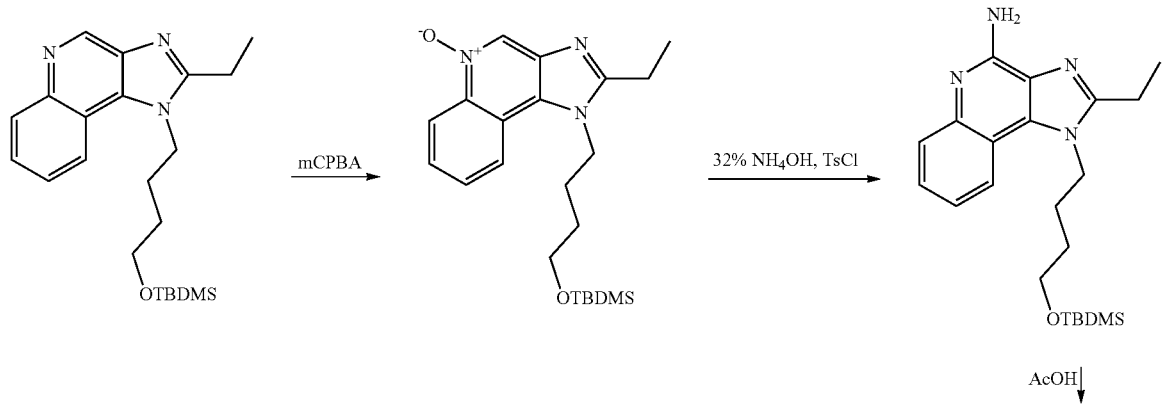

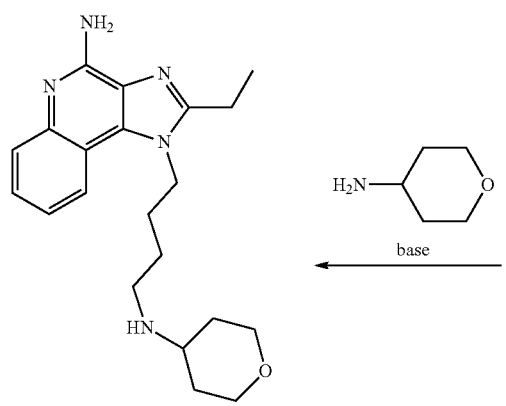 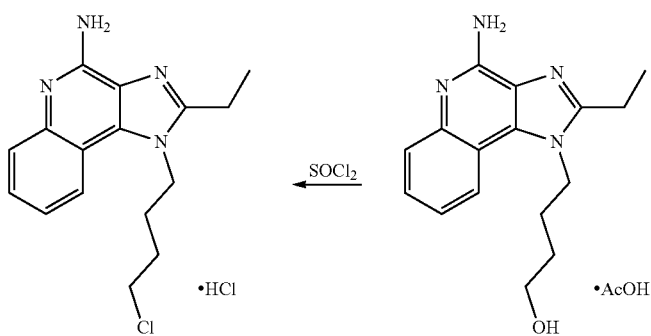

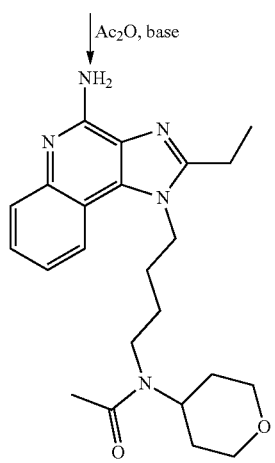

Example 1

Example 1 (For Illustrative Purposes)

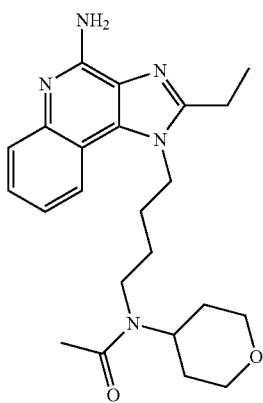 [SMILES: CCc1nc2c(N)nc3ccccc3c2n1CCCCN(C(C)=O)C1CCOCC1]

N-(4-(4-Amino-2-ethyl-1H-imidazo[4,5-c]quinolin-1-yl)butyl)-N-(tetrahydro-2H-pyran-4-yl)acetamide Step 1: A round bottom flask was charged with a magnetic stir bar, 1-(4-((tert-butyldimethylsilyl)oxy)butyl)-2-ethyl-1H-imidazo[4,5-c]quinoline (see preparation B) (9.97 g, 25.99 mmol) and chloroform (130 mL). Solid 3-chlorobenzoperoxoic acid (4.93 g, 28.59 mmol, 1.1 eq) was added in portions to the solution over 15 minutes and the mixture was stirred at room temperature for 1 hour. TLC monitoring (benzene/methanol/acetone 1:1:8) and HPLC/MS indicated a complete consumption of the starting material after further addition of 3-chlorobenzoperoxoic acid (1.35 g, 7.80 mmol, 0.3 eq) and a further 30 minutes of stirring. The reaction mixture was then partitioned between chloroform and aqueous saturated sodium bicarbonate solution and the layers were separated. The organic phase was washed successively with aqueous saturated sodium bicarbonate solution and brine, dried over $Na_2SO_4$, filtered off and concentrated under reduced pressure to afford 9.64 g (93%) of 1-(4-((tert-butyldimethylsilyl)oxy)butyl)-2-ethyl-1H-imidazo[4,5-c]quinoline 5-oxide as a beige-brown solid. The material was used without further purification for the next step.

MS (ESI+) m/z 400.1 [M+H]$^+$

Step 2: A round bottom flask was charged with a magnetic stirrer bar, 1-(4-((tert-butyldimethylsilyl)oxy)butyl)-2-ethyl-1H-imidazo[4,5-c]quinoline 5-oxide (9.64 g, 24.12 mmol), chloroform (100 mL) and ammonia solution (32%, 100 mL). 4-Methylbenzene-1-sulfonyl chloride (5.52 g, 28.95 mmol, 1.2 eq) was added to the biphasic mixture in one portion and the reaction was vigorously stirred at room temperature until TLC monitoring (benzene/methanol/acetone 1:1:8) and HPLC/MS indicated a complete conversion after 2 h. The mixture was then partitioned between chloroform (150 mL) and brine (250 mL). The organic layer was separated from the aqueous layer and washed with brine (2×150 mL), dried over Na$_2$SO$_4$, filtered and evaporated under reduced pressure to afford 8.57 g (89%) of 1-(4-((tert-butyldimethylsilyl)oxy)butyl)-2-ethyl-1H-imidazo[4,5-c]quinolin-4-amine as a rust-brown solid. The material was used without further purification for the next step.

MS (ESI+) m/z 399.1 [M+H]$^+$

Step 3: A round bottom flask was charged with a magnetic stirrer bar, 1-(4-((tert-butyldimethylsilyl)oxy)butyl)-2-ethyl-1H-imidazo[4,5-c]quinolin-4-amine (8.57 g, 21.50 mmol), tetrahydrofuran (90 mL), water (90 mL) and acetic acid (270 mL) and the resulting reddish solution was stirred at 60° C. until TLC monitoring (benzene/methanol/acetone 1:1:8) and HPLC/MS indicated a complete conversion after 16 h. The reaction mixture was then allowed to cool down to 0° C. and adjusted to pH 8 with a dropwise addition of 10M NaOH (~333 mL). The aqueous layer was extracted with a mixture of ethyl acetate and ethanol (5×200 mL). The organic layers were combined, concentrated under reduced pressure and the resulting solid was extracted with DMF to get rid of sodium acetate salts. The extract was concentrated in vacuo to afford 6.78 g (92%) of 4-(4-amino-2-ethyl-1H-imidazo[4,5-c]quinolin-1-yl)butan-1-ol acetate as a beige-brown solid.

MS (ESI+) m/z 285.1 [M+H]$^+$

Step 4: Thionyl chloride (7.04 g, 59.20 mmol, 3 eq) was added to a suspension of 4-(4-amino-2-ethyl-1H-imidazo[4,5-c]quinolin-1-yl)butan-1-ol acetate (6.78 g, 19.73 mmol) in dichloroethane (300 mL) and the yellow-beige mixture was stirred at room temperature overnight. HPLC/MS monitoring showed a complete conversion. The mixture was cooled down to 0° C. and methanol (25 mL) was slowly added. The volatiles were removed under reduced pressure and the residue washed successively with acetone and diethylether and dried under high vacuum to get 5.021 g (75%) of 1-(4-chlorobutyl)-2-ethyl-1H-imidazo[4,5-c]quinolin-4-amine hydrochloride as a yellow beige solid. The washing solutions were filtered off and the precipitate, washed successively with acetone and diethylether and dried under high vacuum to get 0.401 g (6%) of a second fraction of the product.

$^1$H NMR (300 MHz, DMSO-d$_6$) δ 13.88 (s, 1H), 8.74 (br s, 2H), 8.26 (d, 1H), 7.83 (d, 1H), 7.72 (t, 1H), 7.58 (t, 1H), 4.62 (m, 2H), 3.71 (m, 2H), 3.02 (q, 2H), 1.94 (m, 4H), 1.41 (t, 3H); MS (ESI+) m/z 303.1 [M+H]$^+$

Step 5: To a suspension of 1-(4-chlorobutyl)-2-ethyl-1H-imidazo[4,5-c]quinolin-4-amine hydrochloride (150 mg, 0.442 mmol) in anhydrous DMA (4 mL), DIPEA (229 mg, 1.79 mmol, 4 eq) and tetrahydro-2H-pyran-4-amine (134 mg, 1.326 mmol, 3 eq) were added and the mixture was stirred at 100° C. for 4.5 days. HPLC/MS monitoring showed formation of the desired substance. The mixture was concentrated in vacuo and the residue was purified by preparative HPLC to afford 67 mg (42%) of 2-ethyl-1-(4-((tetrahydro-2H-pyran-4-yl)amino)butyl)-1H-imidazo[4,5-c]quinolin-4-amine as a yellow-beige solid.

$^1$H NMR (300 MHz, DMSO-d$_6$) δ 8.06 (dd, 1H), 7.62 (dd, 1H), 7.42 (ddd, 1H), 7.26 (ddd, 1H), 6.53 (br s, 2H), 4.54 (t, 2H), 3.84 (m, 2H), 3.25 (dd, 2H), 2.96 (q, 2H), 2.85 (m, 1H), 2.75 (t, 2H), 1.93-1.73 (m, 4H), 1.63 (m, 2H), 1.38 (t, 3H), 1.33 (m, 2H); MS (ESI+) m/z 368.1 [M+H]$^+$ Step 6: A pear-shaped flask was charged with a magnetic stir bar, 2-ethyl-1-(4-((tetrahydro-2H-pyran-4-yl)amino)butyl)-1H-imidazo[4,5-c]quinolin-4-amine (43 mg, 0.117 mmol; prepared by ion exchange chromatography on Agilent StratoSpheres PL-HCO$_3$ MP resin to remove traces of formic acid), 2M NaOH (88 µL, 0.176 mmol, 1.5 eq) and water (1 mL) to give a pale yellow suspension. After addition of acetic anhydride (22 µL, 0.234 mmol, 2 eq), the resulting mixture was stirred at RT until TLC monitoring (CH$_2$Cl$_2$/MeOH 9:1) and HPLC/MS indicated a complete consumption of the starting material after two days. The reaction mixture was then directly subjected to preparative TLC (SiO$_2$ 20 cm$^2$, CH$_2$Cl$_2$/MeOH 9:1) to afford 10.4 mg (22%) of an off-white solid.

$^1$H NMR (300 MHz, CD$_3$OD) (mixture of rotamers) δ 8.09 (m, 1H), 7.71 (d, 1H), 7.50 (t, 1H), 7.35 (t, 1H), 4.59 (quint. 2H), 4.28 (m, 0.4H), 4.01-3.77 (m, 2.6H), 3.42 (m, 2H), 3.28 (m, 2H), 3.03 (m, 2H), 2.11 (s, 1.8H), 2.07 (s, 1.2H), 2.02-1.54 (m, 8H), 1.53-1.43 (m, 3H); MS (ESI+) m/z 410.1 [M+H]$^+$ Scheme 5 synthesis of Example 2 and 4 (for illustrative purposes)

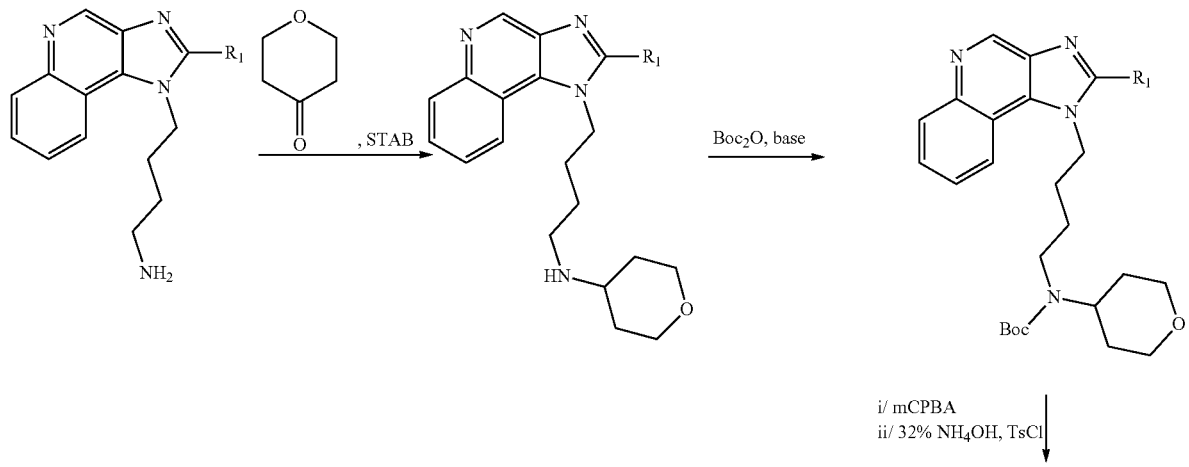

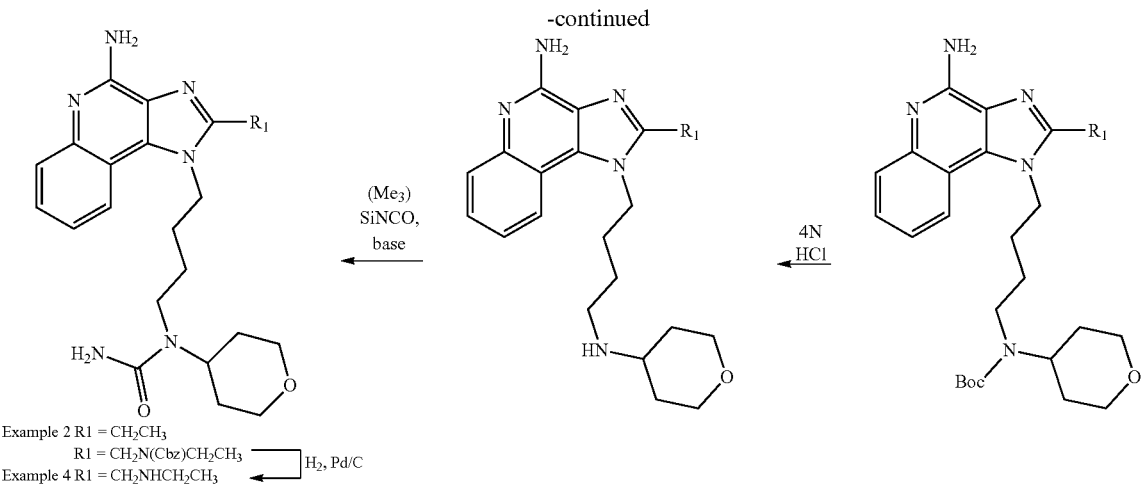

Example 2 R1 = CH₂CH₃
R1 = CH₂N(Cbz)CH₂CH₃
Example 4 R1 = CH₂NHCH₂CH₃   H₂, Pd/C Example 2 (For Illustrative Purposes)

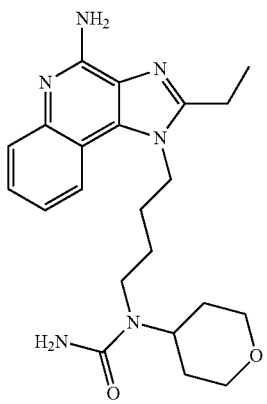 [SMILES: CCc1nc2c(N)nc3ccccc3c2n1CCCCN(C(N)=O)C1CCOCC1]

1-(4-(4-Amino-2-ethyl-1H-imidazo[4,5-c]quinolin-1-yl)butyl)-1-(tetrahydro-2H-pyran-4-yl)urea Step 1: A round-bottomed flask was charged with a magnetic stir bar, 4-(2-ethyl-1H-imidazo[4,5-c]quinolin-1-yl)butan-1-amine (see preparation D) (1.430 g, 5.329 mmol), tetrahydro-4H-pyran-4-one (533 mg, 5.329 mmol, 1 eq) and 1,2-dichloroethane (30 mL). After addition of sodium triacetoxyborohydride (1.581 g, 7.460 mmol, 1.4 eq) and acetic acid (320 mg, 5.329 mmol, 1 eq), the mixture was stirred at room temperature overnight. Reaction monitoring by HPLC/MS and TLC (CHCl₃/MeOH/32% ammonia solution 90:9:1) showed a complete consumption of the starting material. The reaction mixture was quenched with 1M NaOH (30 mL), the layers were separated and the aqueous phase was extracted with 1,2-dichloroethane (3×30 mL). The combined organic layers were concentrated in vacuo and the oily residue was dried by distillation of the toluene-water azeotrope at reduced pressure and subsequently in high vacuum. The crude was subjected to column chromatography on silica gel (CHCl₃/MeOH/32% ammonia solution 440:9:1 to 190:9:1) to get 1.652 g (88%) of N-(4-(2-ethyl-1H-imidazo[4,5-c]quinolin-1-yl)butyl)tetrahydro-2H-pyran-4-amine as a dark yellow oil.

$^1$H NMR (300 MHz, CDCl₃) δ 9.30 (s, 1H), 8.27 (m, 1H), 8.19 (m, 1H), 7.64 (m, 2H), 4.55 (t, 2H), 3.96 (m, 2H), 3.37 (m, 2H), 3.00 (q, 2H), 2.72 (t, 2H), 2.63 (m, 1H), 2.03 (m, 2H), 1.79 (m, 2H), 1.68 (m, 2H), 1.54 (t, 3H), 1.39 (m, 2H); MS (ESI+) m/z 353.4 [M+H]⁺

Step 2: A round bottom flask was charged with a magnetic stir bar, N-(4-(2-ethyl-1H-imidazo[4,5-c]quinolin-1-yl)butyl)tetrahydro-2H-pyran-4-amine (824 mg, 2.338 mmol), triethylamine (473 g, 4.675 mmol, 2 eq) and 1,2-dichloroethane (15 mL) to give a yellow solution. After addition of di-tert-butyl dicarbonate (510 mg, 2.338 mmol, 1 eq) the reaction mixture was stirred at room temperature overnight. Reaction monitoring by HPLC/MS and TLC (CHCl₃/MeOH/32% ammonia solution 90:9:1) showed a complete consumption of the starting material. The reaction mixture was washed with 5% citric acid (15 mL) and brine (15 mL). The organic layer was dried over Na₂SO₄, filtered and concentrated under reduced pressure to yield 1.006 g (95%) of tert-butyl (4-(2-ethyl-1H-imidazo[4,5-e]quinolin-1-yl)butyl)(tetrahydro-2H-pyran-4-yl)carbamate as a red-brown oil.

$^1$H NMR (300 MHz, CDCl₃) δ 9.30 (s, 1H), 8.28 (dd, 1H), 8.13 (dd, 1H), 7.64 (m, 2H), 4.54 (t, 2H), 3.98 (m, 2H), 3.39 (t, 2H), 3.16 (m, 2H), 3.00 (q, 2H), 1.95 (m, 2H), 1.82-1.49 (m, 9H), 1.40 (s, 9H); MS (ESI+) m/z 453.6 [M+H]⁺

Step 3: A round bottom flask was charged with a magnetic stir bar, tert-butyl (4-(2-ethyl-1H-imidazo[4,5-c]quinolin-1-yl)butyl)(tetrahydro-2H-pyran-4-yl)carbamate (1.002 g, 2.214 mmol) and dichloromethane (15 mL) to give a dark-yellow solution. Solid 3-chlorobenzoperoxoic acid (0.955 g, 5.535 mmol, 2.5 eq) was added in portions to the solution over the course of 5 minutes and the reaction was stirred at room temperature until TLC monitoring (CHCl₃/MeOH/32% ammonia solution 140:9:1) and HPLC/MS indicated a complete reaction after 3 h. Ammonia solution (32%, 15 mL) was added to the solution followed by p-toluenesulfonyl chloride (1.013 g, 5.313 mmol, 2.4 eq) and the biphasic mixture was vigorously stirred at room temperature overnight. Reaction monitoring by HPLC/MS and TLC (CHCl₃/MeOH/32% ammonia solution 140:9:1) showed a complete consumption of the starting material. The two layers were separated and the aqueous phase was extracted with CH₂Cl₂ (50 mL). The combined organic layers were washed with sodium bicarbonate solution (saturated sodium bicarbonate solution:water=1:1, 1×50 mL) and concentrated in vacuo. The residue was subjected to column chromatography on silica gel (CHCl₃/MeOH/32% ammonia solution 540:9:1) to give 613 mg (59%) of tert-butyl (4-(4-amino-2-ethyl-1H-imidazo[4,5-c]quinolin-1-yl)butyl)(tetrahydro-2H-pyran-4-yl)carbamate as a yellow-beige solid.

¹H NMR (300 MHz, CDCl₃) (mixture of rotamers) δ 7.90 (dd, 1H), 7.82 (dd, 1H), 7.50 (ddd, 1H), 7.30 (ddd, 1H), 5.42 (br s, 2H), 4.46 (t, 2H), 3.98 (m, 2.5H) 3.39 (t, 2H), 3.18 (2.4H), 2.94 (q, 2H), 1.93 (m, 2H), 1.82-1.53 (m, 6H), 1.48 (t, 3H), 1.41 (s, 9H); MS (ESI+) m/z 468.3 [M+H]⁺

Step 4: A round-bottom flask was charged with a magnetic stir bar, tert-butyl (4-(4-amino-2-ethyl-1H-imidazo[4,5-c]quinolin-1-yl)butyl)(tetrahydro-2H-pyran-4-yl)carbamate (602 mg, 1.287 mmol) and anhydrous 1,4-dioxane (10 mL) to give a yellow-beige suspension. 4N HCl/1,4-dioxane (10 mL) was added and the reaction stirred at room temperature for 2.5 days. Reaction monitoring by HPLC/MS and TLC (CHCl₃/MeOH/32% ammonia solution 140:9:1) showed a complete consumption of the starting material. The resulting precipitate was filtered off, washed with anhydrous Et₂O (3×20 mL) and deionized via ion-exchange chromatography on an Agilent StratoSpheres PL-HCO₃ MP SPE cartridge (a polymer supported quaternary amine (HCO₃⁻ form) device for the removal of TFA or HCl salts by solid phase extraction (SPE)—Agilent, order No. PL3540-G603) to isolate the free amine. The crude substance was purified by flash chromatography on silica gel (CHCl₃/MeOH/32% ammonia solution 140:9:1) to get 363 mg of 2-ethyl-1-(4-((tetrahydro-2H-pyran-4-yl)amino)butyl)-1H-imidazo[4,5-c]quinolin-4-amine as a yellow-beige solid.

¹H NMR (300 MHz, CDCl₃) δ 7.97 (d, 1H), 7.82 (d, 1H), 7.50 (dt, 1H), 7.31 (dt, 1H), 5.39 (br s, 2H), 4.48 (t, 2H), 3.95 (m, 2H), 3.37 (dt, 2H), 2.94 (q, 2H), 2.70 (t, 2H), 2.63 (m, 1H), 2.01 (m, 2H), 1.79 (m, 2H), 1.65 (m, 2H), 1.48 (t, 3H), 1.37 (m, 2H); MS (ESI+) m/z 368.2 [M+H]⁺

Step 5: A round-bottom flask was charged with a magnetic stir bar, 2-ethyl-1-(4-((tetrahydro-2H-pyran-4-yl)amino)butyl)-1H-imidazo[4,5-c]quinolin-4-amine (367 mg, 0.999 mmol), triethylamine (101 mg, 0.999 mmol, 1 eq) and anhydrous chloroform (5 mL). The yellow solution was cooled to 0-4° C. in an ice bath, trimethylsilyl isocyanate (127 mg, 1.099 mmol, 1.1 eq) was added and the mixture was stirred at room temperature. Reaction monitoring by HPLC/MS and TLC (CHCl₃/MeOH/32% ammonia solution 90:9:1) showed an incomplete consumption of the starting material after 1 h. Additional trimethylsilyl isocyanate (127 mg, 1.099 mmol, 1 eq) was added every 30 min over the next 5 h to obtain a complete conversion. The reaction mixture was concentrated under reduced pressure and the residue was purified by preparative TLC (SiO₂ 20 cm², CHCl₃/MeOH/32% ammonia solution 90:9:1) to give 273 mg (67%) of an off-white solid.

¹H NMR (300 MHz, DMSO-d₆) δ 8.02 (dd, 1H), 7.61 (dd, 1H), 7.41 (ddd, 1H), 7.25 (ddd, 1H), 6.41 (br s, 2H), 5.76 (br s, 2H), 4.49 (t, 2H), 3.96 (m, 1H), 3.85 (dd, 2H), 3.29 (m, 2H), 3.07 (t, 2H), 2.95 (q, 2H), 1.79 (m, 2H), 1.71-1.53 (m, 4H), 1.44 (m, 2H), 1.38 (t, 3H); MS (ESI+) m/z 411.2 [M+H]⁺

Example 4 (For Illustrative Purposes)

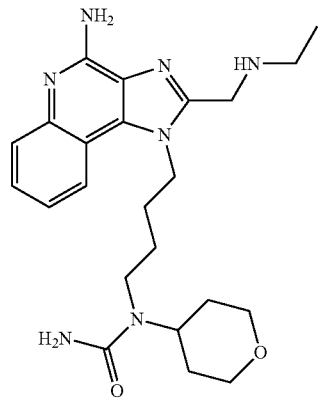 [SMILES: CCNCc1nc2c(N)nc3ccccc3c2n1CCCCN(C(N)=O)C1CCOCC1]

1-(4-(4-Amino-2-((ethylamino)methyl)-1H-imidazo[4,5-c]quinolin-1-yl)butyl)-1-(tetrahydro-2H-pyran-4-yl)urea Steps 1-5: Prepared as described in Example 2, using benzyl ((1-(4-aminobutyl)-1H-imidazo[4,5-c]quinolin-2-yl)methyl)(ethyl)carbamate (see preparation E) (3.5 g, 8.11 mmol) as starting material to yield 249 mg (5% overall yield for 5 steps) of benzyl ((4-amino-1-(4-(1-(tetrahydro-2H-pyran-4-yl)ureido)butyl)-1H-imidazo[4,5-c]quinolin-2-yl)methyl)(ethyl)carbamate as a brown oil.

MS (ESI+) m/z 574.4 [M+H]⁺

Step 6: A round-bottom flask, equipped with a septum inlet flushing adapter with stopcock, was charged with a magnetic stir bar, benzyl ((4-amino-1-(4-(1-(tetrahydro-2H-pyran-4-yl)ureido)butyl)-1H-imidazo[4,5-c]quinolin-2-yl)methyl)(ethyl)carbamate (245 mg, 0.427 mmol) and methanol (2 mL) to give a pale yellow solution. After addition of 10% Pd/C (45 mg, 0.470 mmol) the apparatus was connected to a balloon filled with hydrogen and alternately evacuated and filled with hydrogen three times. Hydrogen was then admitted to the system and the reaction mixture was stirred under atmospheric pressure at room temperature overnight. Additional 10% Pd/C (270 mg, 2.82 mmol, 6 eq) was added over the next 20 h to obtain a complete conversion according to HPLC/MS monitoring. The apparatus was then purged with argon and the catalyst was removed by filtration through a thin pad of CELITE®. The filter cake was washed with methanol until all the product was washed out of the filter and the filtrates were combined, concentrated under reduced pressure and dried in high vacuum. The residue was purified by preparative TLC (SiO₂ 20 cm², CHCl₃/MeOH/32% ammonia solution 100:10:1) to afford 54 mg (28%) of a white solid.

¹H NMR (300 MHz, DMSO-d₆) δ 8.03 (d, 1H), 7.61 (dd, 1H), 7.43 (ddd, 1H), 7.26 (ddd, 1H), 6.46 (br s, 2H), 5.77 (br s, 2H), 4.61 (t, 2H), 4.04 (s, 2H), 4.02-3.79 (m, 3H), 3.34 (m, 2H), 3.09 (t, 2H), 2.63 (q, 2H), 1.85 (m, 2H), 1.74-1.53 (m, 4H), 1.46 (m, 2H), 1.06 (t, 3H); MS (ESI+) m/z 440.3 [M+H]⁺

Scheme 6 synthesis of Example 3 (for illustrative purposes)
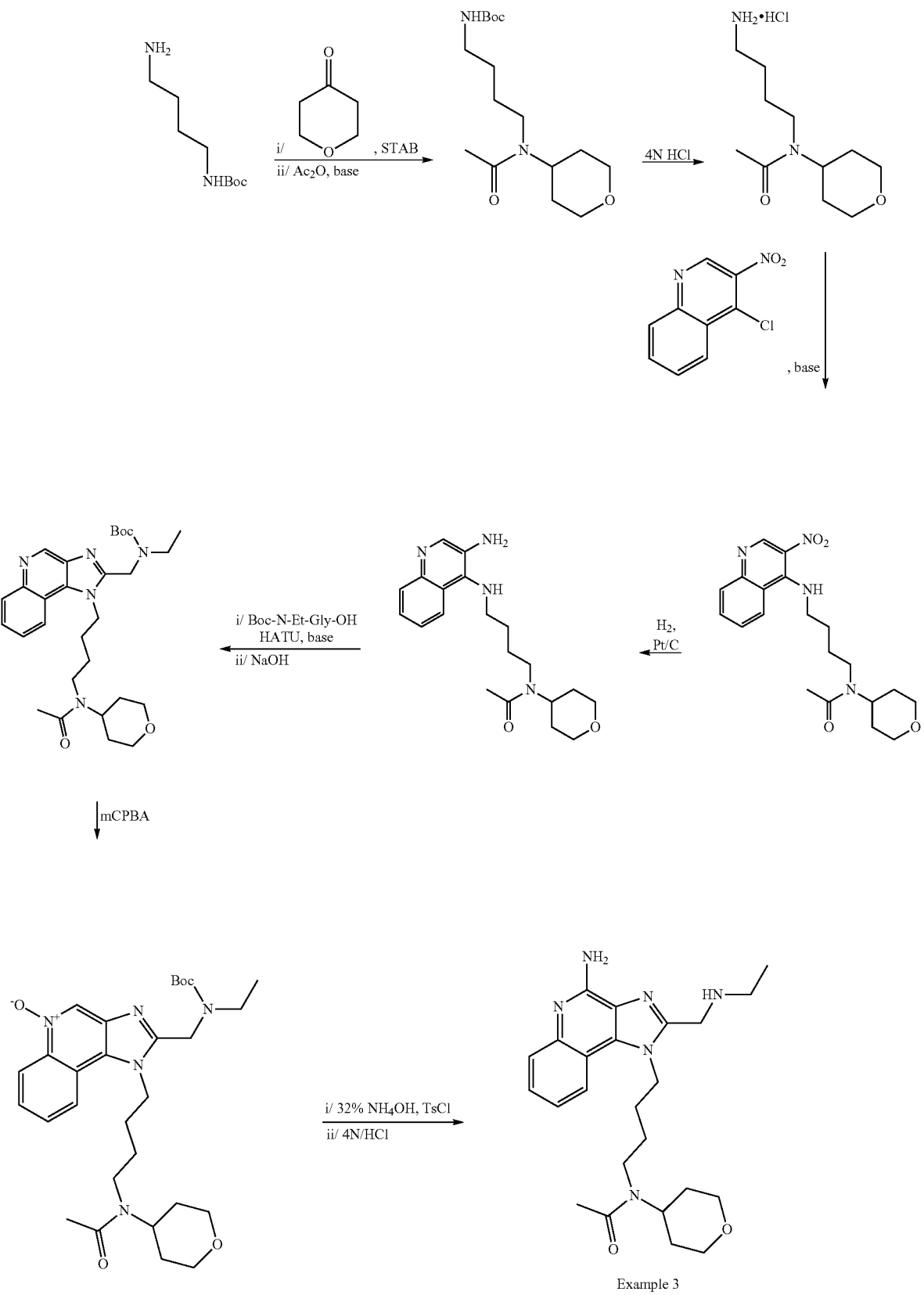
Example 3

Example 3 (For Illustrative Purposes)

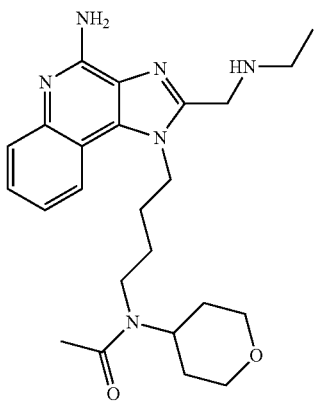 [SMILES: CCNCc1nc2c(N)nc3ccccc3c2n1CCCCN(C(C)=O)C1CCOCC1]

N-(4-(4-Amino-2-((ethylamino)methyl)-1H-imidazo[4,5-c]quinolin-1-yl)butyl)-N-(tetrahydro-2H-pyran-4-yl)acetamide Step 1: A three-necked, 2-L round-bottomed flask was equipped with a 50 mm×21 mm octagonal KOMET™ magnetic stir bar, a reflux condenser connected with a mineral oil bubbler and two glass stoppers. N-Boc-putrescine (56.41 g, 299.65 mmol, 1.5 eq), CH$_2$Cl$_2$ (500 mL) and molecular sieves 4 Å, powder <5 micron (Aldrich) (90 g) were charged and the mixture was stirred at room temperature for 5 min. Sodium triacetoxyborohydride (84.68 g, 399.53 mmol, 2 eq) was added in portions and the resulting mixture was heated at 40° C. for 5 min under stirring. A solution of oxan-4-one (20.00 g, 199.77 mmol) in CH$_2$Cl$_2$ (500 mL) was rapidly added and the resulting mixture was refluxed overnight. The progress of the reaction was monitored by TLC (CHCl$_3$/MeOH/32% ammonia solution 90:9:1) and the spots were detected by treatment with ninhydrine reagent and chlorine/o-tolidine reagent. Additional oxan-4-one (4.00 g, 39.96 mmol, 0.2 eq) was added over the two next days to obtain a complete conversion. The reaction mixture was then allowed to cool down to room temperature, triethylamine (75.80 g, 749.12 mmol, 3.75 eq) and acetic anhydride (45.89 g, 449.47 mmol, 2.25 eq) were added and the mixture was stirred at room temperature overnight. The progress of the reaction was monitored by TLC CHCl$_3$/MeOH/32% ammonia solution 90:9:1). The reaction mixture was then poured into cold water (1.4 L), the molecular sieves were removed by filtration and the dichloromethane layer was separated from the aqueous layer. The aqueous layer was extracted with dichloromethane (3×250 mL) and the combined organic layers were washed with brine (2×250 mL), dried over Na$_2$SO$_4$, filtered and concentrated under reduced pressure. The crude substance was purified by flash chromatography on silica gel CHCl$_3$/MeOH/32% ammonia solution 440:9:1) to obtain 62.8 g (quantitative) of tert-butyl (4-(N-(tetrahydro-2H-pyran-4-yl)acetamido)butyl)carbamate as an orange oil.

$^1$H NMR (300 MHz, CDCl$_3$) (mixture of rotamers) δ 4.81-4.43 (m, 1.6H), 4.01 (m, 2H), 3.71 (m, 0.4H), 3.56-3.30 (m, 2H), 3.29-3.02 (m, 4H), 2.20-2.00 (m, 3H), 1.93-1.35 (m, 17H). No LC-MS was made, since the compound is not detectable in UV.

Step 2: A round-bottom flask was charged with a magnetic stir bar, a solution of tert-butyl (4-(N-(tetrahydro-2H-pyran-4-yl)acetamido)butyl)carbamate (62.81 g, 199.76 mmol) in dichloromethane (1.3 L). A solution of 4N HCl/1,4-dioxane (1.3 L) was carefully added and the resulting mixture was stirred at room temperature overnight. The progress of the reaction was monitored by TLC (CHCl$_3$/MeOH/32% ammonia solution 240:9:1) and the spots were visualized by treatment with ninhydrine reagent. The reaction mixture was concentrated in vacuo, and the resulting solid was triturated with diethyl ether, filtered off, washed with diethyl ether and dried in vacuo to afford 51.46 g of N-(4-aminobutyl)-N-(tetrahydro-2H-pyran-4-yl)acetamide hydrochloride as a beige solid. The substance was used for the next step without any further purification.

$^1$H NMR (300 MHz, DMSO-d$_6$) (mixture of rotamers) δ 7.93 (m, 3H, NH$_3^+$), 4.25 (m, 0.45H), 3.99-3.71 (m, 2.55H), 3.45-3.24 (m, 2H), 3.23-3.03 (m, 2H), 2.88-2.65 (m, 2H), 2.06 (s, 1.6H), 2.01 (s, 1.4H), 1.89-1.63 (m, 2H), 1.63-1.33 (m, 6H). No LC-MS was made, since the compound is not detectable in UV.

Step 3: A round-bottom flask was charged with a magnetic stir bar, N-(4-aminobutyl)-N-(tetrahydro-2H-pyran-4-yl)acetamide hydrochloride (crude, 51.46 g, 199.91 mmol), triethylamine (121.37 g, 1199.43 mmol, 6 eq) and dichloromethane (2.1 L) and the resulting pale yellow solution was cooled to 0-4° C. in an ice bath. A solution of 4-chloro-3-nitroquinoline (see preparation A) (45.87 g, 219.90 mmol) in CH$_2$Cl$_2$ (1.05 L) prepared in the previous step was carefully added, the resulting mixture was stirred at 0-4° C. for 10 min and then at room temperature overnight. The progress of the reaction was monitored by TLC CHCl$_3$/MeOH/32% ammonia solution 80:18:2 and 240:9:1) and by HPLC/MS and the spots were visualized by treatment with ninhydrine reagent. The reaction mixture was then partitioned between water (6 L) and a mixture of dichloromethane and methanol (9:1, 1 L). The aqueous layer was separated from the organic layer and extracted with a mixture of dichloromethane and methanol (9:1, 3×1 L). The combined organic layers were dried over Na$_2$SO$_4$, filtered and concentrated in vacuo. The crude substance was purified by flash chromatography on silica gel (CHCl$_3$/MeOH/32% ammonia solution 540:9:1) to afford 72.89 g (94%) of N-(4-((3-nitroquinolin-4-yl)amino)butyl)-N-(tetrahydro-2H-pyran-4-yl)acetamide as a red-yellow oil.

MS (ESI+) m/z 387.0 [M+H]$^+$

Step 4: A 250 mL PARR vessel (pressure vessel, Parr Instrument GmbH, Germany) was charged with N-(4-((3-nitroquinolin-4-yl)amino)butyl)-N-(tetrahydro-2H-pyran-4-yl)acetamide (16.89 g, 43.71 mmol), 5% platinum on carbon (8.60 g, 2.19 mmol, 5 mol %) and toluene (90 mL). The vessel was placed on a PARR shaker and pressurized to 50 psi (3.5 kg/cm$^2$). The reaction was monitored by TLC (CHCl$_3$/MeOH/32% ammonia solution 240:9:1) and was complete after one hour. The catalyst was removed by filtration through a small pad of CELITE® Hyflo Supercel, the filter cake was washed several times with ethanol and the filtrates were combined. The volatiles were removed under reduced pressure and the crude substance was purified by flash chromatography on silica gel (CHCl$_3$/MeOH/32% ammonia solution 240:9:1 to 140:9:1) to afford 14.28 g (92%) of N-(4-((3-aminoquinolin-4-yl)amino)butyl)-N-(tetrahydro-2H-pyran-4-yl)acetamide as a red-orange oil.

$^1$H NMR (300 MHz, CDCl$_3$) (mixture of rotamers) δ 8.49 (s, 0.4H), 8.45 (s, 0.6H), 8.02-7.92 (m, 1H), 7.91-7.73 (m, 1H), 7.53-7.38 (in, 1H), 4.55 (m, 0.6H), 4.16-3.05 (m, 11.4H), 2.14 (s, 1.8H), 2.04 (s, 1.2H), 1-90-1.44 (m, 8H); MS (ESI+) m/z 357.0 [M+H]$^+$ Step 5: A round-bottom flask was charged with a magnetic stir bar, N-(4-((3-aminoquinolin-4-yl)amino)butyl)-N-(tetrahydro-2H-pyran-4-yl)acetamide (1.00 g, 2.81 mmol), N-Boc-N-ethylglycine (0.68 g, 3.37 mmol, 1.2 eq), 2-(3H-[1,2,3]triazolo[4,5-b]pyridin-3-yl)-1,1,3,3-tetramethylisouronium hexafluorophosphate(V) (HATU, 1.28 g, 3.37 mmol, 1.2 eq), triethylamine (0.85 g, 8.42 mmol, 3 eq), 4-dimethylaminopyridine (0.03 g, 0.28 mmol, 0.1 eq) and anhydrous DMF (20 mL) to give a red-yellow solution. The reaction mixture was stirred at room temperature until TLC monitoring (CHCl$_3$/MeOH/32% ammonia solution 140:9:1) and HPLC/MS indicated complete conversion after about 10-12 hours. The solvent was then removed under reduced pressure and the residue, dissolved in ethyl acetate, was washed with water. The organic layer was dried over Na$_2$SO$_4$, filtered and concentrated under reduced pressure. The residue was dissolved in ethanol (20 mL), 2M NaOH (4.91 mL, 9.82 mmol, 3.5 eq) was added and the resulting mixture was refluxed until TLC monitoring (CHCl$_3$/MeOH/32% ammonia solution 140:9:1) and HPLC/MS indicated complete conversion after 18 h. The reaction was concentrated in vacuo and the residue was partitioned between dichloromethane (100 mL) and 1M HCl (50 mL). The organic layer was dried over Na$_2$SO$_4$, filtered and concentrated in vacuo. The crude substance was purified by flash chromatography on silica gel (CHCl$_3$/MeOH/32% ammonia solution 240:9:1) to give 1.24 g (84%) of tert-butyl ethyl ((1-(4-(N-(tetrahydro-2H-pyran-4-yl)acetamido)butyl)-1H-imidazo[4,5-c]quinolin-2-yl)methyl)carbamate as a yellow-orange oil.

MS (ESI+) m/z 524.8 [M+H]$^+$

Step 6: A round bottom flask was charged with a magnetic stir bar, tert-butyl ethyl((1-(4-(N-(tetrahydro-2H-pyran-4-yl)acetamido)butyl)-1H-imidazo[4,5-c]quinolin-2-yl)methyl)carbamate (1.24 g, 2.37 mmol) and chloroform (100 mL). Solid 3-chlorobenzoperoxoic acid (1.02 g, 5.92 mmol, 2.5 eq) was added in portions to the solution over the course of 15 minutes and the reaction was stirred at room temperature overnight until TLC monitoring CHCl$_3$/MeOH/32% ammonia solution 140:9:1) and HPLC/MS indicated complete conversion. The solution was then partitioned between chloroform (100 mL) and aqueous saturated sodium bicarbonate solution (100 mL) and the layers were separated. The organic layer was washed successively with aqueous saturated sodium bicarbonate solution (100 mL) and brine (100 mL), dried over Na$_2$SO$_4$, filtered and then concentrated under reduced pressure to afford 1.33 g (quantitative) of 2-(((tert-butoxycarbonyl)(ethyl)amino)methyl)-1-(4-(N-(tetrahydro-2H-pyran-4-yl)acetamido)butyl)-1H-imidazo[4,5-c]quinolin 5-oxide as a red-brown oil. The substance was used for the next step without any further purification.

MS (ESI+) m/z 540.0 [M+H]$^+$

Step 7: A round-bottom flask was charged with a magnetic stir bar, 2-(((tert-butoxycarbonyl)(ethyl)amino)methyl)-1-(4-(N-(tetrahydro-2H-pyran-4-yl)acetamido)butyl)-1H-imidazo[4,5-c]quinolin 5-oxide (1.33 g, 2.46 mmol), chloroform (30 mL) and ammonia solution (32%, 30 mL). p-Toluenesulfonyl chloride (0.47 g, 2.46 mmol, 1 eq) was added to the biphasic mixture in one portion and the reaction mixture was vigorously stirred at room temperature overnight until TLC monitoring CHCl$_3$/MeOH/32% ammonia solution 140:9:1) and HPLC/MS indicated complete conversion. The reaction mixture was then diluted with chloroform (70 mL) and the phases were separated. The aqueous layer was adjusted to pH 7 with 2M HCl and extracted with chloroform (2×100 mL). The combined organic layers were washed with brine (150 mL), dried over Na$_2$SO$_4$, filtered and concentrated under reduced pressure. The residue was purified by flash chromatography on silica gel (CHCl$_3$/MeOH/32% ammonia solution 240:9:1) to afford 430 mg of a yellow-beige solid. The latter was triturated with hot solvents (successively ethyl acetate, acetone and methanol), cooled down and filtered off to remove side products. A portion of the solid was dissolved in chloroform (25 mL) and treated with a solution of 4N HCl/1,4-dioxane (25 mL) at room temperature overnight to remove the Boc-protecting group. After evaporation of the volatiles in vacuo, the residue was purified by flash chromatography on silica gel CHCl$_3$/MeOH/32% ammonia solution 90:9:1) to give 202 mg of an off-white solid.

$^1$H NMR (300 MHz, CDCl$_3$) (mixture of rotamers) δ 7.91 (t, 1H), 7.83 (m, 1H), 7.52 (m, 1H), 7.33 (t, 1H), 5.42 (br s, 2H), 4.59 (m, 2.4H), 4.10 (s, 2H), 4.01 (m, 2H), 3.71 (m, 0.6H), 3.42 (m, 2H), 3.25 (dt, 2H), 2.79 (q, 2H), 2.13 (s, 1.8H), 2.09 (s, 1.2H), 1.98 (m, 2H), 1.86-1.53 (m, 6H), 1.18 (t, 3H); MS (ESI+) m/z 439.3 [M+H]$^+$ Scheme 7 synthesis of Example 5 and 6 (for illustration purposes)

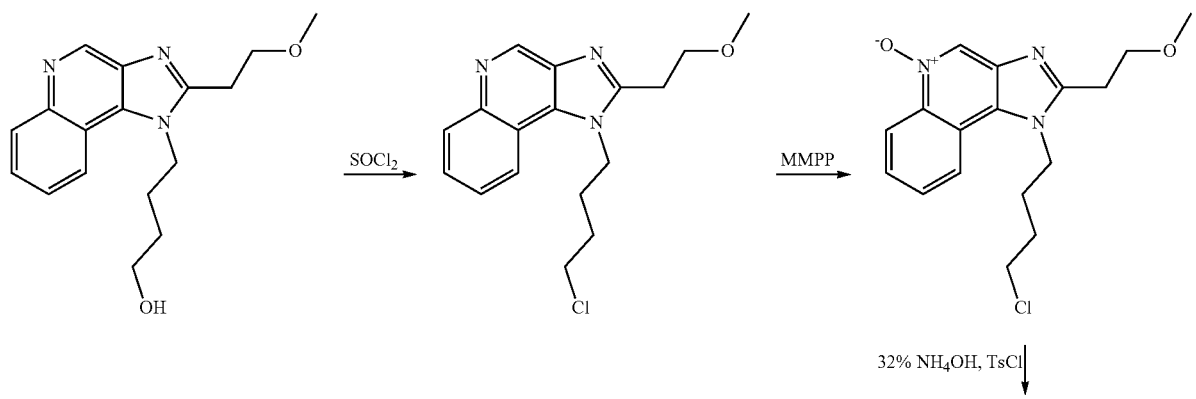

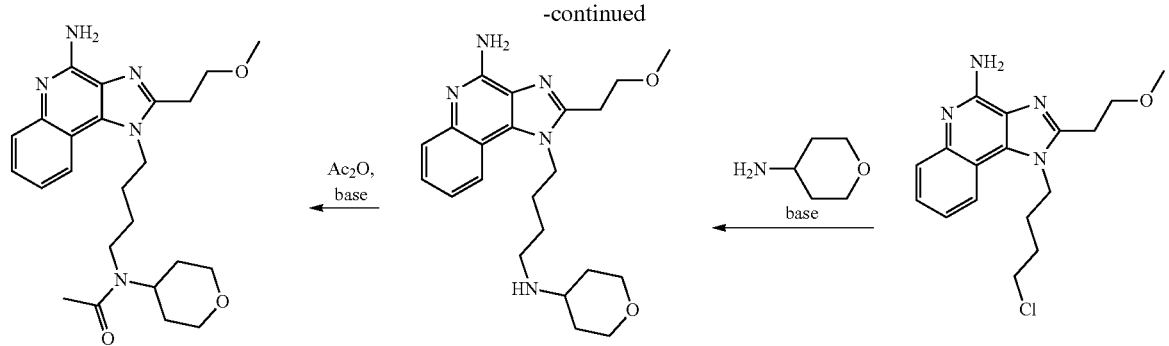

Example 5

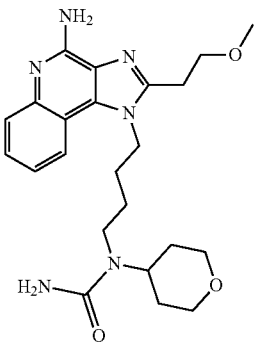

Example 6

Example 5 (For Illustrative Purposes)

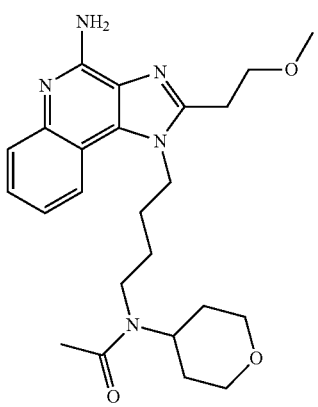 [SMILES: COCCc1nc2c(N)nc3ccccc3c2n1CCCCN(C(C)=O)C1CCOCC1]

N-(4-(4-Amino-2-(2-methoxyethyl)-1H-imidazo[4,5-c]quinolin-1-yl)butyl)-N-(tetrahydro-2H-pyran-4-yl)acetamide Step 1: A round-bottom flask was charged with a magnetic stir bar, 4-(2-(2-methoxyethyl)-1H-imidazo[4,5-c]quinolin-1-yl)butan-1-ol (see preparation C) (9.48 g crude material, corresponding to ~14.47 mmol starting material) and dichloroethane (400 mL) to give a yellow-brown solution. After addition of thionyl chloride (6.89 mL, 95.00 mmol, 6.5 eq), the mixture was stirred at room temperature for 12 h until TLC monitoring (CH$_2$Cl$_2$/MeOH 9:1) and HPLC/MS indicated complete reaction. The volatiles were removed under reduced pressure, the residue was dissolved in dichloromethane, basified with triethylamine (7.45 g, 73.67 mmol, 5 eq) and purified by flash chromatography on silica gel (CH$_2$Cl$_2$/MeOH 95:5) to get 3.35 g (72%, based on 14.47 mmol of starting material) of 1-(4-chlorobutyl)-2-(2-methoxyethyl)-1H-imidazo[4,5-c]quinoline as a reddish-brown oil.

MS (ESI+) m/z 317.9 319.8 [M+H]$^+$

Step 2: A reaction flask was charged with a magnetic stir bar, 1-(4-chlorobutyl)-2-(2-methoxyethyl)-1H-imidazo[4,5-c]quinoline hydrochloride (3.35 g, 9.46 mmol) and water (300 mL) to give a reddish-brown suspension. After addition of magnesium monoperoxyphthalate hexahydrate (MMPP) (4.68 g, 9.46 mmol, 1 eq) the mixture was stirred at 60° C. After a reaction time of 2 h, magnesium monoperoxyphthalate hexahydrate (4.68 g, 9.46 mmol, 1 eq) was added and the mixture was further stirred at 60° C. for 90 min until TLC monitoring ($CH_2Cl_2$/MeOH 9:1) and HPLC/MS indicated complete reaction. The reaction mixture was extracted with chloroform (3×100 mL) and the combined organic layers were washed with saturated sodium bicarbonate solution (1×50 mL). The bicarbonate layer was extracted with chloroform (3×50 mL), the combined organic layers were washed with brine (100 mL), dried over $Na_2SO_4$, filtered and concentrated in vacuo to give 1.75 g (55%) of 1-(4-chlorobutyl)-2-(2-methoxyethyl)-1H-imidazo[4,5-c]quinoline 5-oxide as a dark yellow oil. The material was used without further purification for the next step.

MS (ESI+) m/z 333.9 335.8 [M+H]$^+$

Step 3: A round-bottom flask was charged with a magnetic stir bar, 1-(4-chlorobutyl)-2-(2-methoxyethyl)-1H-imidazo[4,5-c]quinoline 5-oxide (1.75 g, 5.24 mmol), chloroform (50 mL) and ammonia solution (32%, 50 mL). 4-Methylbenzene-1-sulfonyl chloride (1.20 g, 6.29 mmol, 1.2 eq) was added to the biphasic mixture in one portion and the reaction was vigorously stirred at room temperature overnight. TLC monitoring ($CH_2Cl_2$/MeOH 9:1) and HPLC/MS indicated complete reaction and formation of the desired product. The mixture was diluted with chloroform (100 mL) and brine (150 mL). The organic layer was separated from the aqueous layer and washed with brine (2×100 mL), dried over $Na_2SO_4$, filtered and evaporated under reduced pressure. The residual brownish-yellow oil was purified by preparative HPLC to afford 586 mg (34%) of 1-(4-chlorobutyl)-2-(2-methoxyethyl)-1H-imidazo[4,5-c]quinolin-4-amine as a yellow solid.

MS (ESI+) m/z 332.9 334.8 [M+H]$^+$

Step 4: In a sealed vial, a mixture of 1-(4-chlorobutyl)-2-(2-methoxyethyl)-1H-imidazo[4,5-c]quinolin-4-amine (150 mg, 0.451 mmol), sodium iodide (68 mg, 0.451 mmol, 1 eq), N-ethyl-N-isopropylpropan-2-amine (116 mg, 0.901 mmol, 2 eq), 4-aminotetrahydropyran (137 mg, 1.352 mmol, 3 eq) and molecular sieve 4 Å, powder <5 micron (Aldrich) (750 mg) in anhydrous DMA (4.5 mL) was stirred at 100° C. for 4 days until HPLC/MS monitoring indicated complete reaction and formation of the desired substance. The reaction mixture was filtered and concentrated under reduced pressure to afford 302 mg of 2-(2-methoxyethyl)-1-(4-((tetrahydro-2H-pyran-4-yl)amino)butyl)-1H-imidazo[4,5-c]quinolin-4-amine as a brown residue. The material was used without further purification for the next step.

MS (ESI+) m/z 398.0 [M+H]$^+$

Step 5: A pear-shaped flask was charged with a magnetic stir bar, 2-(2-methoxyethyl)-1-(4-((tetrahydro-2H-pyran-4-yl)amino)butyl)-1H-imidazo[4,5-c]quinolin-4-amine (302 mg, 0.760 mmol), 2N NaOH solution (3.799 mL, 7.597 mmol, 10 eq) and water (5 mL) to give a yellow solution. After addition of acetic anhydride (0.776 g, 7.597 mmol, 10 eq), the reaction mixture was stirred at room temperature for 24 h and the progress of the reaction was monitored by HPLC/MS. 2N NaOH solution (15.194 mL, 30.388 mmol, 40 eq) and acetic anhydride (3.102 g, 30.388 mmol, 40 eq) were then added and the mixture was further stirred at room temperature for another 24 h. The reaction mixture was filtered and the product was isolated via preparative HPLC to afford 89 mg (27%) of a brownish-yellow solid.

$^1$H NMR (300 MHz, DMSO-d$_6$) δ 8.02 (dd, 1H), 7.61 (d, 1H), 7.42 (t, 1H), 7.24 (t, 1H), 6.42 (s, 2H), 4.54 (m, 2H), 4.24-3.68 (m, 5H), 3.45-3.09 (m, 9H), 2.01 (d, 3H), 1.89-1.34 (m, 8H); MS (ESI+) m/z 439.9 [M+H]$^+$

Example 6 (For Illustrative Purposes)

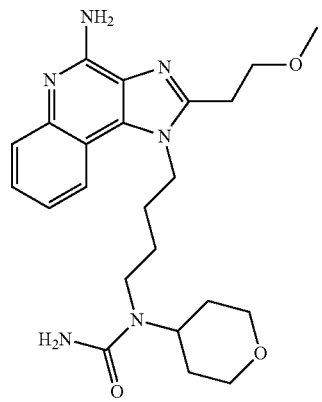 [SMILES: COCCc1nc2c(N)nc3ccccc3c2n1CCCCN(C(N)=O)C1CCOCC1]

1-(4-(4-Amino-2-(2-methoxyethyl)-1H-imidazo[4,5-c]quinolin-1-yl)butyl)-1-(tetrahydro-2H-pyran-4-yl)urea A round-bottom flask was charged with a magnetic stir bar, 2-(2-methoxyethyl)-1-(4-((tetrahydro-2H-pyran-4-yl)amino)butyl)-1H-imidazo[4,5-c]quinolin-4-amine (obtained in Example 5, Steps 1-4) (281 mg, 0.706 mmol), triethylamine (71 mg, 0.706 mmol, 1 eq) and anhydrous chloroform (5 mL) to give a yellow solution. The solution was cooled to 0-4° C. in an ice bath and after addition of trimethylsilyl isocyanate (89 mg, 0.776 mmol, 1.1 eq) the reaction was stirred at room temperature. Reaction monitoring by HPLC/MS and TLC (CHCl$_3$/MeOH/32% ammonia solution 90:9:1) showed an incomplete consumption of the starting material after 1 h. Additional trimethylsilyl isocyanate (81 mg, 0.706 mmol, 1 eq) was added every 30 min over the next 3.5 h to obtain a complete conversion. The reaction was then quenched by addition of water (5 mL) and subsequently stirred at room temperature for 30 min. The mixture was diluted with 100 mL of absolute ethanol and then concentrated under reduced pressure to approximately half of the volume. Another 100 mL of absolute ethanol were added and the solution was evaporated in vacuo. The crude material was purified by TLC (SiO$_2$ 20 cm$^2$, CHCl$_3$/MeOH/32% ammonia solution 90:9:1) to afford 91 mg (29%) of an off-white solid.

$^1$H NMR (300 MHz, DMSO-d$_6$) δ 8.02 (dd, 1H), 7.61 (dd, 1H), 7.42 (ddd, 1H), 7.25 (ddd, 1H), 6.42 (s, 2H), 5.77 (br s, 2H), 4.52 (t, 2H), 4.04-3.76 (m, 5H), 3.38-3.24 (m, 5H), 3.19 (t, 2H), 3.08 (t, 2H), 1.88-1.53 (m, 6H), 1.45 (m, 2H); MS (ESI+) m/z 441.5 [M+H]$^+$ Scheme 8 synthesis of Example 7-11

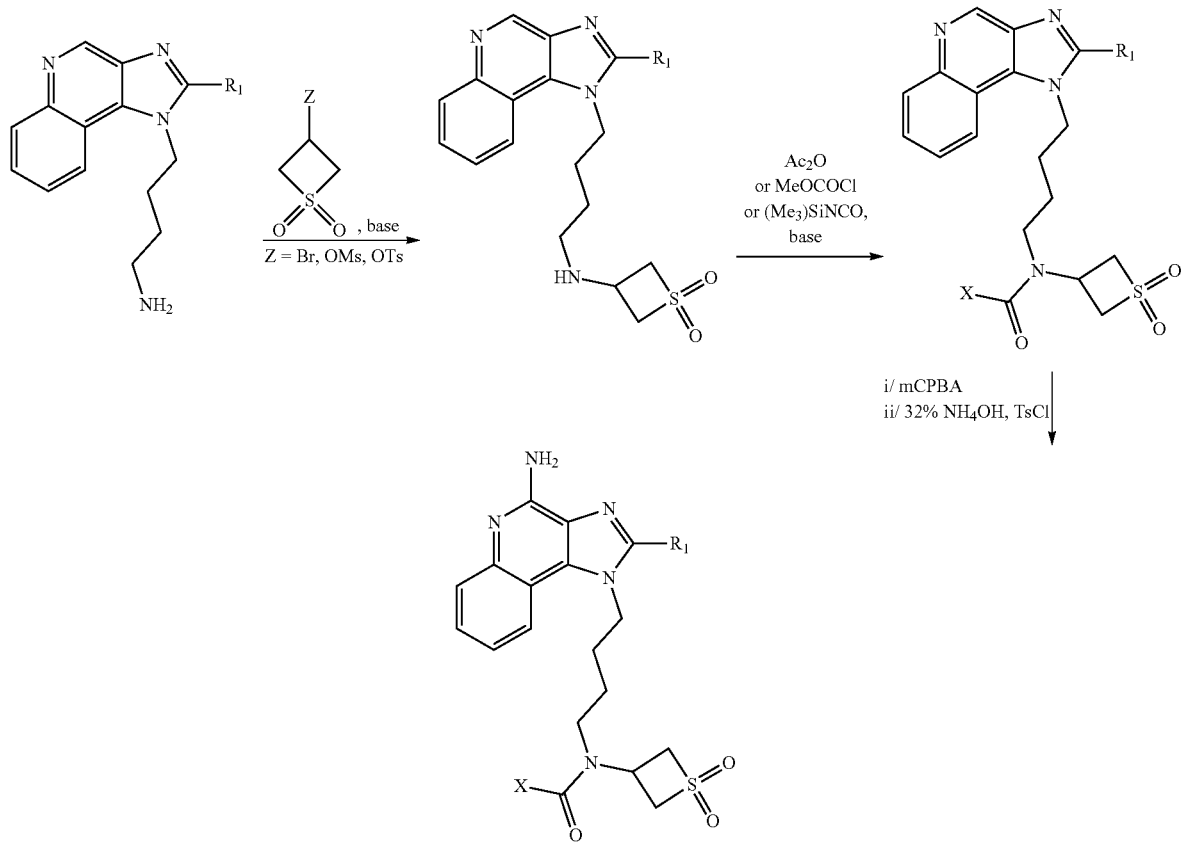

Example 7   R1 = CH₂CH₃; X = CH₃
Example 8   R1 = CH₂CH₃; X = OCH₃
Example 9   R1 = CH₂CH₃; X = NH₂
            R1 = CH₂N(Cbz)CH₂CH₃; X = CH₃      ⎤ H₂, Pd/C
Example 10  R1 = CH₂NHCH₂CH₃; X = CH₃          ⎦
            R1 = CH₂N(Cbz)CH₂CH₃; X = OCH₃    ⎤ H₂, Pd/C
Example 11  R1 = CH₂NHCH₂CH₃; X = OCH₃         ⎦

Example 7

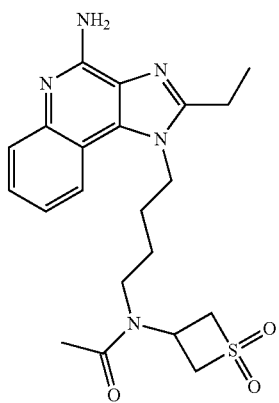 [SMILES: CCc1nc2c(N)nc3ccccc3c2n1CCCCN(C(C)=O)C1CS(=O)(=O)C1]

N-(4-(4-Amino-2-ethyl-1H-imidazo[4,5-c]quinolin-1-yl)butyl)-N-(1,1-dioxidothietan-3-yl)acetamide Step 1: 4-(2-Ethyl-1H-imidazo[4,5-c]quinolin-1-yl)butan-1-amine (see preparation D) (10.4 g, 38.7 mmol) was suspended in MeOH/THF (1:1.5 v/v, 150 mL) and a solution of triethylamine (51.9 mL, 373.5 mmol, 9.65 eq) in MeOH/THF (1:1 v/v, 20 mL) was added dropwise. 3-Bromothietane 1,1-dioxide (9.3 g, 50.3 mmol, 1.3 eq) was then added in portions and the resulting solution was stirred at 70° C. until TLC monitoring (CH₂Cl₂/MeOH 9:1) and HPLC/MS indicated an almost complete conversion after 18 h. The reaction mixture was then allowed to cool down to room temperature and concentrated under reduced pressure. The brown residue was partitioned between CH₂Cl₂ and water, the organic phase was washed several times with water and the combined aqueous phases were extracted several times with CH₂Cl₂. The combined organic phases were dried over MgSO₄, filtered off and evaporated. The resulting solid was then washed successively with EtOAc and petroleum ether and dried under vacuum to yield 3-((4-(2-ethyl-1H-imidazo[4,5-c]quinolin-1-yl)butyl)amino)thietane 1,1-dioxide (5.68 g, 39%) as a beige solid.

¹H NMR (300 MHz, DMSO-d₆) δ 9.14 (s, 1H), 8.36 (m, 1H), 8.14 (m, 1H), 7.69 (m, 2H), 4.60 (t, 2H), 4.25 (m, 2H), 3.85 (m, 2H), 3.58 (m, 1H), 3.01 (q, 2H), 2.50 (m, 2H), 1.87 (m, 2H), 1.57 (m, 2H), 1.42 (t, 3H); MS (ESI+) m/z 373.1 [M+H]⁺

Step 2: To a solution of 3-((4(2-ethyl-1H-imidazo[4,5-c]quinolin-1-yl)butyl)amino)thietane 1,1-dioxide (3.14 g, 8.42 mmol) in CH₂Cl₂ (30 mL) at 0° C. were added triethylamine (3.5 mL, 25.3 mmol, 3 eq) dissolved in CH₂Cl₂ (5 mL) and acetic acid anhydride (3.1 mL, 33.7 mmol, 4 eq) dissolved in CH₂Cl₂ (5 mL). The mixture was stirred for 1 h at 0° C. and then at room temperature for 18 h until HPLC/MS monitoring indicated complete conversion. The reaction was filtered off and the filtrate was partitioned between CH₂Cl₂ and water. The organic phase was washed three times with water and the combined aqueous phases were washed twice with CH₂Cl₂. The combined organic layers were dried over MgSO₄, filtered off and concentrated. The resulting solid was then washed successively with EtOAc and petroleum ether and dried under vacuum to give N-(1,1-dioxidothietan-3-yl)-N-(4-(2-ethyl-1H-imidazo[4,5-c]quinolin-1-yl)butyl)acetamide (2.16 g, 62%) as an off-white solid.

¹H NMR (300 MHz, DMSO-d₆) δ 9.14 (s, 1H), 8.35 (m, 1H), 8.15 (m, 1H), 7.69 (m, 2H), 4.72-4.12 (m, 7H), 3.39 (t, 2H), 3.02 (q, 2H), 2.03 (s, 3H), 1.76 (m, 4H), 1.42 (t, 3H); MS (ESI+) m/z 415.0 [M+H]⁺

Step 3: To a magnetically stirred solution of N-(1,1-dioxidothietan-3-yl)-N-(4-(2-ethyl-1H-imidazo[4,5-c]quinolin-1-yl)butyl)acetamide (330 mg, 0.796 mmol) in CH₂Cl₂ (20 mL) was added peroxyacetic acid (38-40% in acetic acid, 398 µL, 2.388 mmol, 3 eq) at room temperature and the resulting mixture was then stirred at reflux for 3 h. The completion of the conversion was monitored by HPLC/MS analysis. The mixture was then cooled down to room temperature, diluted with water (40 mL) and stirred for 5 min. The organic solvent was then evaporated and the resulting aqueous phase was lyophilized to afford the crude 1-(4-(N-(1,1-dioxidothietan-3-yl)acetamido)butyl)-2-ethyl-1H-imidazo[4,5-c]quinoline 5-oxide (340 mg) as a white powder (MS (ESI+) m/z 430.8 [M+H]⁺). The solid was dissolved in CH₂Cl₂ (15 mL) and an excess of ammonium hydroxide solution 32% (1 mL) was added. Tosyl chloride (151 mg, 0.790 mol, 1 eq) in CH₂Cl₂ (3 mL) was then added dropwise to the vigorously stirred mixture at room temperature and stirring was continued until TLC (CH₂Cl₂/MeOH 9:1) and HPLC/MS monitoring indicated a complete conversion after 1.5 h. The mixture was then concentrated under reduced pressure and the residue was sonicated in MeOH (5 mL). The resulting solid was filtered off and washed with MeOH to afford 160 mg (47%) of a white powder. Alternatively, the two successive chemical reactions can be performed one-pot without isolation of the N-oxide intermediate.

¹H NMR (300 MHz, DMSO-d₆) δ 8.02 (d, 1H), 7.62 (dd, 1H), 7.42 (ddd, 1H), 7.25 (ddd, 1H), 6.43 (br s, 2H), 4.93-4.13 (m, 7H), 3.39 (m, 2H), 2.95 (q, 2H), 2.03 (s, 3H), 1.74 (m, 4H), 1.38 (t, 3H); MS (ESI+) m/z 430.2 [M+H]⁺

Example 8

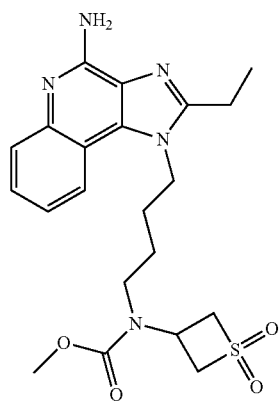 [SMILES: CCc1nc2c(N)nc3ccccc3c2n1CCCCN(C(=O)OC)C1CS(=O)(=O)C1]

Methyl (4-(4-amino-2-ethyl-1H-imidazo[4,5-c]quinolin-1-yl)butyl)(1,1-dioxidothietan-3-yl)carbamate Prepared as described in Example 7, starting with 600 mg (1.61 mmol) of 3-((4-(2-ethyl-1H-imidazo[4,5-c]quinolin-1-yl)butyl)amino)thietane 1,1-dioxide (from step 1) and using methyl chloroformate (2 eq) for the formation of the carbamate to yield 190 mg (23% overall yield for 3 steps) of the tosylate salt as an off-white solid.

¹H NMR (300 MHz, DMSO-d₆) δ 8.08 (d, 1H), 7.72 (d, 1H), 7.55 (t, 1H), 7.47 (d, 0.8H, 2×CH of tosylate), 7.40 (t, 1H), 7.10 (d, 0.8H, 2×CH of tosylate), 4.62-4.24 (m, 7H), 3.60 (s, 3H), 3.33 (m, 2H), 2.98 (q, 2H), 2.28 (s, 1.2H, CH₃ of tosylate), 1.84-1.57 (m, 4H), 1.39 (t, 3H); MS (ESI+) m/z 446.0 [M+H]⁺

Example 9

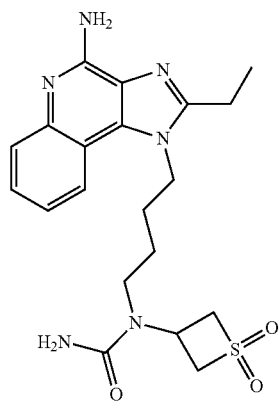

1-(4-(4-Amino-2-ethyl-1H-imidazo[4,5-c]quinolin-1-yl)butyl)-1-(1,1-dioxidothietan-3-yl)urea Prepared as described in Example 7, starting with 80 mg (0.215 mmol) of 3-((4-(2-ethyl-1H-imidazo[4,5-c]quinolin-1-yl)butyl)amino)thietane 1,1-dioxide (from step 1) and using trimethylsilyl isocyanate (4 eq) for the formation of the urea to yield 8.5 mg (9% overall yield for 3 steps) of a beige solid.

¹H NMR (300 MHz, DMSO-d₆) (mixture of rotamers) δ 8.17 (d, 1H), 8.08 (br s, 0.5H), 7.77 (d, 1H), 7.64 (t, 1H), 7.50 (t, 1H), 6.14 (br s, 2H), 5.39 (br s, 1.5H), 4.67-4.14 (m, 7H), 3.50 (m, 2H), 2.99 (m, 2H), 1.78 (m, 2H), 1.66 (m, 2H), 1.40 (m, 3H); MS (ESI+) m/z 431.2 [M+H]⁺

Example 10

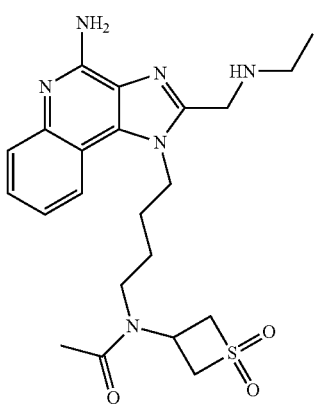 [SMILES: CCNCc1nc2c(N)nc3ccccc3c2n1CCCCN(C(C)=O)C1CS(=O)(=O)C1]

N-(4-(4-Amino-2-((ethylamino)methyl)-1H-imidazo[4,5-c]quinolin-1-yl)butyl)-N-(1,1-dioxidothietan-3-yl)acetamide Steps 1-3: Prepared as described in Example 7, using benzyl ((1-(4-aminobutyl)-1H-imidazo[4,5-c]quinolin-2-yl)methyl)(ethyl)carbamate (see preparation E) (1 g, 2.317 mmol) as starting material to yield 261 mg (19% over 3 steps) of benzyl ((4-amino-1-(4-(N-(1,1-dioxidothietan-3-yl)acetamido)butyl)-1H-imidazo[4,5-c]quinolin-2-yl)methyl)(ethyl)carbamate as an off-white foam.

¹H NMR (300 MHz, CDCl₃) δ 7.85 (m, 2H), 7.53 (ddd, 1H), 7.43-7.28 (m, 6H), 5.46 (br s, 2H), 5.23 (s, 2H), 4.84 (s, 2H), 4.66-4.19 (m, 7H), 3.55-3.22 (m, 4H), 2.07 (s, 3H), 1.97-1.56 (m, 4H), 1.10 (t, 3H); MS (ESI+) m/z 573.3 [M+H]⁺

Step 4: A round-bottom flask, equipped with a septum inlet flushing adapter with stopcock, was charged with a magnetic stir bar, benzyl ((4-amino-1-(4-(N-(1,1-dioxidothietan-3-yl)acetamido)butyl)-1H-imidazo[4,5-c]quinolin-2-yl)methyl)(ethyl)carbamate (261 mg, 0.440 mmol) and methanol (20 mL) to give a colorless solution. After addition of 10% palladium on activated carbon (469 mg, 0.440 mmol, 1 eq) the apparatus was connected to a balloon filled with hydrogen and alternately evacuated and filled with hydrogen three times. Hydrogen was then admitted to the system and the reaction mixture was stirred under atmospheric pressure at room temperature overnight. TLC monitoring (CHCl₃/MeOH/32% ammonia solution 90:9:1) and HPLC/MS indicated an incomplete conversion. Additional 10% palladium on activated carbon (0.469 g, 0.440 mmol) and a further stirring overnight were necessary to obtain a complete conversion. The apparatus was then purged with argon and the catalyst was removed by filtration through a thin pad of CELITE® Hyflo Supercel on a partly coarse porosity (porosity=16-40 μm) glass filtration funnel. The filter cake was washed with methanol (3×50 mL), the combined filtrates were filtered through a 0.45 μm PTFE membrane to remove catalyst residues and concentrated under reduced pressure. The residue was purified by preparative TLC (SiO₂ 20 cm², CHCl₃/MeOH/32% ammonia solution 90:9:1) to give 108 mg (53%) of an off-white solid.

¹H NMR (300 MHz, CDCl₃) δ 7.86 (m, 2H), 7.53 (ddd, 1H), 7.34 (ddd, 1H), 5.70 (br s, 2H), 4.64 (t, 2H), 4.61-4.21 (m 5H), 4.10 (s, 2H), 3.42 (t, 2H), 2.79 (q, 2H), 2.10 (s, 3H), 2.03 (m, 2H), 1.78 (m, 2H), 1.17 (t, 3H); MS (ESI+) m/z 459.2 [M+H]⁺

Example 11

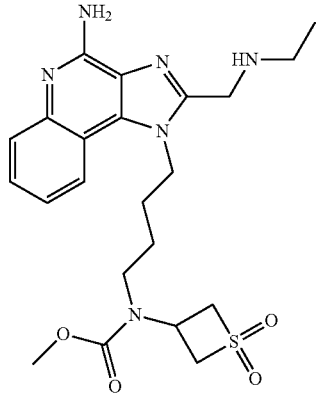 [SMILES: CCNCc1nc2c(N)nc3ccccc3c2n1CCCCN(C(=O)OC)C1CS(=O)(=O)C1]

Methyl (4-(4-amino-2-((ethylamino)methyl)-1H-imidazo[4,5-c]quinolin-1-yl)butyl)(1,1-dioxidothietan-3-yl)carbamate Prepared as described in Example 10, starting with 1 g (0.317 mmol) of benzyl ((1-(4-aminobutyl)-1H-imidazo[4,5-c]quinolin-2-yl)methyl)(ethyl)carbamate (see preparation E) and using methyl chloroformate (1 eq) for the formation of the carbamate to yield 131 mg (12% overall yield for 4 steps) of an off-white solid.

¹H NMR (300 MHz, CDCl₃) δ 7.86 (m, 2H), 7.52 (ddd, 1H), 7.33 (ddd, 1H), 5.62 (br s, 2H), 4.60 (t, 2H), 4.54-4.35 (m, 3H), 4.33-4.18 (m, 2H), 4.09 (s, 2H), 3.73 (s, 3H), 3.39 (t, 2H), 2.78 (q, 2H), 1.99 (m, 2H), 1.73 (m, 2H), 1.17 (t, 3H); MS (ESI+) m/z 475.2 [M+H]⁺

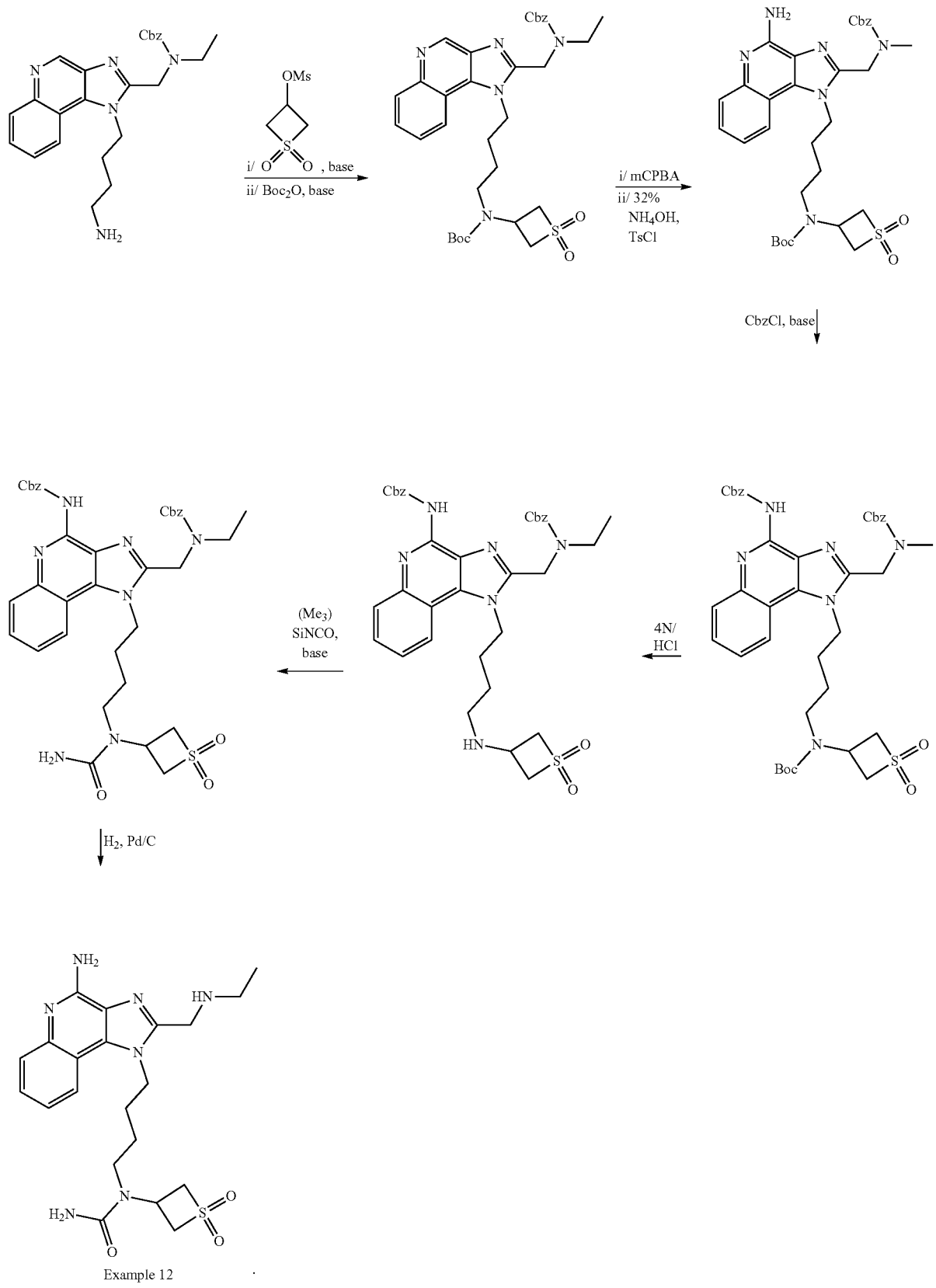
Scheme 9 synthesis of Example 12
Example 12

Example 12

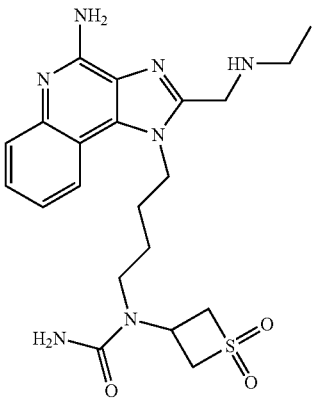 [SMILES: CCNCc1nc2c(N)nc3ccccc3c2n1CCCCN(C(N)=O)C1CS(=O)(=O)C1]

1-(4-(4-Amino-2-((ethylamino)methyl)-1H-imidazo[4,5-c]quinolin-1-yl)butyl)-1-(1,1-dioxidothietan-3-yl)urea Step 1: A 50 mL two-neck round-bottom flask, equipped with a reflux condenser, was charged with a magnetic stir bar, benzyl ((1-(4-aminobutyl)-1H-imidazo[4,5-c]quinolin-2-yl)methyl)(ethyl)carbamate (see preparation E) (1.000 g, 2.317 mmol), 1,1-dioxidothietan-3-yl methanesulfonate (557 mg, 2.781 mmol, 1.2 eq), DIPEA (1.797 g, 13.904 mmol, 6 eq) and a mixture of THF/water (4:1 v/v, 20 mL) to give a yellow suspension that was heated under reflux until TLC monitoring CHCl$_3$/MeOH/32% ammonia solution 90:9:1) and HPLC/MS indicated a complete consumption of the starting material after 2 h. The reaction mixture was then allowed to cool down to room temperature. Di-tert-butyl dicarbonate (Boc$_2$O) (506 mg, 2.317 mmol, 1 eq), N,N-diisopropylethylamine (599 mg, 4.635 mmol, 2 eq) and 4-dimethylaminopyridine (28 mg, 0.232 mmol) were next added and the resulting mixture was stirred at room temperature. After 18 h, TLC monitoring (CHCl$_3$/MeOH/32% ammonia solution 140:9:1) and HPLC/MS indicated an incomplete conversion. Additional Boc$_2$O (506 mg, 2.317 mmol, 1 eq) was added and the reaction mixture was further stirred at 60° C. overnight. TLC monitoring CHCl$_3$/MeOH/32% ammonia solution 140:9:1) and HPLC/MS still indicated an incomplete conversion. Additional Boc$_2$O (1.011 g, 4.635 mmol, 2 eq) and DIPEA (599 mg, 4.635 mmol, 2 eq) were added every 80 min over the next 4 h and the reaction mixture was further stirred at 60° C. to obtain a complete conversion. The reaction mixture was then concentrated under reduced pressure, the residue was dissolved in CH$_2$Cl$_2$ (100 mL) and washed successively with 10% aq. CuSO$_4$ (2×50 mL) and saturated aqueous NaHCO$_3$ (2×50 mL). The organic phase was dried over MgSO$_4$, filtered and concentrated under reduced pressure to get 1.48 g (quantitative, crude) of tert-butyl (4-(2-((((benzyloxy)carbonyl)(ethyl)amino)methyl)-1H-imidazo[4,5-c]quinolin-1-yl)butyl)(1,1-dioxidothietan-3-yl)carbamate as a reddish yellow oil to be used for the next step without additional purification.

MS (ESI+) m/z 636.4 [M+H]$^+$

Step 2: A round bottom flask was charged with a magnetic stir bar, crude tert-butyl (4-(2-((((benzyloxy)carbonyl)(ethyl)amino)methyl)-1H-imidazo[4,5-c]quinolin-1-yl)butyl)(1,1-dioxidothietan-3-yl)carbamate (1.480 g, 2.328 mmol) and CH$_2$Cl$_2$ (20 mL) to give a reddish-yellow solution. Solid 3-chlorobenzoperoxoic acid (1.004 g, 5.820 mmol, 2.5 eq) was added in portions over 5 minutes and the resulting mixture was stirred at room temperature for 3 h. TLC monitoring (CHCl$_3$/MeOH/32% ammonia solution 140:9:1) and HPLC/MS indicated a complete conversion. Ammonia solution (32%, 20 mL) was added to the solution, followed by p-toluenesulfonyl chloride (1.065 g, 5.587 mmol, 2.4 eq) and the biphasic mixture was vigorously stirred at room temperature overnight. TLC monitoring (CHCl$_3$/MeOH/32% ammonia solution 140:9:1) and HPLC/MS indicated a complete conversion. The two layers were separated and the organic layer was washed with water (20 mL), dried over MgSO$_4$, filtered off and concentrated in vacuo to get 1.515 g of tert-butyl (4-(4-amino-2-((((benzyloxy)carbonyl)(ethyl)amino)methyl)-1H-imidazo[4,5-c]quinolin-1-yl)butyl)(1,1-dioxidothietan-3-yl)carbamate as a reddish-yellow oil to be used for the next step without additional purification.

MS (ESI+) m/z 651.4 [M+H]$^+$

Step 3: A round-bottom flask with septum and argon inlet was charged with crude tert-butyl (4-(4-amino-2-((((benzyloxy)carbonyl)(ethyl)amino)methyl)-1H-imidazo[4,5-c]quinolin-1-yl)butyl)(1,1-dioxidothietan-3-yl)carbamate (1.515 g, 2.328 mmol) and CH$_2$Cl$_2$ (20 mL) to give a reddish-yellow solution. Triethylamine (283 mg, 2.793 mmol, 1.2 eq), 4-dimethylatninopyridine (28 mg, 0.233 mmol, 0.1 eq) and benzyl chloroformate (477 mg, 2.793 mmol, 1.2 eq) were then added and the reaction mixture was stirred at room temperature for 2 h. Additional benzyl chloroformate (2.54 g, 14.89 mmol, 6.4 eq) and triethylamine (1.51 g, 14.89 mmol, 6.4 eq) were added in portions over the next 3 h and the reaction mixture was further stirred at room temperature overnight until TLC monitoring (CHCl$_3$/MeOH/32% ammonia solution 140:9:1) and HPLC/MS indicated a complete conversion. The reaction mixture was next poured into saturated aqueous NH$_4$Cl (100 mL) and extracted with dichloroethane (3×50 mL). The combined organic layers were dried over MgSO$_4$, filtered off and concentrated in vacuo. The residue was purified by flash chromatography on silica (30% EtOAc/EtOH 3:1 in petroleum ether containing 2% concentrated ammonia solution) to get 257 mg (14%) of benzyl ((4-(((benzyloxy)carbonyl)amino)-1-(4-((tert-butoxycarbonyl)(1,1-dioxidothietan-3-yl)amino)butyl)-1H-imidazo[4,5-c]quinolin-2-yl)methyl)(ethyl)carbamate as a yellow oil.

MS (ESI+) m/z 785.6 [M+H]$^+$

Step 4: A 10-mL round-bottom flask equipped with a magnetic stir bar was charged with benzyl ((4-(((benzyloxy)carbonyl)amino)-1-(4-((tert-butoxycarbonyl)(1,1-dioxidothietan-3-yl)amino)butyl)-1H-imidazo[4,5-c]quinolin-2-yl)methyl)(ethyl)carbamate (257 mg, 0.327 mmol) and anhydrous 1,4-dioxane (5 mL) to give a yellow solution. After addition of 4N HCl/1,4-dioxane (2.5 mL) the reaction mixture was stirred at room temperature for 60 min. TLC monitoring (50% EtOAc/EtOH 3:1 in petroleum ether containing 2% concentrated ammonia solution) indicated a complete conversion. The reaction mixture was then concentrated in vacuo, the residue was dissolved in methanol and deionized via ion-exchange chromatography on an Agilent StratoSpheres PL-HCO$_3$ MP SPE cartridge (see above) to isolate 230 mg (quantitative, crude) of benzyl ((4-(((benzyloxy)carbonyl)amino)-1-(4-((1,1-dioxidothietan-3-yl)amino)butyl)-1H-imidazo[4,5-c]quinolin-2-yl)methyl)(ethyl)carbamate as a yellow oil. The substance was used in the next experiment without additional purification.

MS (ESI+) m/z 685.4 [M+H]$^+$

Step 5: A round-bottom flask was charged with a magnetic stir bar, benzyl ((4-(((benzyloxy)carbonyl)amino)-1-(4-((1,1-dioxidothietan-3-yl)amino)butyl)-1H-imidazo[4,5-c]quinolin-2-yl)methyl)(ethyl)carbamate (230 mg, 0.336 mmol), triethylamine (47 µL, 0.336 mmol, 1 eq) and anhydrous chloroform (5 mL) and the resulting yellow solution was cooled to 0-4° C. in an ice bath. After addition of trimethylsilyl isocyanate (46 µL, 0.336 mmol, 1 eq) the reaction was stirred at room temperature. The progress of the reaction was monitored by TLC (70% EtOAc/EtOH 3:1 in petroleum ether containing 2% concentrated ammonia solution) and by HPLC/MS. After a reaction time of 45 min, additional trimethylsilyl isocyanate (one drop) was added and further stirring at room temperature for 2 h was necessary to obtain a complete conversion. The reaction was then quenched by addition of water (1 mL) and subsequently stirred at room temperature for 30 min. The mixture was then diluted with absolute ethanol (20 mL) and concentrated under reduced pressure to approximately half of the volume (~10 mL). Absolute ethanol (20 mL) was added and the solution was evaporated in vacuo. The residue was dissolved in a small amount of methanol, loaded to EXtrelut®NT (order No. 1.15092.1000, Merck KGaA) and purified by flash chromatography on silica (40% EtOAc/EtOH 3:1 in petroleum ether containing 2% concentrated ammonia solution) to get 110 mg (45%) of benzyl ((4-(((benzyloxy)carbonyl)amino)-1-(4-(1-(1,1-dioxidothietan-3-yl)ureido)butyl)-1H-imidazo[4,5-c]quinolin-2-yl)methyl)(ethyl)carbamate as a light yellow solid.

MS (ESI+) m/z 728.4 [M+H]$^+$. No NMR measurement was conducted due to the insolubility of the compound in common NMR solvents.

Step 6: A round-bottom flask, equipped with a septum inlet flushing adapter with stopcock, was charged with a magnetic stir bar, benzyl ((4-(((benzyloxy)carbonyl)amino)-1-(4-(1-(1,1-dioxidothietan-3-yl)ureido)butyl)-1H-imidazo[4,5-c]quinolin-2-yl)methyl)(ethyl)carbamate (97 mg, 0.133 mmol) and methanol (20 mL) to give a colorless suspension. After addition of 10% palladium on activated carbon (142 mg, 0.133 mmol, 1 eq) the apparatus was connected to a balloon filled with hydrogen and alternately evacuated and filled with hydrogen three times. Hydrogen was then admitted to the system and the reaction mixture was stirred under atmospheric pressure at room temperature overnight. TLC monitoring (70% EtOAc/EtOH 3:1 in petroleum ether containing 2% concentrated ammonia solution) and HPLC/MS showed a complete consumption of the starting material. The apparatus was purged with argon and the catalyst was removed by filtration through a thin pad of CELITE® Hyflo Supercel on a partly coarse porosity (porosity=16-40 µm) glass filtration funnel. The filter cake was washed with MeOH (3×50 mL), and the combined filtrates were filtered through a 0.45 µm PTFE membrane to remove catalyst residues and concentrated under reduced pressure to get 30 mg (49%) of a yellow-beige solid.

$^1$H NMR (300 MHz, DMSO-d$_6$) δ 8.03 (dd, 1H), 7.61 (dd, 1H), 7.43 (ddd, 1H), 7.27 (ddd, 1H), 6.46 (s, 2H), 6.12 (s, 2H), 4.60 (t, 2H), 4.56-4.37 (m, 3H), 4.33-4.19 (m, 2H), 4.03 (s, 2H), 3.25 (m, 2H), 2.63 (q, 2H), 1.83 (m, 2H), 1.66 (m, 2H), 1.06 (t, 3H); MS (ESI+) m/z 460.1 [M+H]$^+$ Scheme 10 synthesis of Example 13-15

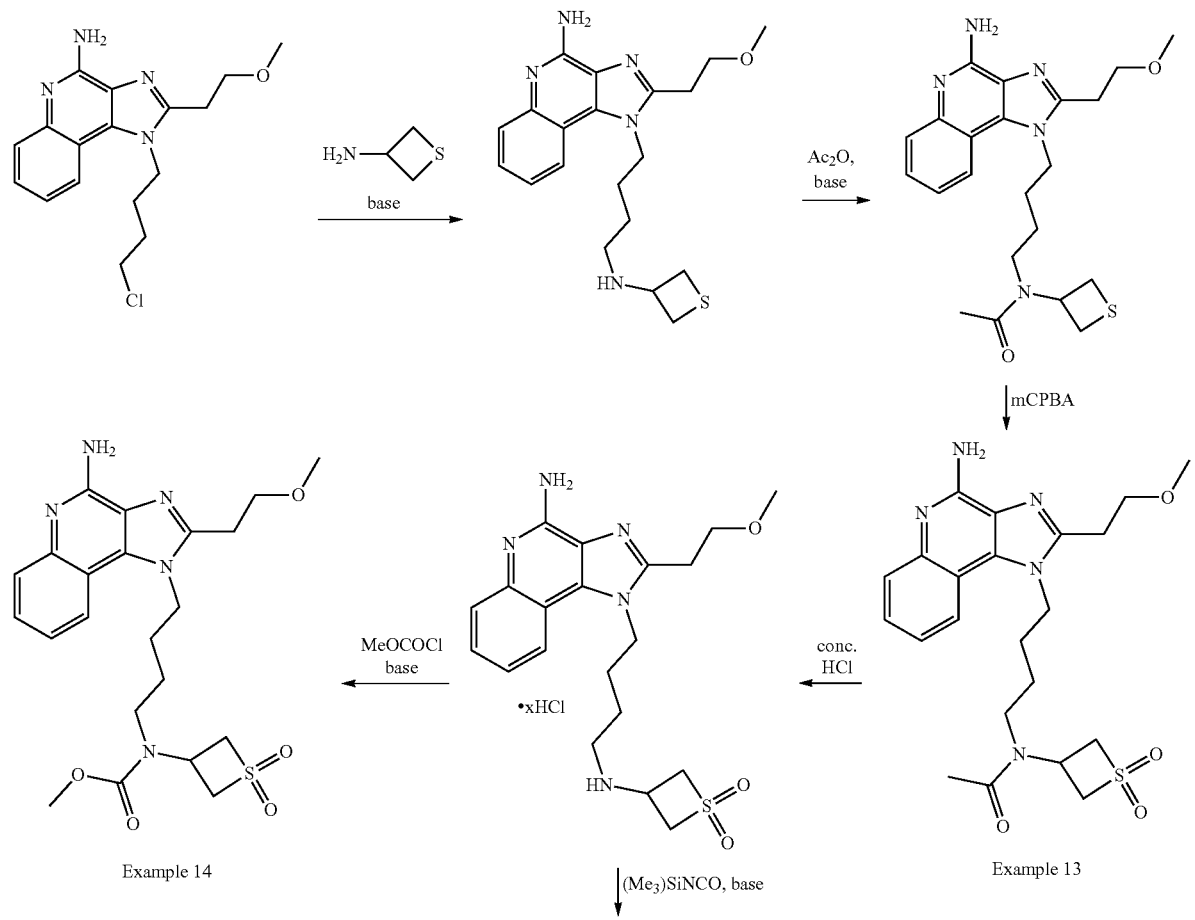

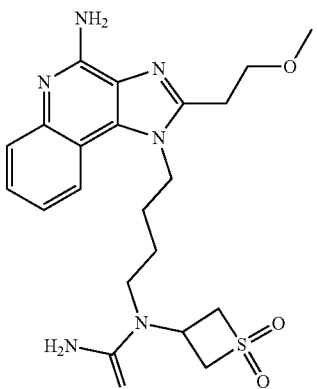

Example 15

Example 13

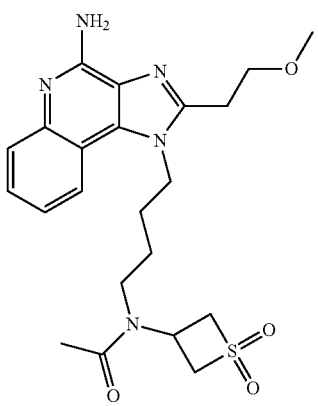 [SMILES: COCCc1nc2c(N)nc3ccccc3c2n1CCCCN(C(C)=O)C1CS(=O)(=O)C1]

N-(4-(4-Amino-2-(2-methoxyethyl)-1H-imidazo[4,5-c]quinolin-1-yl)butyl)-N-(1,1-dioxidothietan-3-yl)acetamide Step 1: To a solution of 1-(4-chlorobutyl)-2-(2-methoxyethyl)-1H-imidazo[4,5-c]quinolin-4-amine (obtained in Example 5, Steps 1-3) (286 mg, 0.859 mmol) in anhydrous DMA (10 mL) were added sodium iodide (129 mg, 0.859 mmol, 1 eq), N-ethyl-N-isopropylpropan-2-amine (449 μL, 2.578 mmol, 3 eq), thietan-3-amine hydrochloride (341 mg, 2.578 mmol, 3 eq) and molecular sieve 4 Å, powder <5 micron (Aldrich) (1.5 g). The yellow reaction mixture was stirred at 100° C. until HPLC/MS monitoring indicated complete reaction and formation of the desired substance after 4 days. The reaction mixture was filtered off and concentrated under reduced pressure to get 504 mg (crude) of 2-(2-methoxyethyl)-1-(4-(thietan-3-ylamino)butyl)-1H-imidazo[4,5-c]quinolin-4-amine as a brown residue. The raw substance was used for the next step without any further purification.

MS (ESI+) m/z 385.9 [M+H]$^+$

Step 2: A pear-shaped flask was charged with a magnetic stir bar, crude 2-(2-methoxyethyl)-1-(4-(thietan-3-ylamino)butyl)-1H-imidazo[4,5-c]quinolin-4-amine (504 mg, 1.3 mmol), 2M NaOH (6.536 mL, 13.07 mmol, 10 eq) and water (5 mL) to give a brownish suspension. After addition of acetic anhydride (1.22 mL, 13.07 mmol, 10 eq), the reaction mixture was stirred at room temperature overnight. HPLC/MS monitoring indicated complete consumption of the starting material. The reaction mixture was filtered off and the product was isolated via preparative HPLC to afford 91 mg (16%) of N-(4-(4-amino-2-(2-methoxyethyl)-1H-imidazo[4,5-c]quinolin-1-yl)butyl)-N-(thietan-3-yl)acetamide as a yellow-beige solid.

MS (ESI+) m/z 427.9 [M+H]$^+$

Step 3: A pear-shaped flask was charged with a magnetic stir bar, N-(4-(4-amino-2-(2-methoxyethyl)-1H-imidazo[4,5-c]quinolin-1-yl)butyl)-N-(thietan-3-yl)acetamide (91 mg, 0.213 mmol), chloroform (5 mL) and methanol (5 mL) to give a light yellow solution. Solid 3-chlorobenzoperoxoic acid (110 mg, 0.638 mmol, 3 eq) was added in portions to the solution and the reaction was stirred at room temperature overnight. HPLC/MS monitoring indicated an incomplete reaction. Additional 3-chlorobenzoperoxoic acid (73 mg, 0.426 mmol, 2 eq) and a further stirring overnight were necessary to obtain a complete conversion of the starting material. The solution was partitioned between chloroform (50 mL) and saturated aqueous NaHCO$_3$ (50 mL). The layers were separated, the organic layer was washed successively with saturated aqueous NaHCO$_3$ (50 mL) and brine (50 mL), dried over Na$_2$SO$_4$, filtered off and concentrated under reduced pressure. The crude substance was purified by preparative HPLC to afford 6.4 mg (7%) of an off-white solid.

$^1$H NMR (300 MHz, DMSO-d$_6$) δ 8.03 (d, 1H), 7.64 (dd, 1H), 7.46 (ddd, 1H), 7.30 (ddd, 1H), 6.42 (s, 2H), 4.66-4.16 (m, 7H), 3.84 (t, 2H), 3.39 (t, 2H), 3.30 (s, 3H), 3.20 (t, 2H), 2.03 (s, 3H), 1.86-1.62 (m, 4H); MS (ESI+) m/z 459.8 [M+H]$^+$

Example 14

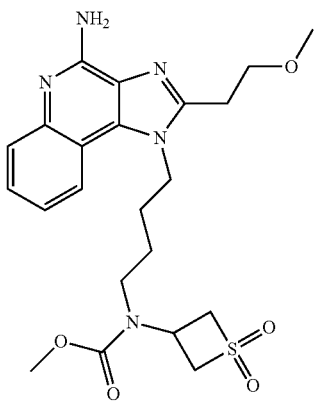 [SMILES: COCCc1nc2c(N)nc3ccccc3c2n1CCCCN(C(=O)OC)C1CS(=O)(=O)C1]

Methyl (4-(4-amino-2-(2-methoxyethyl)-1H-imidazo[4,5-c]quinolin-1-yl)butyl)(1,1-dioxidothietan-3-yl)carbamate Step 1: N-(4-(4-amino-2-(2-methoxyethyl)-1H-imidazo[4,5-c]quinolin-1-yl)butyl)-N-(1,1-dioxidothietan-3-yl)acetamide (Example 13) (440 mg, 0.95 mmol) was suspended in methanol (12 mL) followed by the addition of concentrated HCl (2.5 mL). The mixture was stirred at 100° C. under microwave irradiation until HPLC/MS monitoring indicated almost complete conversion after 2.5 h. The reaction was then diluted with $CH_2Cl_2$ (200 mL) and washed with saturated aqueous $NaHCO_3$. The aqueous phase was extracted twice with $CH_2Cl_2$ and the combined organic phases were dried over $Na_2SO_4$, filtered off and concentrated under reduced pressure to afford 380 mg (87%) of 3-((4-(4-amino-2-(2-methoxyethyl)-1H-imidazo[4,5-c]quinolin-1-yl)butyl)amino)thietane 1,1-dioxide hydrochloride as a light yellow amorphous solid that was used in the next step without any further purification.

MS (ESI+) m/z 418.4 [M+H]+

Step 2: Methyl chloroformate (21 µL, 0.27 mmol, 1 eq) was added at room temperature to a suspension of 3-((4-(4-amino-2-(2-methoxyethyl)-1H-imidazo[4,5-c]quinolin-1-yl)butyl)amino)thietane 1,1-dioxide hydrochloride (114 mg, 0.27 mmol) and $K_2CO_3$ (94 mg, 0.81 mmol, 3 eq) in $H_2O$ (3 mL) and the mixture was stirred overnight at room temperature. HPLC/MS monitoring indicated an incomplete conversion. Additional methyl chloroformate (21 µL, 0.27 mmol, 1 eq) and a further stirring for 1 h were necessary to obtain a complete consumption of the starting material. The reaction mixture was then diluted with $CH_2Cl_2$ (200 mL) and washed with saturated aqueous $NaHCO_3$. The aqueous phase was discarded and the organic phase was dried over $Na_2SO_4$, filtered off and concentrated under reduced pressure. The crude substance was subjected to preparative TLC ($SiO_2$ 20 cm², $CH_2Cl_2$/methanol/32% ammonia solution 190:9:1 to 230:18:2 then $CH_2Cl_2$/methanol/32% ammonia solution 150:9:1) to yield 50 mg (38%) of a white solid.

¹H NMR (300 MHz, DMSO-$d_6$) δ 8.0 (d, 1H), 7.62 (dd, 1H), 7.42 (ddd, 1H), 7.26 (ddd, 1H), 6.43 (s, 2H), 4.59-4.24 (m, 7H), 3.83 (t, 2H), 3.59 (s, 3H), 3.33 (t, 2H), 3.30 (s, 3H), 3.18 (t, 2H), 1.69 (m, 4H); MS (ESI+) m/z 476.5 [M+H]+

Example 15

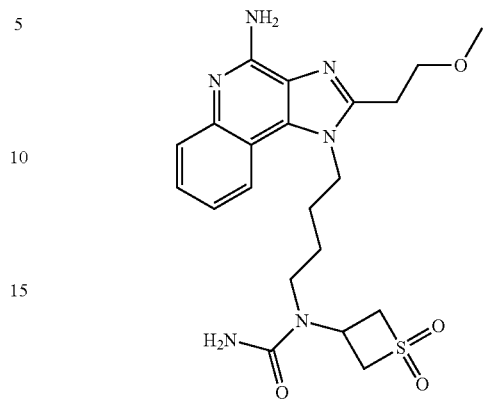

1-(4-(4-Amino-2-(2-methoxyethyl)-1H-imidazo[4,5-c]quinolin-1-yl)butyl)-1-(1,1-dioxidothietan-3-yl)urea 3-((4-(4-amino-2-(2-methoxyethyl)-1H-imidazo[4,5-c]quinolin-1-yl)butyl)amino)thietane 1,1-dioxide hydrochloride (obtained in Example 14, Step 1) (270 mg, 0.64 mmol) and triethylamine (404 µL, 2.91 mmol, 4.5 eq) were mixed in chloroform (10 mL). Trimethylsilyl isocyanate (96 µL, 0.71 mmol, 1.1 eq) was added at 0° C. and the mixture was stirred at room temperature for 2 h. The reaction was monitored by TLC ($CH_2Cl_2$/$CHCl_3$/methanol/32% ammonia solution 100:80:18:2) and HPLC/MS. Additional trimethylsilyl isocyanate (192 µL, 1.40 mmol, 2.2 eq) and further stirring at room temperature overnight were necessary to obtain a complete consumption of the starting material. The reaction mixture was then filtered off and the filtrate was diluted with $CH_2Cl_2$ (200 mL) and washed with saturated aqueous $NaHCO_3$. The aqueous phase was then extracted twice with $CH_2Cl_2$ and the combined organic layers were dried over $Na_2SO_4$, filtered off and concentrated under reduced pressure. The crude substance was purified by preparative TLC ($CH_2Cl_2$/methanol/32% ammonia solution 150:9:1 then 180:18:2) to yield 34 mg (11%) of an off-white solid.

¹H NMR (300 MHz, DMSO-$d_6$) δ 8.04 (d, 1H), 7.63 (d, 1H), 7.44 (t, 1H), 7.29 (t, 1H), 6.57 (br s, 2H), 6.13 (s, 2H), 4.73-4.17 (m, 7H), 3.84 (t, 2H), 3.30 (m, 5H), 3.19 (t, 2H), 1.78 (m, 2H), 1.65 (m, 2H); MS (ESI+) m/z 461.4 [M+H]+

Example A—In Vitro Profiling

IFN-α Induction Assay—IFN-α Induction by TLR Agonists in Human PBMCs

Abbreviations: BSA=bovine serum albumine; PBS=phosphate buffer pH 7.4; PE=phycoerythrin; EDC=1-ethyl-3-(3-dimethylaminopropyl)carbodiimide hydrochloride.

Materials and Devices: Bio Plex 200 Luminex device, and BioPlex Manager software; MultiScreen Filter Plates (Millipore, MABVN1250); low binding reaction vials 1.5 ml (Sarstedt, 72.706.600); Activation Buffer: 0.1M Na-dihydrogen phosphate, 0.1M Di-Na hydrogen phosphate pH 6.2; Sulfo-NHS (N-hydroxysulfosuccinimide) solution: 50 mg/ml in water (freshly prepared); EDC solution: 50 mg/ml in water (freshly prepared); Coupling Buffer: PBS; Washing Buffer: PBS+0.05% Tween20; Blocking Buffer: PBS+10 mg/ml BSA+0.05% sodium azide; Assay Buffer: PBS+10 mg/ml BSA;

Other materials and devices (pipets, reaction vessels, shaker, etc.) were standard lab equipment; water was MilliQ grade quality, buffers were sterile filtered before use.

(Pre-)Incubation of Cells:

In each well of a 96-well U-bottom plate 200,000 PBMCs were pre-incubated in medium (RPMI1640—Gibco #61870-044+10% FBS+1% L-glutamine) for 5 hours at 37° C. and 5% $CO_2$ before the compounds of the present invention or controls were added, respectively. Upon addition of compounds of the present invention or controls, the cells are incubated for another 24 h at 37° C. and 5% $CO_2$.

Luminex assay, Step 1: Coupling of antibody to beads:
transfer a suspension (beads are stored in buffer as provided by manufacturer) of about 5 million MicroPlex Microspheres (=beads) into a low binding reaction vial
centrifuge bead suspension for 1 min at 10,000 g, discard supernatant and resuspend pellet in 160 µl Activation Buffer, repeat once
add 20 µl Sulfo-NHS solution and 20 µl EDC solution, vortex
incubate for 20 min in the absence of light
centrifuge bead suspension for 1 min at 10,000 g, discard supernatant and resuspend pellet in 500 µl Coupling Buffer, repeat once
add capture antibody (CaptureAK eBioscience #BMS160, 5 µg per 1 Mio beads)
incubate 2 h at RT in the absence of light while swaying
centrifuge bead suspension for 1 min at 10,000 g, discard supernatant and resuspend pellet in 500 µl Washing Buffer, repeat once
centrifuge bead suspension for 1 min at 10,000 g, discard supernatant and resuspend pellet in 100 µl Blocking Buffer Luminex assay, Step 2: Measurement
add 100 µl Assay Buffer into each filter plate well (seal any unused wells with adhesive tape), then remove buffer
add about 2,000 beads per well per analyte (per analyte, a different bead type with distinct fluorescence color is used), suspended in 50 µl of Assay Buffer
remove buffer and wash twice with 100 µl Washing Buffer per well
per well, add 50 µl sample solution from the (pre-) incubation step (cell supernatant), or Standard (IFN-α standard eBioscience #BMS216MST—concentration gradient, highest standard concentration 2500 pg/ml) or Assay Buffer (as blanks)
shake plate
incubate plate for 2 h at RT in the absence of light, while swaying the plate
wash three times with 100 µl Washing Buffer per well
add 25 µl antibody detection mix (DetectionAK eBioscience #BMS1016BT diluted 1:1000) in Assay Buffer per well, then vortex plate
incubate plate for 1 h at RT in the absence of light, while swaying the plate
wash three times with 100 µl Washing Buffer per well
add 50 µl Streptavidin/PE (diluted 1:200 in Assay Buffer) per well, then vortex plate
incubate plate for 10 min at RT in the absence of light, while swaying the plate
wash three times with 100 µl Washing Buffer per well
add 100 µl Assay Buffer per well, then vortex plate
start Luminex measurement according to manufacturer's instructions, measuring at least 50 beads per well per analyte The compounds were tested at 8 different concentrations (1 µM, 0.3 µM, 0.1 µM, 0.03 µM, 0.01 µM 0.003 µM, 0.001 µM, 0.0003 µM) using a half-logarithmic dilution. The release of Interferon-alpha (IFN-α) presents a bell-shaped distribution within the dilution window. The minimum effective concentration (MEC) is the lowest concentration required to induce the desired IFN-α release. It represents the outset of the bell-shaped distribution and is given in nM. In other words, the MEC determines if a compound can be administered at lower concentrations while achieving the desired IFN-α release.

The compounds of present Examples 7-15 showed the following results:

TABLE 1

| Example | Structure | MW | Minimum effective concentration IFN-α release (nM) |
|---|---|---|---|
| 7 | 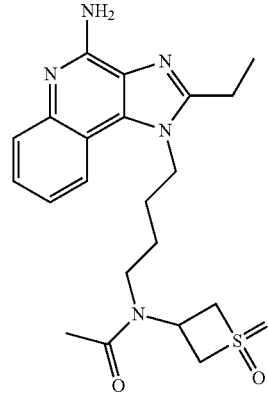 | 429.54 | 100 |
| 8 | 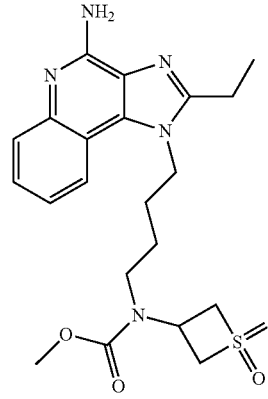 | 445.54 | 30 |

TABLE 1-continued

| Example | Structure | MW | Minimum effective concentration IFN-α release (nM) |
|---|---|---|---|
| 9 | 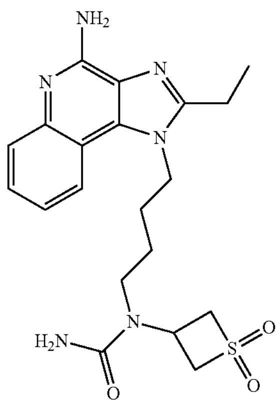 [SMILES: CCc1nc2c(N)nc3ccccc3c2n1CCCCN(C(N)=O)C1CS(=O)(=O)C1] | 430.53 | 100 |
| 10 | 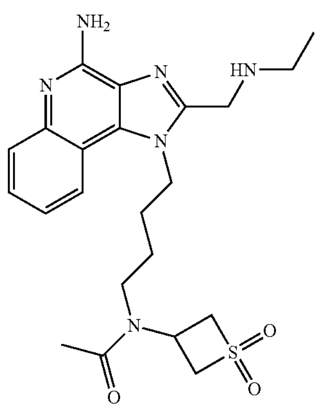 [SMILES: CCNCc1nc2c(N)nc3ccccc3c2n1CCCCN(C(C)=O)C1CS(=O)(=O)C1] | 458.58 | 1000 |
| 11 | 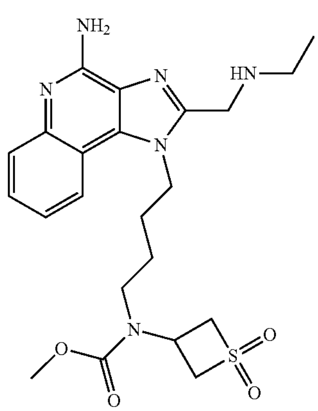 [SMILES: CCNCc1nc2c(N)nc3ccccc3c2n1CCCCN(C(=O)OC)C1CS(=O)(=O)C1] | 474.58 | 100 |
| 12 | | 459.57 | 3000 |
| 13 | | 459.57 | 10 |
| 14 | | 475.56 | 1 |

TABLE 1-continued

| Example | Structure | MW | Minimum effective concentration IFN-α release (nM) |
|---|---|---|---|
| 15 | (structure) | 460.55 | 10 |

As can be seen from the data in following Table 2, corresponding comparative compounds bearing a 1,1-dioxidotetrahydro-3-thienyl group instead of the 1,1-dioxidothietantetrahydro-3-thienyl group at position R3 (e.g., N-[4-(4-amino-2-ethyl-1H-imidazo[4,5-c]quinolin-1-yl)butyl]-N-(1,1-dioxidotetrahydro-3-thienyl)acetamide, a compound described in WO-A-2009/118296 as example I) showed at least a three times higher minimum effective concentration for IFN-α release, compared to the compounds of the present invention, or were not even active at all.

TABLE 2

| Comparative Compound | Structure | Minimum effective concentration IFN-α release (nM) |
|---|---|---|
| 7' | (structure) | 300 |
| 8' | (structure) | 100 |
| 9' | (structure) | 300 |
| 10' | (structure) | inactive |

TABLE 2-continued

| Comparative Compound | Structure | Minimum effective concentration IFN-α release (nM) |
|---|---|---|
| 11' | (structure) | inactive |
| 12' | (structure) | 10000 |
| 13' | (structure) | 30 |
| 14' | (structure) | 10 |
| 15' | (structure) | 100 |

Example B—In Vivo Profiling

In the following studies, a compound according to the invention was examined in an in vivo cynomolgus monkey model. It is evaluated whether and at which applied dose the compounds cause secretion of IFN-α.

In particular, a defined single dose of test compound was applied intravenously to cynomolgus monkeys by a thirty minute infusion. At several time points after initiation of the intravenous compound application, blood samples (0.5 mL for approximately 0.25 mL plasma) were collected from the vena cephalica antebrachii or vena saphena into $K_3$EDTA tubes from the animals. Blood samples were stored on crushed ice prior to centrifugation. Plasma was obtained by centrifugation at 4° C. and approximately 1800 g for 10 minutes and was aliquoted into labeled micro tubes and stored frozen at −70° C. or below. Plasma samples were thawed, diluted and used for determination of IFN-α levels using an IFN-α Elisa Kit (e.g. VeriKine™ Cynomolgus/Rhesus IFN-α ELISA Kit) according to the manufacturer's instructions.

Results show that compounds of the present invention cause IFN-α secretion in vivo in cynomolgus monkeys, whereas application of vehicle does not result in measurable IFN-α levels. Blood plasma peak concentrations of IFN-α are usually reached approximately 150 minutes after initiation of compound application. In particular, application of a single dose of 10, 3, or 1 mg/kg of the compound of Example 7 of the present invention results in peak plasma IFN-α concentrations of about 30,000 pg/ml, about 2500 to about 22,000 pg/ml, and about 3000 to about 15,000 pg/ml, respectively. The smallest dose tested for the compound of Example 7 was 0.3 mg/kg, resulting in peak plasma IFN-α concentrations of about 5000 pg/ml.

The invention claimed is:

1. A compound having the general Formula (I):

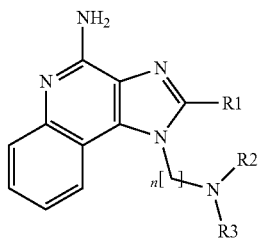

wherein

R1 is selected from the group consisting of —H, $C_{1-6}$-alkyl, $C_{1-6}$-alkoxy, $C_{1-3}$-alkoxy-$C_{1-3}$-alkyl, $C_{1-6}$-alkylthio, $C_{1-3}$-alkylthio-$C_{1-3}$-alkyl, $C_{1-3}$-alkylamino-$C_{1-3}$-alkyl, 4- to 10-membered heterocycloalkyl, $C_{3-10}$-cycloalkyl, $C_{6-10}$-aryl, $C_{6-10}$-aryl-$C_{1-2}$-alkyl and 5- to 10-membered heteroaryl, wherein said $C_{1-6}$-alkyl, $C_{1-6}$-alkoxy, $C_{1-3}$-alkoxy-$C_{1-3}$-alkyl, $C_{1-6}$-alkylthio, $C_{1-3}$-alkylthio-$C_{1-3}$-alkyl, $C_{1-3}$-alkylamino-$C_{1-3}$-alkyl, $C_{6-10}$-aryl, 4- to 10-membered heterocycloalkyl, $C_{3-10}$-cycloalkyl, $C_{6-10}$-aryl-$C_{1-2}$-alkyl and 5- to 10-membered heteroaryl is optionally substituted by one or more groups independently selected from the group consisting of $C_{1-4}$-alkyl, —OH, halogen, —CO—N(R4)$_2$, —N(R4)$_2$, —CO—R4, —COO—R4, —N$_3$, —NO$_2$, and —CN;

R2 is selected from the group consisting of —CO—R5, —CONH—R5, and —COO—R5;

R3 is 1,1-dioxothietan-3-yl, which is optionally substituted by one or more groups independently selected from the group consisting of $C_{1-4}$-alkyl, —OH, and halogen;

R4 is each independently selected from the group consisting of H and $C_{1-4}$-alkyl;

n is an integer from 3 to 6; and

R5 is selected from the group consisting of —H, $C_{1-6}$-alkyl, $C_{1-6}$-alkoxy, $C_{1-3}$-alkoxy-$C_{1-3}$-alkyl, $C_{1-6}$-alkylthio, $C_{1-3}$-alkylthio-$C_{1-3}$-alkyl, $C_{1-3}$-alkylamino-$C_{1-3}$-alkyl, $C_{6-10}$-aryl, 4- to 10-membered heterocycloalkyl, $C_{3-10}$-cycloalkyl and 5- to 10-membered heteroaryl, wherein said $C_{1-6}$-alkyl, $C_{1-6}$-alkoxy, $C_{1-3}$-alkoxy-$C_{1-3}$-alkyl, $C_{1-6}$-alkylthio, $C_{1-3}$-alkylthio-$C_{1-3}$-alkyl, $C_{1-3}$-alkylamino-$C_{1-3}$-alkyl, $C_{6-10}$-aryl, 4- to 10-membered heterocycloalkyl, $C_{3-10}$-cycloalkyl and 5- to 10-membered heteroaryl is optionally substituted by one or more groups independently selected from the group consisting of $C_{1-4}$-alkyl, —OH, halogen, —CO—N(R4)$_2$, —N(R4)$_2$, —CO—R4, —COO—R4, —N$_3$, —NO$_2$, and —CN;

or a physiologically functional derivative, solvate or salt thereof.

2. The compound, physiologically functional derivative, solvate or salt thereof according to claim 1, wherein R1 is selected from the group consisting of $C_{1-3}$-alkoxy-$C_{1-3}$-alkyl, $C_{1-3}$-alkylthio-$C_{1-3}$-alkyl, and $C_{1-3}$-alkylamino-$C_{1-3}$-alkyl, particularly $C_{1-6}$-alkyl, $C_{1-3}$-alkoxy-$C_{1-3}$-alkyl, and $C_{1-3}$-alkylamino-$C_{1-3}$-alkyl, wherein said $C_{1-6}$-alkyl, $C_{1-3}$-alkoxy-$C_{1-3}$-alkyl, $C_{1-3}$-alkylthio-$C_{1-3}$-alkyl, or $C_{1-3}$-alkylamino-$C_{1-3}$-alkyl is optionally substituted by one or more groups independently selected from the group consisting of —OH and halogen.

3. The compound, physiologically functional derivative, solvate or salt thereof according to claim 1, wherein R1 is selected from the group consisting of ethyl, methyl, propyl, butyl, methoxyethyl, and ethylaminomethyl, each of which is optionally substituted by one or more groups independently selected from the group consisting of —OH and halogen.

4. The compound, physiologically functional derivative, solvate or salt thereof according to claim 1, wherein R2 is selected from the group consisting of —CO—R5, —COO—R5, and —CONH—R5.

5. The compound, physiologically functional derivative, solvate or salt thereof according to claim 4, wherein R2 is —CO—R5 or —CONH—R5.

6. The compound, physiologically functional derivative, solvate or salt thereof according to claim 4, wherein R2 is —CO—R5.

7. The compound, physiologically functional derivative, solvate or salt thereof according to claim 1, wherein R3 unsubstituted 1,1-dioxothietan-3-yl.

8. The compound, physiologically functional derivative, solvate or salt thereof according to claim 1, wherein n is an integer from 3 to 5.

9. The compound, physiologically functional derivative, solvate or salt thereof according to claim 8, wherein n is 4.

10. The compound, physiologically functional derivative, solvate or salt thereof according to claim 1, selected from the group consisting of:

N-(4-(4-amino-2-ethyl-1H-imidazo[4,5-c]quinolin-1-yl)butyl)-N-(1,1-dioxidothietan-3-yl)acetamide;

methyl (4-(4-amino-2-ethyl-1H-imidazo[4,5-c]quinolin-1-yl)butyl)(1,1-dioxidothietan-3-yl)carbamate;

1-(4-(4-amino-2-ethyl-1H-imidazo[4,5-c]quinolin-1-yl)butyl)-1-(1,1-dioxidothietan-3-yl)urea;

N-(4-(4-amino-2-((ethylamino)methyl)-1H-imidazo[4,5-c]quinolin-1-yl)butyl)-N-(1,1-dioxidothietan-3-yl)acetamide;

methyl (4-(4-amino-2-((ethylamino)methyl)-1H-imidazo[4,5-c]quinolin-1-yl)butyl)(1,1-dioxidothietan-3-yl)carbamate;

1-(4-(4-amino-2-((ethylamino)methyl)-1H-imidazo[4,5-c]quinolin-1-yl)butyl)-1-(1,1-dioxidothietan-3-yl)urea;

N-(4-(4-amino-2-(2-methoxyethyl)-1H-imidazo[4,5-c]quinolin-1-yl)butyl)-N-(1,1-dioxidothietan-3-yl)acetamide;

methyl (4-(4-amino-2-(2-methoxyethyl)-1H-imidazo[4,5-c]quinolin-1-yl)butyl)(1,1-dioxidothietan-3-yl)carbamate;

1-(4-(4-amino-2-(2-methoxyethyl)-1H-imidazo[4,5-c]quinolin-1-yl)butyl)-1-(1,1-dioxidothietan-3-yl)urea;

and a physiologically functional derivative, solvate or salt thereof.

11. A pharmaceutical composition comprising a compound, physiologically functional derivative, solvate or salt thereof according to claim 1 and one or more pharmaceutically acceptable excipients.

12. A method of treatment of cancer comprising the administration of an effective amount of a compound, physiologically functional derivative, solvate or salt thereof according to claim 1 to a subject in need thereof, wherein the treatment refers to a complete or partial healing of the cancer, alleviation of the cancer or stopping progression of the cancer.

13. A method of treatment of cancer comprising the administration of an effective amount of a pharmaceutical composition according to claim 11 to a subject in need thereof, wherein the treatment refers to a complete or partial healing of the cancer, alleviation of the cancer or stopping progression of the cancer.

14. The method of treatment of cancer according to claim 12, wherein the cancer is a cancer that can be treated by agonizing TLR7.

15. The method of treatment of cancer according to claim 13, wherein the cancer is a cancer that can be treated by agonizing TLR7.

\* \* \* \* \*